United States Patent
Duan et al.

(10) Patent No.: US 12,221,432 B2
(45) Date of Patent: Feb. 11, 2025

(54) ESTROGEN RECEPTOR ANTAGONIST

(71) Applicant: CHIA TAI TIANQING PHARMACEUTICAL GROUP CO., LTD., Lianyungang (CN)

(72) Inventors: Shuwen Duan, Shanghai (CN); Jianyu Lu, Shanghai (CN); Lihong Hu, Shanghai (CN); Charles Z. Ding, Shanghai (CN); Guoping Hu, Shanghai (CN); Jian Li, Shanghai (CN); Shuhui Chen, Shanghai (CN)

(73) Assignee: CHIA TAI TIANQING PHARMACEUTICAL GROUP CO., LTD., Lianyungang (CN)

( * ) Notice: Subject to any disclaimer, the term of this patent is extended or adjusted under 35 U.S.C. 154(b) by 878 days.

(21) Appl. No.: 17/309,712

(22) PCT Filed: Dec. 17, 2019

(86) PCT No.: PCT/CN2019/126046
§ 371 (c)(1),
(2) Date: Jun. 16, 2021

(87) PCT Pub. No.: WO2020/125640
PCT Pub. Date: Jun. 25, 2020

(65) Prior Publication Data
US 2022/0033376 A1   Feb. 3, 2022

(30) Foreign Application Priority Data

Dec. 17, 2018 (CN) .......................... 201811545117.2
Jul. 8, 2019 (CN) .......................... 201910611070.3
Sep. 17, 2019 (CN) .......................... 201910877339.2

(51) Int. Cl.
*C07D 401/06* (2006.01)
*A61P 35/00* (2006.01)
*C07D 209/20* (2006.01)
*C07D 401/14* (2006.01)
*C07D 409/14* (2006.01)

(52) U.S. Cl.
CPC ............ *C07D 401/06* (2013.01); *A61P 35/00* (2018.01); *C07D 209/20* (2013.01); *C07D 401/14* (2013.01); *C07D 409/14* (2013.01)

(58) Field of Classification Search
None
See application file for complete search history.

(56) References Cited

U.S. PATENT DOCUMENTS

| | | | |
|---|---|---|---|
| 8,299,112 B2 | 10/2012 | Smith | |
| 9,499,538 B2 | 11/2016 | Smith | |
| 9,796,683 B2 | 10/2017 | Bock | |
| 2019/0106414 A1 | 4/2019 | Lu | |

FOREIGN PATENT DOCUMENTS

| | | |
|---|---|---|
| CN | 103189361 A | 7/2013 |
| CN | 104220426 A | 12/2014 |
| CN | 107847498 A | 3/2018 |
| WO | WO 2016/196342 A1 | 12/2016 |
| WO | WO 2017/162206 | 9/2017 |
| WO | WO 2018/098251 A1 | 5/2018 |

OTHER PUBLICATIONS

International Search Report in International Application No. PCT/CN2019/126046, mailed Mar. 18, 2020 (8 pages).
Extended European Search report—EPO—EP19900858.2—Dated Aug. 8, 2022.

*Primary Examiner* — Bong-Sook Baek
(74) *Attorney, Agent, or Firm* — NIXON PEABODY LLP

(57) ABSTRACT

Provided is an indole compound. In particular, disclosed are a compound represented by formula (II) or an isomer or pharmaceutically acceptable salt thereof and a use of the same as an estrogen receptor antagonist in preparing a drug for treating estrogen receptor-positive breast cancer.

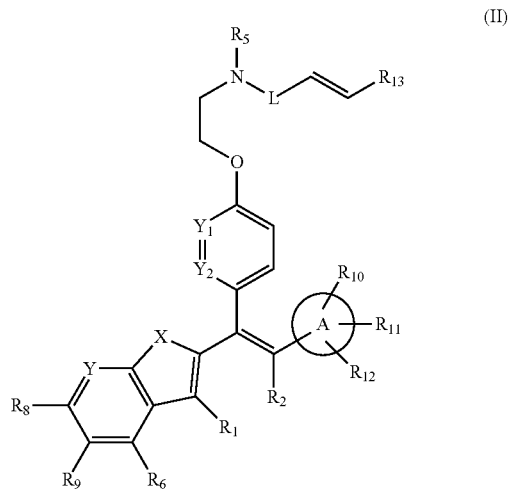

20 Claims, No Drawings

ESTROGEN RECEPTOR ANTAGONIST

CROSS-REFERENCE TO RELATED APPLICATIONS

The present application is a U.S. national stage of PCT/CN2019/126046, filed on Dec. 17 2019, which claims the benefits and priority to Chinese Patent Application No. 201811545117.2 filed with the National Intellectual Property Administration, PRC on Dec. 17, 2018, Chinese Patent Application No. 201910611070.3 filed with the National Intellectual Property Administration, PRC on Jul. 8, 2019, and Chinese Patent Application No. 201910877339.2 filed with the National Intellectual Property Administration, PRC on Sep. 17, 2019, all of which are incorporated herein by reference in their entirety.

TECHNICAL FIELD

The present application relates to novel indole compounds, and specifically discloses a compound of formula (II), an isomer thereof, or a pharmaceutically acceptable salt thereof, and use of the same as an estrogen receptor antagonist in preparing a medicament for treating estrogen receptor positive breast cancer.

BACKGROUND

According to WHO statistics, breast cancer ranks the second among cancers in global population and the first in women in incidence. After years of research, the role of the estrogen-estrogen receptor signaling pathway in the development of breast cancer has been determined; estrogen receptor (ER) has become the most important biomarker of breast cancer. Based on estrogen receptor expression, breast cancers can be classified into estrogen receptor positive breast cancer and estrogen receptor negative breast cancer. Among them, estrogen receptor positive breast cancer accounts for more than 70% in breast cancer patients.

Endocrine therapy (ET) for the estrogen-estrogen receptor signaling pathway in breast cancer cells has become the first choice for estrogen receptor positive breast cancer due to its minimal harm and remarkable efficacy.

Generally, the first-line endocrine therapy is aromatase inhibitor (AI). Although letrozole, an aromatase inhibitor, has demonstrated good efficacy in treating estrogen receptor positive breast cancer, with the marketing of two drugs of the kind, the resistance problem of estrogen recepor positive breast cancer to AIs is becoming prominent. A large number of studies suggest that for AIs, the estrogen receptor gene may mutate, mainly in Y537X, producing a estrogen receptor mutant that may keep an excited conformation in the absence of estrogen and continue to function as a receptor to promote breast cancer cell proliferation. As the only marketed selective estrogen receptor down-regulator, fulvestrant has demonstrated good results in treating hormone-resistant breast cancer. However, fulvestrant has many problems for the treatment of AI-resistant ER mutant breast cancer. Due to its poor pharmacokinetics (PK), fulvestrant features zero bioavailability via oral administration, while having a high blood clearance rate. For the above two reasons, this drug can only be administered by intramuscular injection. However, because of its strong lipophilicity, fulvestrant administered by intramuscular injection also has serious problems in tissue distribution, resulting in a clinical response rate of about 50% in breast cancer patients. Also due to the poor PK properties, the current approved dosage of fluvistran cannot cause complete degradation of ER, especially mutant ER, at tissue concentration. Therefore, the therapy is far from optimal for AI-resistant ER-mutant breast cancer. Therefore, the development of medications targeting ER-mutant breast cancer with better PK remains an unmet medical need. Patent No. US20160347717A1 reported an oral covalent estrogen receptor antagonist H3B-6545. The phase I/II clinical trial of this molecule for the treating ER-positive breast cancer is underway.

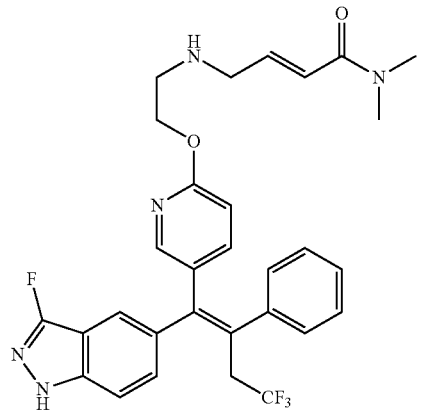

H3B-6545

SUMMARY OF THE INVENTION

The present application provides a compound of formula (II), an isomer thereof or a pharmaceutically acceptable salt thereof,

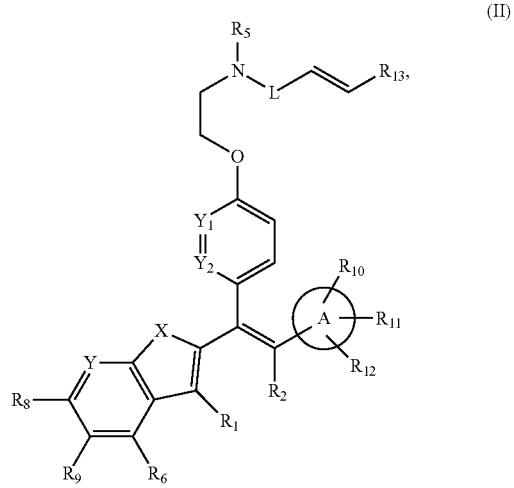

(II)

wherein,

X is selected from the group consisting of NH, O and S;

Y is selected from the group consisting of N and $CR_7$;

$Y_1$ is CH, and $Y_2$ is N;

or, $Y_1$ is N, and $Y_2$ is CH or CF;

or, $Y_1$ is CH, and $Y_2$ is CH;

L is

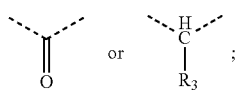

ring A is selected from the group consisting of $C_{6-10}$ aryl and 5-10 membered heteroaryl;

$R_1$ is selected from the group consisting of H, halogen, CN, COOH, $NH_2$, $C_{1-6}$ alkyl, $C_{1-6}$ heteroalkyl, $C_{3-6}$ cycloalkyl and 3-6 membered heterocycloalkyl, the $C_{1-6}$ alkyl, $C_{1-6}$ heteroalkyl, $C_{3-6}$ cycloalkyl and 3-6 membered heterocycloalkyl being optionally substituted with 1, 2 or 3 $R_a$;

$R_2$ is selected from the group consisting of $C_{1-6}$ alkyl, $C_{1-6}$ heteroalkyl, $C_{3-6}$ cycloalkyl and 3-6 membered heterocycloalkyl, the $C_{1-6}$ alkyl, $C_{1-6}$ heteroalkyl, $C_{3-6}$ cycloalkyl and 3-6 membered heterocycloalkyl being optionally substituted with 1, 2 or 3 $R_b$;

$R_3$ is selected from the group consisting of H, halogen, CN, $NO_2$, OH, COOH, $NH_2$, $C_{1-6}$ alkyl, $C_{1-6}$ heteroalkyl, $C_{3-6}$ cycloalkyl and 3-6 membered heterocycloalkyl, the $C_{1-6}$ alkyl, $C_{1-6}$ heteroalkyl, $C_{3-6}$ cycloalkyl and 3-6 membered heterocycloalkyl being optionally substituted with 1, 2 or 3 $R_c$;

$R_{13}$ is H or

$R_4$ is selected from the group consisting of COOH, $NH_2$, $C_{1-6}$ alkyl, $C_{1-6}$ heteroalkyl, $C_{3-6}$ cycloalkyl, 3-6 membered heterocycloalkyl, phenyl and 5-6 membered heteroaryl, the $C_{1-6}$ alkyl, $C_{1-6}$ heteroalkyl, $C_{3-6}$ cycloalkyl, 3-6 membered heterocycloalkyl, phenyl and 5-6 membered heteroaryl being optionally substituted with 1, 2 or 3 $R_d$;

$R_5$ is selected from the group consisting of H, $C_{1-6}$ alkyl, $C_{1-6}$ heteroalkyl, $C_{3-6}$ cycloalkyl and 3-6 membered heterocycloalkyl, the $C_{1-6}$ alkyl, $C_{1-6}$ heteroalkyl, $C_{3-6}$ cycloalkyl and 3-6 membered heterocycloalkyl being optionally substituted with 1, 2 or 3 $R_e$;

$R_6$, $R_7$, $R_8$ and $R_9$ are each independently selected from the group consisting of H, halogen, CN, $NO_2$, OH, COOH, $NH_2$, $C_{1-6}$ alkyl, $C_{1-6}$ heteroalkyl, $C_{3-6}$ cycloalkyl and 3-6 membered heterocycloalkyl, the $C_{1-6}$ alkyl, $C_{1-6}$ heteroalkyl, $C_{3-6}$ cycloalkyl and 3-6 membered heterocycloalkyl being optionally substituted with 1, 2 or 3 $R_f$;

$R_{10}$, $R_{11}$, and $R_{12}$ are each independently selected from the group consisting of H, halogen, CN, $NO_2$, OH, COOH, $NH_2$, $C_{1-6}$ alkyl, $C_{1-6}$ heteroalkyl, $C_{3-6}$ cycloalkyl and 3-6 membered heterocycloalkyl, the $C_{1-6}$ alkyl, $C_{1-6}$ heteroalkyl, $C_{3-6}$ cycloalkyl and 3-6 membered heterocycloalkyl being optionally substituted with 1, 2 or 3 $R_g$;

$R_a$, $R_b$, $R_c$, $R_d$, $R_e$, $R_f$ and $R_g$ are each independently selected from the group consisting of H, F, Cl, Br, I, OH, CN, $NH_2$, COOH, $C(=O)NH_2$, $C_{1-8}$ alkyl, $C_{1-8}$ heteroalkyl, $C_{3-6}$ cycloalkyl, 3-6 membered heterocycloalkyl and $C_{3-6}$ cycloalkyl-$C_{1-3}$ alkyl-, the $C_{1-8}$ alkyl, $C_{1-8}$ heteroalkyl, $C_{3-6}$ cycloalkyl, 3-6 membered heterocycloalkyl and $C_{3-6}$ cycloalkyl-$C_{1-3}$ alkyl- being optionally substituted with 1, 2 or 3 R;

R is independently selected from the group consisting of F, Cl, Br, I, OH, CN, $NH_2$, COOH, Me, Et, $CF_3$, $CHF_2$, $CH_2F$, $NHCH_3$, and $N(CH_3)_2$;

the $C_{1-6}$ heteroalkyl, 3-6 membered heterocycloalkyl and 5-6 membered heteroaryl each comprise 1, 2, 3 or 4 heteroatoms or heteroatom groups each independently selected from the group consisting of —NH—, —O—, —S—, —O—N=, —C(=O)—O—, —C(=O)—S—, —C(=O)—, —C(=S)—, —S(=O)—, —S(=O)$_2$— and N.

In some embodiments of the present application, X is selected from the group consisting of NH, O and S; Y is $CR_7$; $Y_1$ is CH and $Y_2$ is N, or, $Y_1$ is N and $Y_2$ is CH; L is

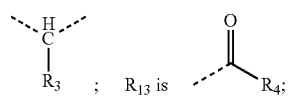

the other variables are as defined in the present application.

In some embodiments of the present application, X is NH; Y is $CR_7$; $Y_1$ is N, and $Y_2$ is CH; L is

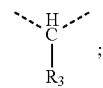

$R_{13}$ is

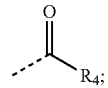

the other variables are as defined in the present application.

In some embodiments of the present application, X is NH; Y is $CR_7$; $Y_1$ is CH, and $Y_2$ is N; L is

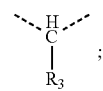

$R_{13}$ is

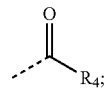

the other variables are as defined in the present application.

In some embodiments of the present application, X is NH; Y is N; $Y_1$ is N, and $Y_2$ is CH; L is

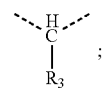

$R_{13}$ is

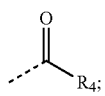

the other variables are as defined in the present application.

In some embodiments of the present application, R is independently selected from the group consisting of F, Cl, Br and I.

In some embodiments of the present application, $R_a$, $R_b$, $R_c$, $R_d$, $R_e$, $R_f$ and $R_g$ are each independently selected from the group consisting of H, F, Cl, Br, I, OH, CN, $NH_2$, COOH, $C(=O)NH_2$, $C_{1-6}$ alkyl, $C_{1-6}$ heteroalkyl and cyclopropyl, the $C_{1-6}$ alkyl, $C_{1-6}$ heteroalkyl and cyclopropyl being optionally substituted with 1, 2 or 3 R; the other variables are as defined in the present application.

In some embodiments of the present application, $R_a$, $R_b$, $R_c$, $R_d$, $R_e$, $R_f$ and $R_g$ are each independently selected from the group consisting of H, F, Cl, Br, I, OH, CN, $NH_2$, COOH, $C(=O)NH_2$, Me, Et, $CF_3$, $CHF_2$, $CH_2F$, $NHCH_3$ and $N(CH_3)_2$; the other variables are as defined in the present application.

In some embodiments of the present application, $R_a$, $R_b$, $R_c$, $R_d$, $R_e$, $R_f$ and $R_g$ are each independently selected from the group consisting of F, Cl, Br, I, Me, Et, $CF_3$, $CHF_2$ and $CH_2F$; the other variables are as defined in the present application.

In some embodiments of the present application, $R_b$ is selected from the group consisting of F, Cl, Br and I; the other variables are as defined in the present application.

In some embodiments of the present application, $R_d$ is $C_{1-6}$ alkyl, the $C_{1-6}$ alkyl being optionally substituted with 1, 2 or 3 R selected from the group consisting of F, Cl, Br and I; the other variables are as defined in the present application.

In some embodiments of the present application, $R_d$ is methyl, the methyl being optionally substituted with 1, 2, or 3 R, wherein R is F; the other variables are as defined in the present application.

In some embodiments of the present application, $R_d$ is selected from the group consisting of $CF_3$, $CHF_2$ and $CH_2F$; the other variables are as defined in the present application.

In some embodiments, $R_d$ is $CH_2F$; the other variables are as defined in the present application.

In some embodiments, ring A is selected from the group consisting of phenyl and 5-6 membered heteroaryl; the other variables are as defined in the present application.

In some embodiments, ring A is selected from the group consisting of phenyl, 5-membered sulfur-containing heteroaryl, and 6-membered nitrogen-containing heteroaryl; the other variables are as defined in the present application.

In some embodiments, ring A is selected from the group consisting of phenyl, thienyl and pyridinyl; the other variables are as defined in the present application.

In some embodiments, ring A is selected from the group consisting of phenyl,

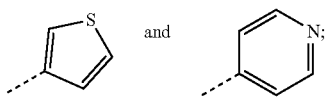

the other variables are as defined in the present application.

In some embodiments of the present application, ring A is selected from the group consisting of phenyl and pyridinyl; the other variables are as defined in the present application.

In some embodiments of the present application, $R_1$ is selected from the group consisting of H, F, Cl, Br, I, CN, COOH, $NH_2$, $C_{1-3}$ alkyl and $C_{1-3}$ heteroalkyl, the $C_{1-3}$ alkyl and $C_{1-3}$ heteroalkyl being optionally substituted with 1, 2 or 3 $R_a$; the other variables are as defined in the present application. In some embodiments of the present application, $R_1$ is selected from the group consisting of H, F, Cl, Br, I, CN, COOH, $NH_2$, Me, Et, $CF_3$, $CHF_2$, $CH_2F$, —$NHCH_3$ and —$N(CH_3)_2$; the other variables are as defined in the present application.

In some embodiments of the present application, $R_1$ is selected from the group consisting of H, F, Cl, Br, I and $C_{1-6}$ alkyl; the other variables are as defined in the present application.

In some embodiments of the present application, $R_1$ is selected from the group consisting of H, F, Cl, Br, I and $C_{1-3}$ alkyl; the other variables are as defined in the present application.

In some embodiments of the present application, $R_1$ is selected from the group consisting of H, Cl, Br, I and Me; the other variables are as defined in the present application.

In some embodiments of the present application, $R_2$ is selected from the group consisting of $C_{1-3}$ alkyl and $C_{1-3}$ heteroalkyl, the $C_{1-3}$ alkyl and $C_{1-3}$ heteroalkyl being optionally substituted with 1, 2 or 3 $R_b$; the other variables are as defined in the present application. In some embodiments of the present application, $R_2$ is selected from the group consisting of $CF_3$, $CH_2CF_3$, $CHF_2$, $CH_2F$, —$NHCH_3$ and —$N(CH_3)_2$; the other variables are as defined in the present application.

In some embodiments of the present application, $R_2$ is $C_{1-6}$ alkyl, the $C_{1-6}$ alkyl being optionally substituted with 1, 2 or 3 $R_b$; the other variables are as defined in the present application.

In some embodiments of the present application, $R_2$ is $C_{1-6}$ alkyl, the $C_{1-6}$ alkyl being optionally substituted with 1, 2 or 3 $R_b$, wherein $R_b$ is selected from the group consisting of F, Cl, Br and I; the other variables are as defined in the present application.

In some embodiments of the present application, $R_2$ is $C_{1-3}$ alkyl, the $C_{1-3}$ alkyl being optionally substituted with 1, 2 or 3 $R_b$, wherein $R_b$ is F; the other variables are as defined in the present application.

In some embodiments of the present application, $R_2$ is ethyl, the ethyl being optionally substituted with 3 $R_b$, wherein $R_b$ is F; the other variables are as defined in the present application.

In some embodiments of the present application, $R_2$ is selected from the group consisting of ethyl and $CH_2CF_3$; the other variables are as defined in the present application.

In some embodiments of the present application, $R_3$ is selected from the group consisting of H and $C_{1-6}$ alkyl; the other variables are as defined in the present application.

In some embodiments of the present application, $R_3$ is selected from the group consisting of H and $C_{1-3}$ alkyl; the other variables are as defined in the present application.

In some embodiments of the present application, $R_3$ is selected from the group consisting of H and methyl; the other variables are as defined in the present application.

In some embodiments of the present application, $R_3$ is H; the other variables are as defined in the present application.

In some embodiments of the present application, $R_4$ is selected from the group consisting of COOH, $NH_2$, $C_{1-6}$ alkyl, —NH—$C_{1-6}$ alkyl, —N($C_{1-6}$ alkyl)$_2$, —C(=O)—

O—$C_{1-6}$ alkyl, —C(=O)—S—$C_{1-6}$ alkyl, $C_{3-6}$ cycloalkyl, 3-6 membered heterocycloalkyl and phenyl, the $C_{1-6}$ alkyl, —NH—$C_{1-6}$ alkyl, —N($C_{1-6}$ alkyl)$_2$, —C(=O)—O—$C_{1-6}$ alkyl, —C(=O)—S—$C_{1-6}$ alkyl, $C_{3-6}$ cycloalkyl, 3-6 membered heterocycloalkyl and phenyl being optionally substituted with 1, 2 or 3 $R_d$; the other variables are as defined in the present application. In some embodiments of the present application, the above-mentioned $R_4$ is selected from the group consisting of COOH, NH$_2$, $C_{1-3}$ alkyl, —NH—$C_{1-3}$ alkyl, —N($C_{1-3}$ alkyl)$_2$, —C(=O)—O—$C_{1-3}$ alkyl, —C(=O)—S—$C_{1-3}$ alkyl, cyclopropyl, cyclopentyl, cyclohexyl, azetidinyl and phenyl, the $C_{1-3}$ alkyl, —NH—$C_{1-3}$ alkyl, —N($C_{1-3}$ alkyl)$_2$, —C(=O)—O—$C_{1-3}$ alkyl, —C(=O)—S—$C_{1-3}$ alkyl, cyclopropyl, cyclopentyl, cyclohexyl, azetidinyl and phenyl being optionally substituted with 1, 2 or 3 $R_d$; the other variables are as defined in the present application.

In some embodiments of the present application, $R_4$ is selected from the group consisting of —NH—$C_{1-6}$ alkyl, —N($C_{1-6}$ alkyl)$_2$ and 3-6 membered heterocycloalkyl, the —NH—$C_{1-6}$ alkyl, —N($C_{1-6}$ alkyl)$_2$ and 3-6 membered heterocycloalkyl being optionally substituted with 1, 2 or 3 $R_d$; the other variables are as defined in the present application.

In some embodiments of the present application, $R_4$ is selected from the group consisting of —NH—$C_{1-3}$ alkyl, —N($C_{1-3}$ alkyl)$_2$ and 4-membered heterocycloalkyl, the —NH—$C_{1-3}$ alkyl, —N($C_{1-3}$ alkyl)$_2$ and 4-membered heterocycloalkyl groups being optionally substituted with 1, 2 or 3 $R_d$; the other variables are as defined in the present application.

In some embodiments of the present application, $R_4$ is selected from the group consisting of —NH—$C_{1-3}$ alkyl, —N($C_{1-3}$ alkyl)$_2$ and

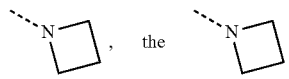

the being optionally substituted with 1, 2 or 3 $R_d$; the other variables are as defined in the present application.

In some embodiments of the present application, $R_4$ is selected from the group consisting of —NH—$C_{1-3}$ alkyl, —N($C_{1-3}$ alkyl)$_2$ and

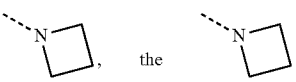

being optionally substituted with 1, 2 or 3 $R_d$, wherein $R_d$ is selected from the group consisting of CF$_3$, CHF$_2$ and CH$_2$F; the other variables are as defined in the present application.

In some embodiments of the present application, $R_4$ is selected from the group consisting of

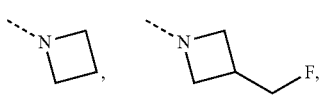

—NHCH$_3$ and —N(CH$_3$)$_2$; the other variables are as defined in the present application.

In some embodiments of the present application, $R_5$ is selected from the group consisting of H, $C_{1-3}$ alkyl and $C_{1-3}$ heteroalkyl, the $C_{1-3}$ alkyl and $C_{1-3}$ heteroalkyl being optionally substituted with 1, 2 or 3 $R_e$; the other variables are as defined in the present application.

In some embodiments of the present application, $R_5$ is H; the other variables are as defined in the present application.

In some embodiments of the present application, $R_6$, $R_7$, $R_8$ and $R_9$ are H; the other variables are as defined in the present application.

In some embodiments of the present application, $R_{10}$, $R_{11}$ and $R_{12}$ are each independently selected from the group consisting of H, F, Cl, Br, I, CN, NO$_2$, OH, COOH, NH$_2$, $C_{1-3}$ alkyl and $C_{1-3}$ heteroalkyl, the $C_{1-3}$ alkyl and $C_{1-3}$ heteroalkyl being optionally substituted with 1, 2 or 3 $R_g$; the other variables are as defined in the present application.

In some embodiments of the present application, $R_{10}$, $R_{11}$ and $R_{12}$ are each independently selected from the group consisting of H, F, Cl, Br, I, CN, NO$_2$, OH, COOH, NH$_2$, Me, Et, CF$_3$, OMe, CHF$_2$, CH$_2$F, NHCH$_3$ and N(CH$_3$)$_2$; the other variables are as defined in the present application.

In some embodiments of the present application, $R_{10}$, $R_{11}$ and $R_{12}$ are each independently selected from the group consisting of H, F, Cl, Br, I, CN, $C_{1-6}$ alkyl and $C_{1-6}$ heteroalkyl, the $C_{1-6}$ alkyl and $C_{1-6}$ heteroalkyl being optionally substituted with 1, 2 or 3 $R_g$; the other variables are as defined in the present application.

In some embodiments of the present application, $R_{10}$, $R_{11}$ and $R_{12}$ are each independently selected from the group consisting of H, F, Cl, Br, I, CN, $C_{1-3}$ alkyl and $C_{1-3}$ heteroalkyl.

In some embodiments of the present application, $R_{10}$, $R_{11}$ and $R_{12}$ are each independently selected from the group consisting of H, F, Cl, Br, I, CN, Me and OMe; the other variables are as defined in the present application.

In some embodiments of the present application, X is NH; the other variables are as defined in the present application.

In some embodiments of the present application, Y is selected from the group consisting of N and CH; the other variables are as defined in the present application.

In some embodiments of the present application, $Y_1$ is N and $Y_2$ is CH or CF; the other variables are as defined in the present application.

In some embodiments of the present application, $Y_1$ is CH and $Y_2$ is CH; the other variables are as defined in the present application.

In some embodiments of the present application, the structural unit

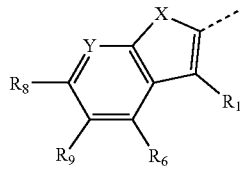

is selected from the group consisting of

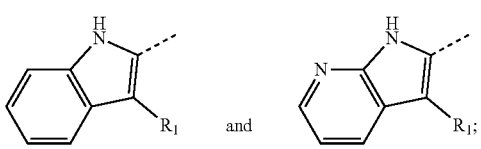

the other variables are as defined in the present application.

In some embodiments of the present application, the structural unit

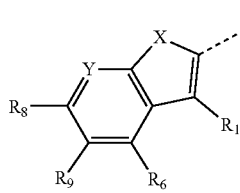

is selected from the group consisting of

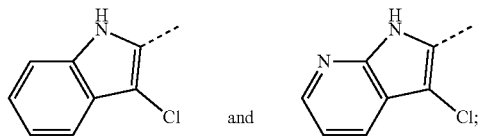

the other variables are as defined in the present application.

In some embodiments of the present application, the structural unit

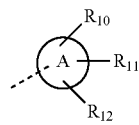

is selected from the group consisting of

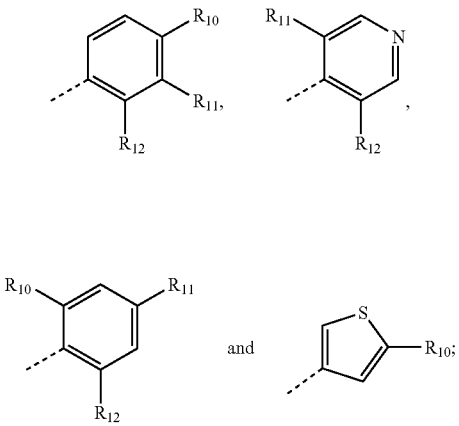

the other variables are as defined in the present application.

In some embodiments of the present application, the structural unit

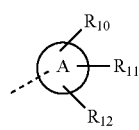

is selected from the group consisting of

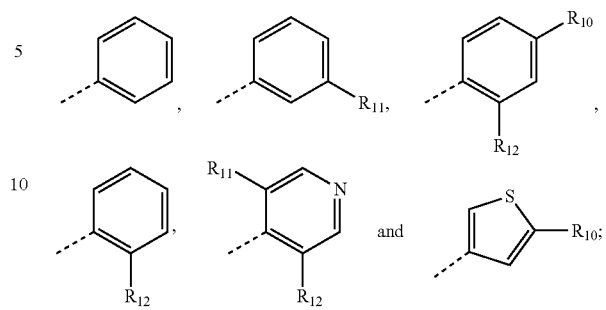

the other variables are as defined herein.

In some embodiments of the present application, the structural unit

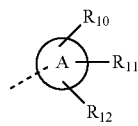

is selected from the group consisting of

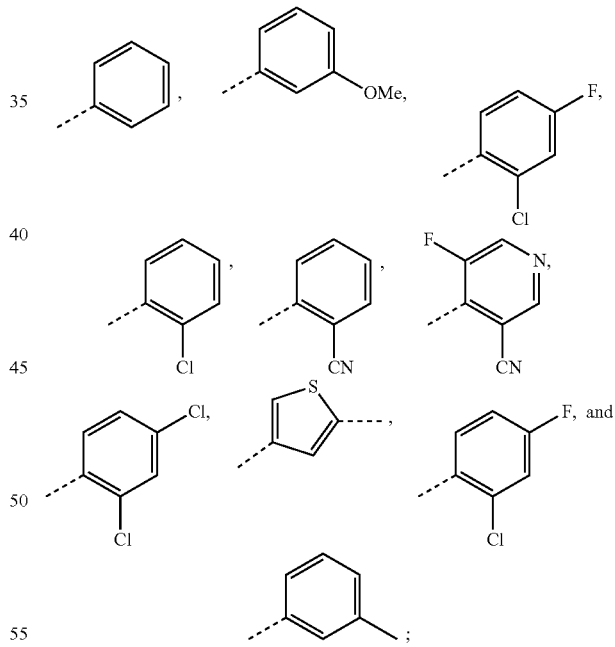

the other variables are as defined in the present application.

In some embodiments of the present application, $R_{13}$ is H,

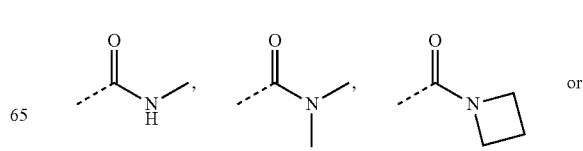

or

-continued

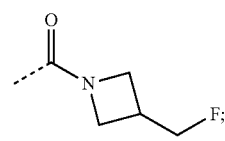

the other variables are as defined in the present application.

In some embodiments of the present application, $R_{13}$ is H,

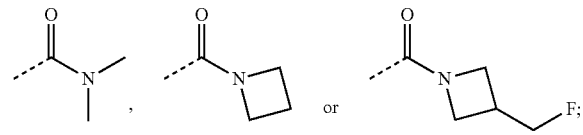

the other variables are as defined in the present application.

In some embodiments of the present application, the structural unit

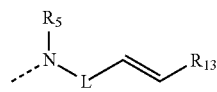

is selected from the group consisting of

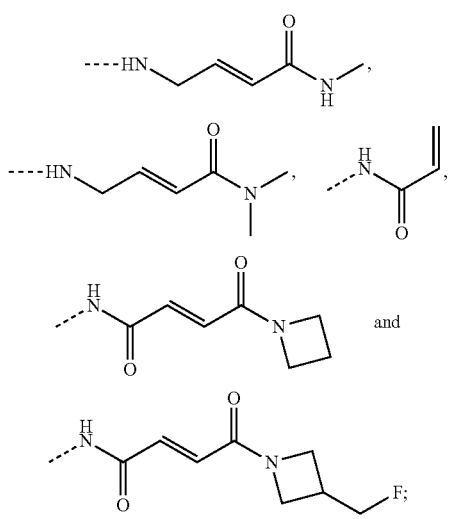

the other variables are defined in the present application.

In some embodiments of the present application, the structural unit

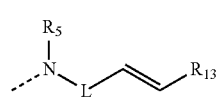

is selected from the group consisting of

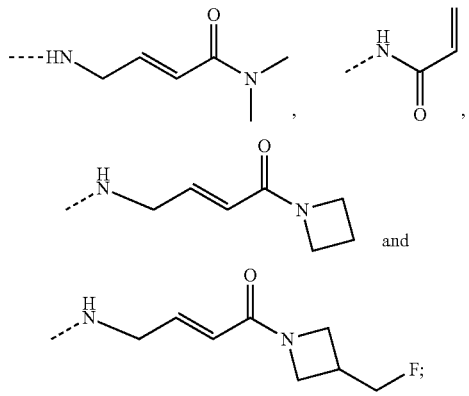

the other variables are as defined in the present application.

In some embodiments of the present application, provided is the compound, the isomer thereof or the pharmaceutically acceptable salt thereof, selected from the group consisting of:

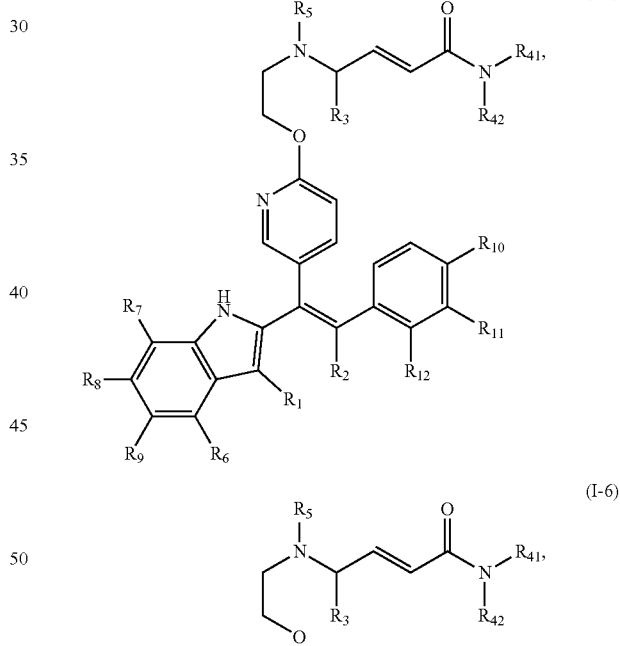

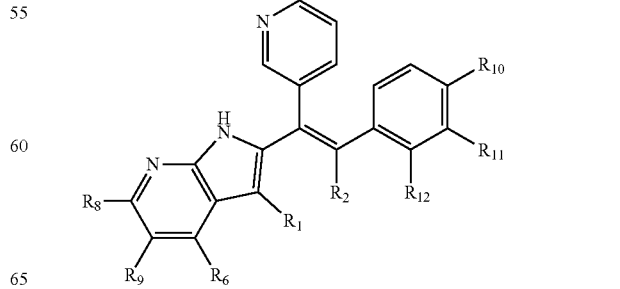

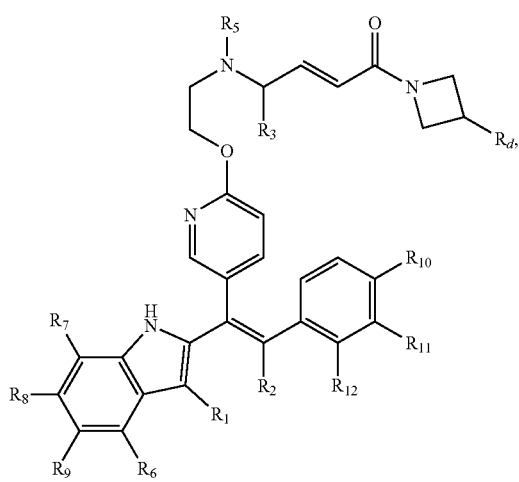
(II-1)

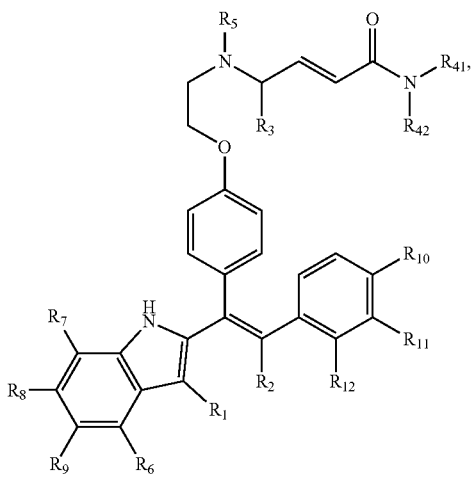
(II-2)

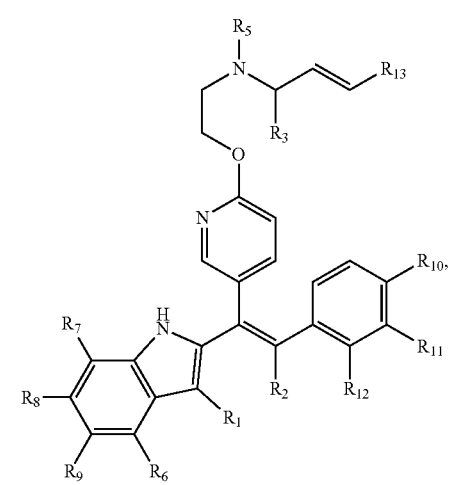
(II-3)

wherein, $R_1$, $R_2$, $R_3$, $R_5$, $R_6$, $R_7$, $R_8$, $R_9$, $R_{10}$, $R_{11}$, $R_{12}$ and $R_{13}$ are as defined in the present application;

$R_{41}$ and $R_{42}$ are each independently selected from H and $C_{1-6}$ alkyl, the $C_{1-6}$ alkyl being optionally substituted with 1, 2 or 3 $R_d$; $R_d$ is as defined in the present application.

In some embodiments of the present application, $R_{41}$ and $R_{42}$ are each independently selected from the group consisting of H and $C_{1-3}$ alkyl; the other variables are as defined in the present application.

In some embodiments of the present application, $R_{41}$ and $R_{42}$ are each independently selected from the group consisting of H and methyl; the other variables are as defined in the present application.

In some embodiments of the present application, $R_{41}$ is H, and $R_{42}$ is methyl; the other variables are as defined in the present application.

In some embodiments of the present application, provided is the compound, the isomer thereof or the pharmaceutically acceptable salt thereof, selected from the group consisting of:

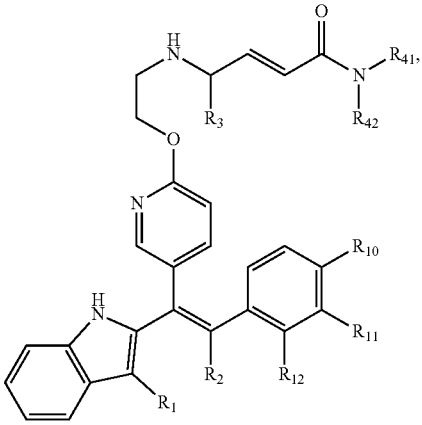
(I-31)

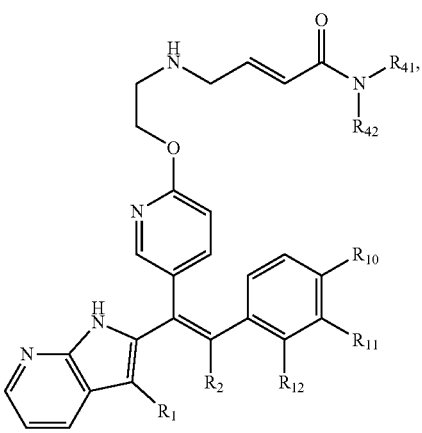
(I-61)

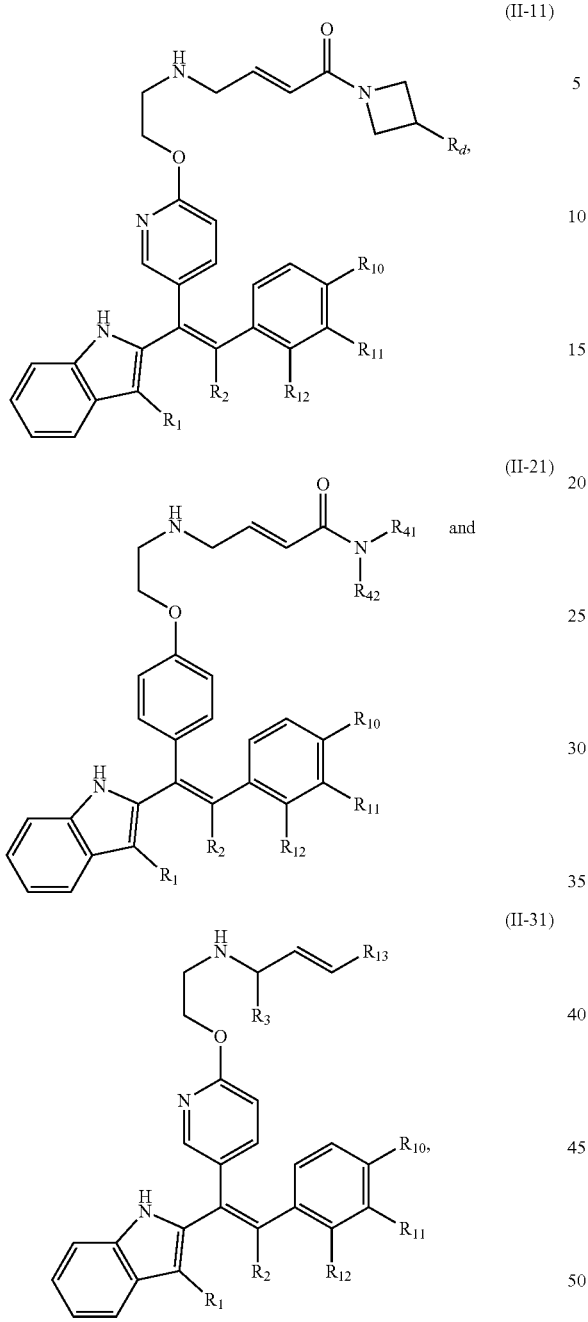

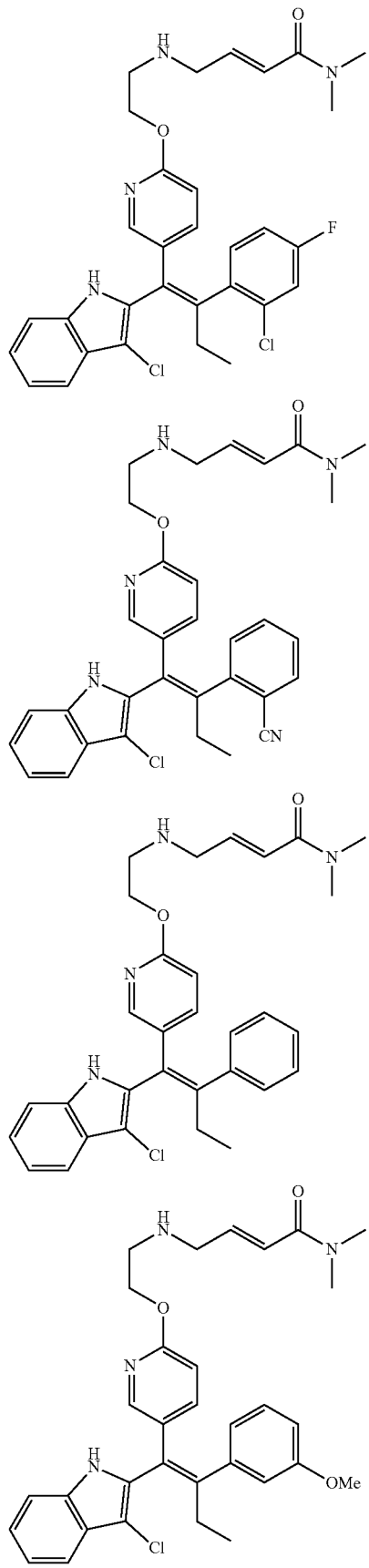

wherein, $R_1$ is selected from the group consisting of H, Cl, Br, I and Me, $R_2$ is selected from the group consisting of ethyl and $CH_2CF_3$, $R_3$ is selected from the group consisting of H and methyl, and $R_{10}$, $R_{11}$, $R_{12}$, $R_{13}$, $R_d$, $R_{41}$ and $R_{42}$ are as defined in the present application.

The present application further provides a compound of the following formulae, an isomer thereof or a pharmaceutically acceptable salt thereof:

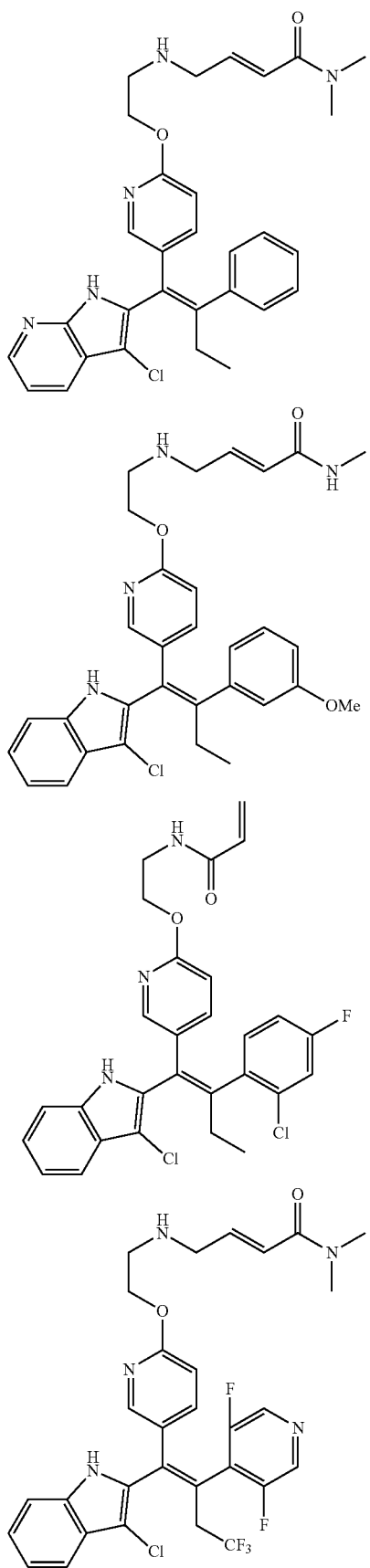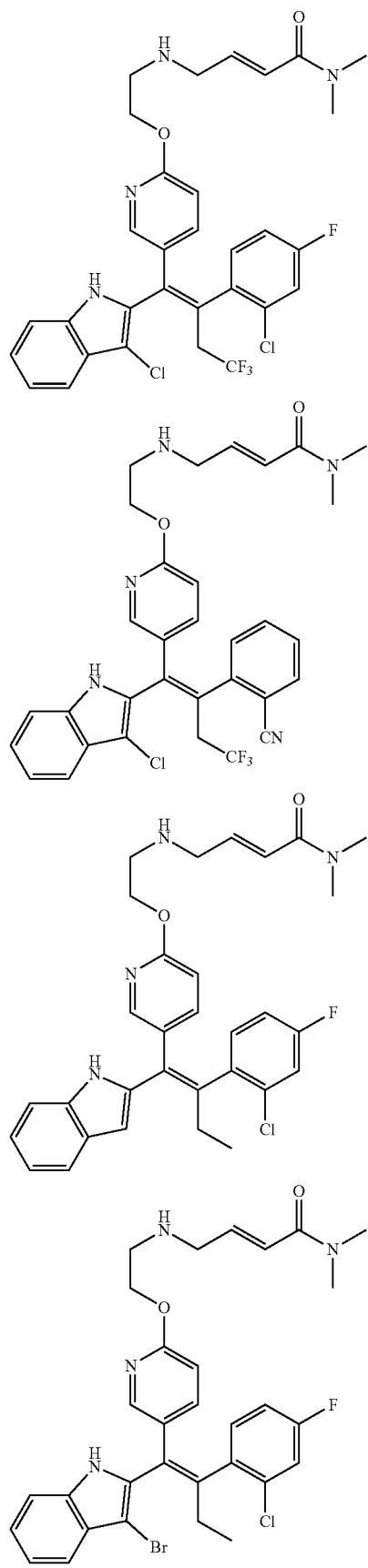

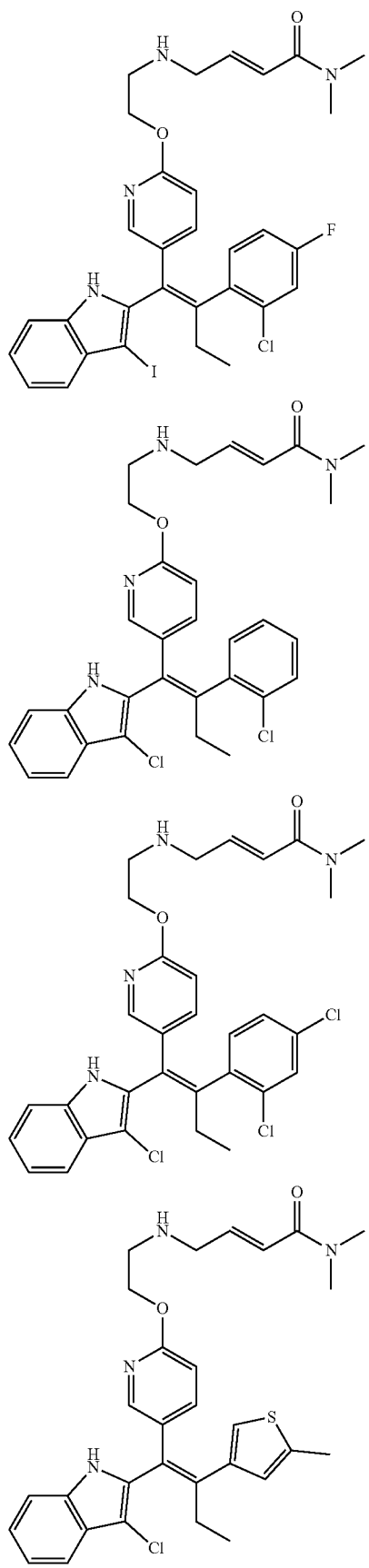
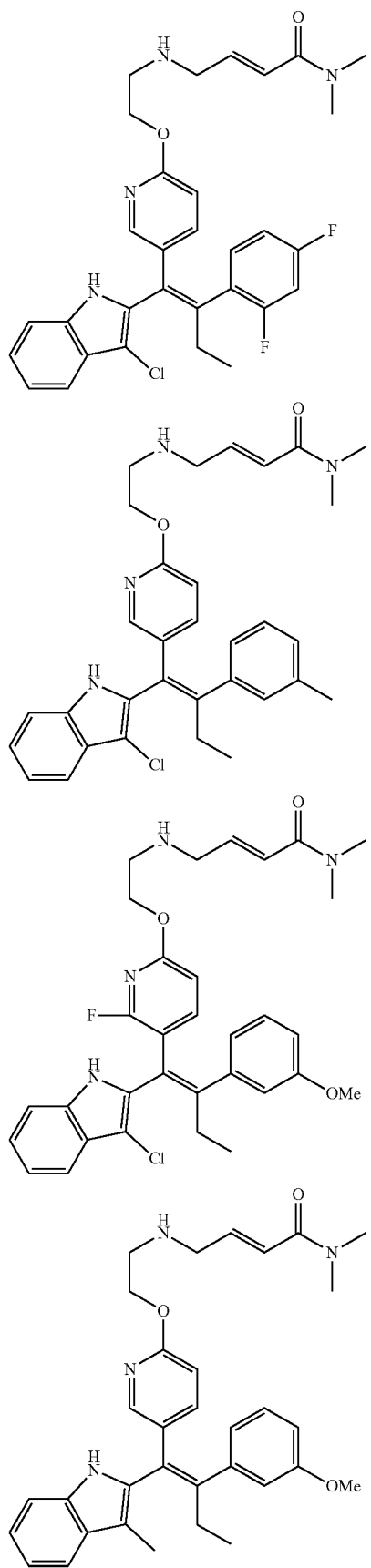

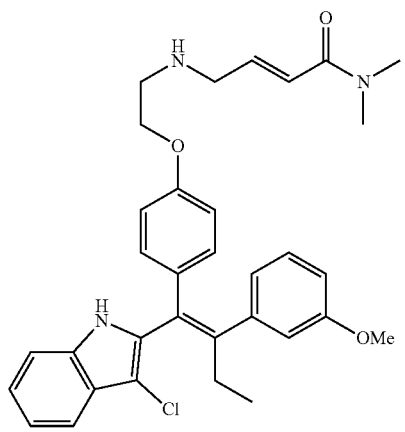
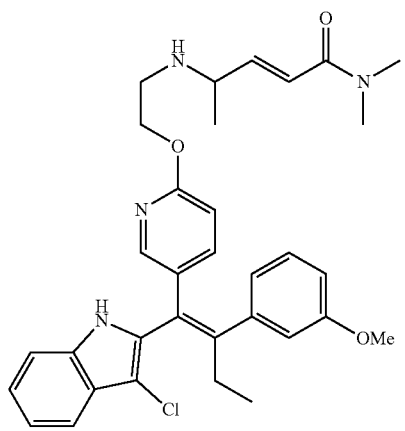
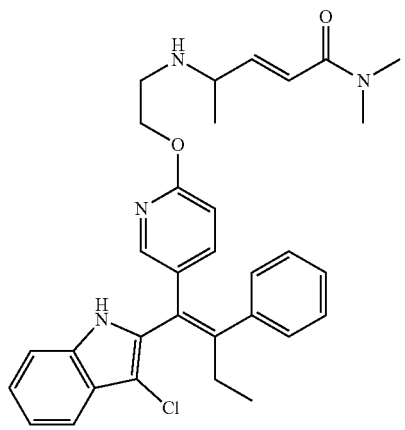
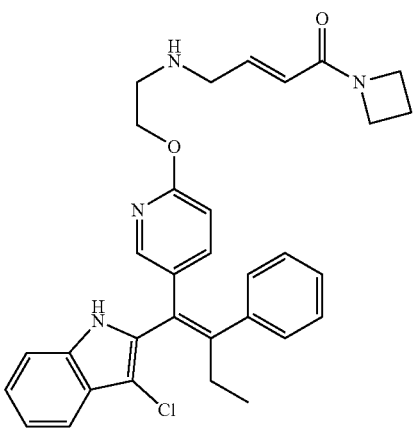
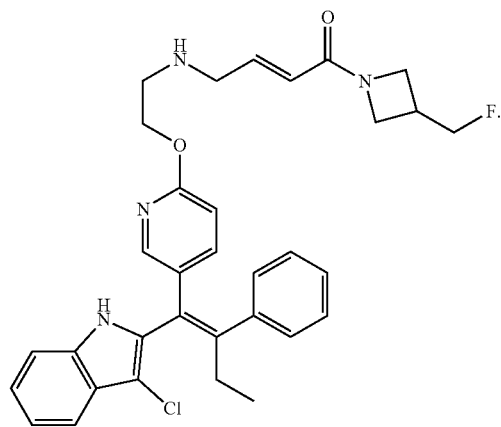 [SMILES: CC/C(=C(/c1ccc(OCCNC/C=C/C(=O)N2CC(CF)C2)nc1)c1[nH]c2ccccc2c1Cl)c1ccccc1]
The present application further provides a compound of the following formulae, an isomer thereof or a pharmaceutically acceptable salt thereof:
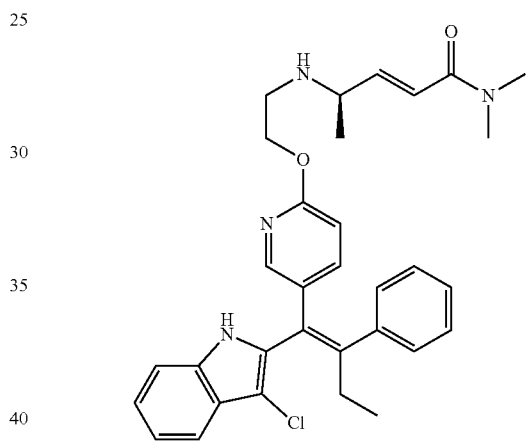
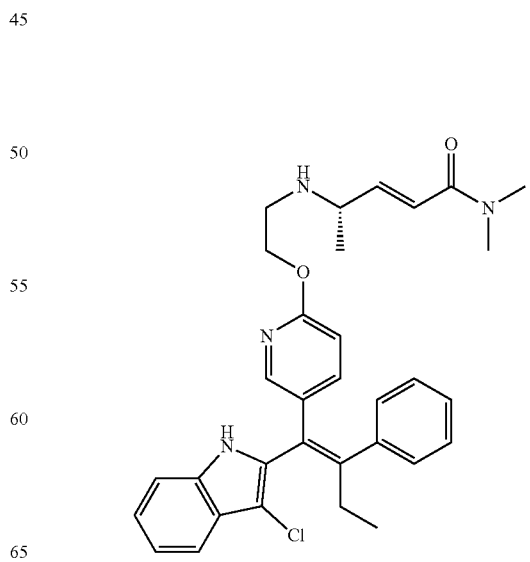

-continued

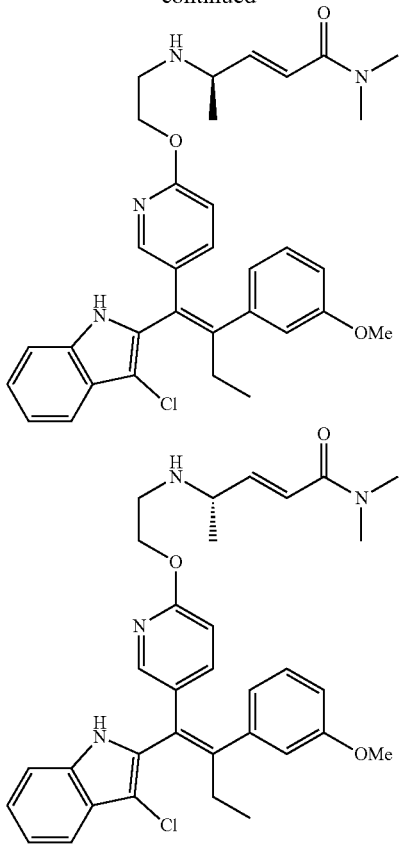

The present application provides a compound of formula (I'), an isomer thereof or a pharmaceutically acceptable salt thereof, wherein, ⌇ is a single bond or double bond;
X is selected from the group consisting of NH, O and S;
Y is selected from the group consisting of N and $CR_7$;
$Y_1$ is CH, and $Y_2$ is N;
or, $Y_1$ is N, and $Y_2$ is CH;

ring A is selected from the group consisting of $C_{6-10}$ aryl and 5-10 membered heteroaryl;

$R_1$ is selected from the group consisting of H, halogen, CN, COOH, $NH_2$, $C_{1-6}$ alkyl, $C_{1-6}$ heteroalkyl, $C_{3-6}$ cycloalkyl and 3-6 membered heterocycloalkyl, the $C_{1-6}$ alkyl, $C_{1-6}$ heteroalkyl, $C_{3-6}$ cycloalkyl and 3-6 membered heterocycloalkyl being optionally substituted with 1, 2 or 3 $R_a$;

$R_2$ is selected from the group consisting of $C_{1-6}$ alkyl, $C_{1-6}$ heteroalkyl, $C_{3-6}$ cycloalkyl and 3-6 membered heterocycloalkyl, the $C_{1-6}$ alkyl, $C_{1-6}$ heteroalkyl, $C_{3-6}$ cycloalkyl and 3-6 membered heterocycloalkyl being optionally substituted with 1, 2 or 3 $R_b$;

$R_3$ is selected from the group consisting of H, halogen, CN, $NO_2$, OH, COOH, $NH_2$, $C_{1-6}$ alkyl, $C_{1-6}$ heteroalkyl, $C_{3-6}$ cycloalkyl and 3-6 membered heterocycloalkyl, the $C_{1-6}$ alkyl, $C_{1-6}$ heteroalkyl, $C_{3-6}$ cycloalkyl and 3-6 membered heterocycloalkyl being optionally substituted with 1, 2 or 3 $R_c$;

$R_4$ is selected from the group consisting of COOH, $NH_2$, $C_{1-6}$ alkyl, $C_{1-6}$ heteroalkyl, $C_{3-6}$ cycloalkyl, 3-6 membered heterocycloalkyl, phenyl and 5-6 membered heteroaryl, the $C_{1-6}$ alkyl, $C_{1-6}$ heteroalkyl, $C_{3-6}$ cycloalkyl, 3-6 membered heterocycloalkyl, phenyl and 5-6 membered heteroaryl being optionally substituted with 1, 2 or 3 $R_d$;

$R_5$ is selected from the group consisting of H, $C_{1-6}$ alkyl, $C_{1-6}$ heteroalkyl, $C_{3-6}$ cycloalkyl and 3-6 membered heterocycloalkyl, the $C_{1-6}$ alkyl, $C_{1-6}$ heteroalkyl, $C_{3-6}$ cycloalkyl and 3-6 membered heterocycloalkyl being optionally substituted with 1, 2 or 3 $R_e$;

$R_6$, $R_7$, $R_8$ and $R_9$ are each independently selected from the group consisting of H, halogen, CN, $NO_2$, OH, COOH, $NH_2$, $C_{1-6}$ alkyl, $C_{1-6}$ heteroalkyl, $C_{3-6}$ cycloalkyl and 3-6 membered heterocycloalkyl, the $C_{1-6}$ alkyl, $C_{1-6}$ heteroalkyl, $C_{3-6}$ cycloalkyl and 3-6 membered heterocycloalkyl being optionally substituted with 1, 2 or 3 $R_f$;

$R_{10}$, $R_{11}$ and $R_{12}$ are each independently selected from the group consisting of H, halogen, CN, $NO_2$, OH, COOH, $NH_2$, $C_{1-6}$ alkyl, $C_{1-6}$ heteroalkyl, $C_{3-6}$ cycloalkyl and 3-6 membered heterocycloalkyl, the $C_{1-6}$ alkyl, $C_{1-6}$ heteroalkyl, $C_{3-6}$ cycloalkyl and 3-6 membered heterocycloalkyl being optionally substituted with 1, 2 or 3 $R_g$;

$R_a$, $R_b$, $R_c$, $R_d$, $R_e$, $R_f$ and $R_g$ are each independently selected from the group consisting of H, F, Cl, Br, I, OH, CN, $NH_2$, COOH, $C(=O)NH_2$, $C_{1-3}$ alkyl, $C_{1-3}$ heteroalkyl, $C_{3-6}$ cycloalkyl, 3-6 membered heterocycloalkyl and $C_{3-6}$ cycloalkyl-$C_{1-3}$ alkyl-, the $C_{1-8}$ alkyl, $C_{1-8}$ heteroalkyl, $C_{3-6}$ cycloalkyl, 3-6 membered heterocycloalkyl and $C_{3-6}$ cycloalkyl-$C_{1-3}$ alkyl- being optionally substituted with 1, 2 or 3 R;

R is independently selected from the group consisting of F, Cl, Br, I, OH, CN, $NH_2$, COOH, Me, Et, $CF_3$, $CHF_2$, $CH_2F$, $NHCH_3$, and $N(CH_3)_2$;

the $C_{1-6}$ heteroalkyl, 3-6 membered heterocycloalkyl and 5-6 membered heteroaryl each comprise 1, 2, 3 or 4 heteroatoms or heteroatom groups each independently selected from the group consisting of —NH—, —O—, —S—, —O—N=, —C(=O)—O—, —C(=O)—S—, —C(=O)—, —C(=S)—, —S(=O)—, —S(=O)$_2$— and N.

In some embodiments of the present application, $R_a$, $R_b$, $R_c$, $R_d$, $R_e$, $R_f$ and $R_g$ in the formula (I') are each independently selected from the group consisting of H, F, Cl, Br, I, OH, CN, $NH_2$, COOH, $C(=O)NH_2$, $C_{1-6}$ alkyl, $C_{1-6}$ heteroalkyl and cyclopropyl, the $C_{1-6}$ alkyl, $C_{1-6}$ heteroalkyl and cyclopropyl being optionally substituted with 1, 2 or 3 R.

In some embodiments of the present application, $R_a$, $R_b$, $R_c$, $R_d$, $R_e$, $R_f$ and $R_g$ in the formula (I') are each independently selected from the group consisting of H, F, Cl, Br, I, OH, CN, $NH_2$, COOH, $C(=O)NH_2$, Me, Et, $CF_3$, $CHF_2$, $CH_2F$, $NHCH_3$ and $N(CH_3)_2$.

In some embodiments of the present application, $R_1$ in the formula (I') is selected from the group consisting of H, F, Cl, Br, I, CN, COOH, $NH_2$, $C_{1-3}$ alkyl and $C_{1-3}$ heteroalkyl, the $C_{1-3}$ alkyl and $C_{1-3}$ heteroalkyl being optionally substituted with 1, 2 or 3 $R_a$.

In some embodiments of the present application, $R_1$ in the formula (I') is selected from the group consisting of H, F, Cl, Br, I, CN, COOH, $NH_2$, Me, Et, $CF_3$, $CHF_2$, $CH_2F$, —$NHCH_3$ and —$N(CH_3)_2$.

In some embodiments of the present application, $R_2$ in the formula (I') is selected from the group consisting of $C_{1-3}$ alkyl and $C_{1-3}$ heteroalkyl, the $C_{1-3}$ alkyl and $C_{1-3}$ heteroalkyl being optionally substituted with 1, 2 or 3 Rb.

In some embodiments of the present application, $R_2$ in the formula (I') is selected from the group consisting of Me, Et, $CF_3$, $CH_2CF_3$, $CHF_2$, $CH_2F$, —$NHCH_3$ and —$N(CH_3)_2$.

In some embodiments of the present application, $R_3$ in the formula (I') is H.

In some embodiments of the present application, $R_4$ in the formula (I') is selected from the group consisting of COOH, $NH_2$, $C_{1-6}$ alkyl, —NH—$C_{1-6}$ alkyl, —N($C_{1-6}$ alkyl)$_2$, —C(=O)—O—$C_{1-6}$ alkyl, —C(=O)—S—$C_{1-6}$ alkyl, $C_{3-6}$ cycloalkyl, 3-6 membered heterocycloalkyl and phenyl, the $C_{1-6}$ alkyl, —NH—$C_{1-6}$ alkyl, —N($C_{1-6}$ alkyl)$_2$, —C(=O)—O—$C_{1-6}$ alkyl, —C(=O)—S—$C_{1-6}$ alkyl, $C_{3-6}$ cycloalkyl, 3-6 membered heterocycloalkyl and phenyl being optionally substituted with 1, 2 or 3 $R_d$.

In some embodiments of the present application, $R_4$ in the formula (I') is selected from the group consisting of COOH, $NH_2$, $C_{1-6}$ alkyl, —NH—$C_{1-6}$ alkyl, —N($C_{1-6}$ alkyl)$_2$, —C(=O)—O—$C_{1-6}$ alkyl, —C(=O)—S—$C_{1-6}$ alkyl, cyclopropyl, cyclopentyl, cyclohexyl, azetidinyl and phenyl.

In some embodiments of the present application, $R_4$ in the formula (I') is selected from the group consisting of —$NHCH_3$ and —$N(CH_3)_2$.

In some embodiments of the present application, $R_5$ in the formula (I') is selected from the group consisting of H, $C_{1-3}$ alkyl and $C_{1-3}$ heteroalkyl, the $C_{1-3}$ alkyl and $C_{1-3}$ heteroalkyl being optionally substituted with 1, 2 or 3 $R_e$.

In some embodiments of the present application, $R_5$ in the formula (I') is H.

In some embodiments of the present application, $R_6$, $R_7$, $R_8$ and $R_9$ in the formula (I') are H.

In some embodiments of the present application, $R_{10}$, $R_{11}$ and $R_{12}$ in the formula (I') are each independently selected from the group consisting of H, F, Cl, Br, I, CN, $NO_2$, OH, COOH, $NH_2$, $C_{1-3}$ alkyl and $C_{1-3}$ heteroalkyl, the $C_{1-3}$ alkyl and $C_{1-3}$ heteroalkyl being optionally substituted with 1, 2 or 3 $R_g$.

In some embodiments of the present application, $R_{10}$, $R_{11}$ and $R_{12}$ in the formula (I') are each independently selected from the group consisting of H, F, Cl, Br, I, CN, $NO_2$, OH, COOH, $NH_2$, Me, Et, $CF_3$, OMe, $CHF_2$, $CH_2F$, $NHCH_3$ and $N(CH_3)_2$.

In some embodiments of the present application, ring A in the formula (I') is phenyl.

In some embodiments of the present application, the structural unit

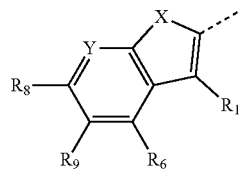

in the formula (I') is selected from the group consisting of

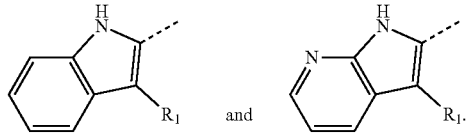

In some embodiments of the present application, the structural unit

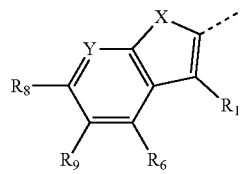

in the formula (I') is selected from the group consisting of

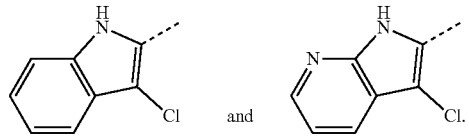

In some embodiments of the present application, the structural unit

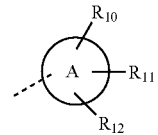

in the formula (I') is selected from the group consisting of

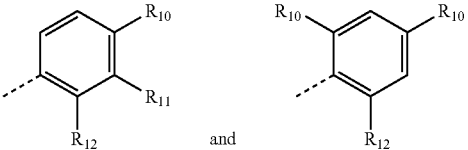

In some embodiments of the present application, the structural unit

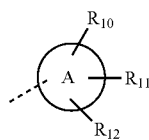

in the formula (I') is selected from the group consisting of

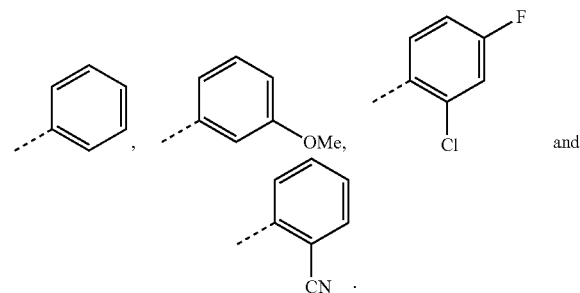

In some embodiments of the present application, $R_a$, $R_b$, $R_c$, $R_d$, $R_e$, $R_f$ and $R_g$ in the formula (I') are each independently selected from the group consisting of H, F, Cl, Br, I, OH, CN, $NH_2$, COOH, C(=O)$NH_2$, $C_{1-6}$ alkyl, $C_{1-6}$ heteroalkyl and cyclopropyl, the $C_{1-6}$ alkyl, $C_{1-6}$ heteroalkyl and cyclopropyl being optionally substituted with 1, 2 or 3 R; the other variables are as defined in the present application.

In some embodiments of the present application, $R_a$, $R_b$, $R_c$, $R_d$, $R_e$, $R_f$ and $R_g$ in the formula (I') are each independently selected from the group consisting of H, F, Cl, Br, I, OH, CN, $NH_2$, COOH, C(=O)$NH_2$, Me, Et, $CF_3$, $CHF_2$, $CH_2F$, $NHCH_3$ and $N(CH_3)_2$; the other variables are as defined in the present application.

In some embodiments of the present application, $R_1$ in the formula (I') is selected from the group consisting of H, F, Cl, Br, I, CN, COOH, $NH_2$, $C_{1-3}$ alkyl and $C_{1-3}$ heteroalkyl, the $C_{1-3}$ alkyl and $C_{1-3}$ heteroalkyl being optionally substituted with 1, 2 or 3 $R_a$; the other variables are as defined in the present application.

In some embodiments of the present application, $R_1$ in the formula (I') is selected from the group consisting of H, F, Cl, Br, I, CN, COOH, $NH_2$, Me, Et, $CF_3$, $CHF_2$, $CH_2F$, —$NHCH_3$ and —$N(CH_3)_2$; the other variables are as defined in the present application.

In some embodiments of the present application, $R_2$ in the formula (I') is selected from the group consisting of $C_{1-3}$ alkyl and $C_{1-3}$ heteroalkyl, the $C_{1-3}$ alkyl and $C_{1-3}$ heteroalkyl being optionally substituted with 1, 2 or 3 $R_b$; the other variables are as defined in the present application.

In some embodiments of the present application, $R_2$ in the formula (I') is selected from the group consisting of Me, Et, $CF_3$, $CH_2CF_3$, $CHF_2$, $CH_2F$, —$NHCH_3$ and —$N(CH_3)_2$.

In some embodiments of the present application, $R_3$ in the formula (I') is H; the other variables are as defined in the present application.

In some embodiments of the present application, $R_4$ in the formula (I') is selected from the group consisting of COOH, $NH_2$, $C_{1-6}$ alkyl, —NH—$C_{1-6}$ alkyl, —N($C_{1-6}$ alkyl)$_2$, —C(=O)—O—$C_{1-6}$ alkyl, —C(=O)—S—$C_{1-6}$ alkyl, $C_{3-6}$ cycloalkyl, 3-6 membered heterocycloalkyl and phenyl, the $C_{1-6}$ alkyl, —NH—$C_{1-6}$ alkyl, —N($C_{1-6}$ alkyl)$_2$, —C(=O)—O—$C_{1-6}$ alkyl, —C(=O)—S—$C_{1-6}$ alkyl, $C_{3-6}$ cycloalkyl, 3-6 membered heterocycloalkyl and phenyl being optionally substituted with 1, 2 or 3 $R_d$; the other variables are as defined in the present application.

In some embodiments of the present application, $R_4$ in the formula (I') is selected from the group consisting of COOH, $NH_2$, $C_{1-6}$ alkyl, —NH—$C_{1-6}$ alkyl, —N($C_{1-6}$ alkyl)$_2$, —C(=O)—O—$C_{1-6}$ alkyl, —C(=O)—S—$C_{1-6}$ alkyl, cyclopropyl, cyclopentyl, cyclohexyl, azetidinyl and phenyl; the other variables are as defined in the present application.

In some embodiments of the present application, $R_4$ in the formula (I') is selected from the group consisting of —$NHCH_3$ and —$N(CH_3)_2$; the other variables are as defined in the present application.

In some embodiments of the present application, $R_5$ in the formula (I') is selected from the group consisting of H, $C_{1-3}$ alkyl and $C_{1-3}$ heteroalkyl, the $C_{1-3}$ alkyl and $C_{1-3}$ heteroalkyl being optionally substituted with 1, 2 or 3 $R_e$; the other variables are as defined in the present application.

In some embodiments of the present application, $R_5$ in the formula (I') is H; the other variables are as defined in the present application.

In some embodiments of the present application, $R_6$, $R_7$, $R_8$ and $R_9$ in the formula (I') are H; the other variables are as defined in the present application.

In some embodiments of the present application, $R_{10}$, $R_{11}$ and $R_{12}$ in the formula (I') are each independently selected from the group consisting of H, F, Cl, Br, I, CN, $NO_2$, OH, COOH, $NH_2$, $C_{1-3}$ alkyl and $C_{1-3}$ heteroalkyl, the $C_{1-3}$ alkyl and $C_{1-3}$ heteroalkyl being optionally substituted with 1, 2 or 3 $R_g$; the other variables are as defined in the present application.

In some embodiments of the present application, $R_{10}$, $R_{11}$ and $R_{12}$ in the formula (I') are each independently selected from the group consisting of H, F, Cl, Br, I, CN, $NO_2$, OH, COOH, $NH_2$, Me, Et, $CF_3$, OMe, $CHF_2$, $CH_2F$, $NHCH_3$ and $N(CH_3)_2$; the other variables are as defined in the present application.

In some embodiments of the present application, ring A in the formula (I') is phenyl; the other variables are as defined in the present application.

In some embodiments of the present application, the structural unit

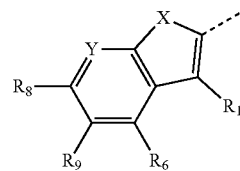

in the formula (I') is selected from the group consisting of

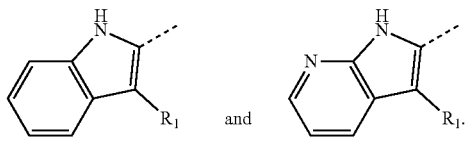

the other variables are as defined in the present application.

In some embodiments of the present application, the structural unit

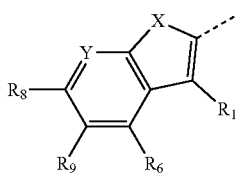

in the formula (I') is selected from the group consisting of

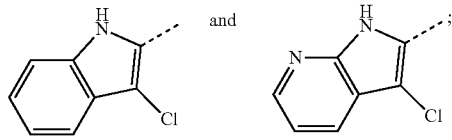

the other variables are as defined in the present application.

In some embodiments of the present application, the structural unit

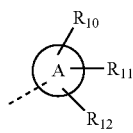

in the formula (I') is selected from the group consisting of

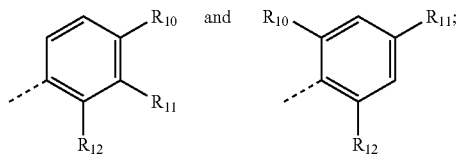

the other variables are as defined in the present application.

In some embodiments of the present application, the structural unit

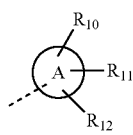

in the formula (I') is selected from the group consisting of

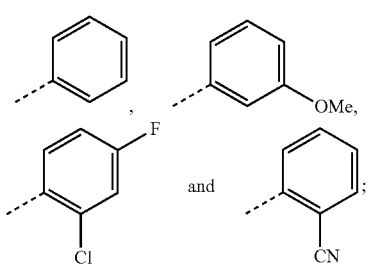

the other variables are as defined in the present application.

In some embodiments of the present application, provided is the compound, the isomer thereof or the pharmaceutically acceptable salt thereof, selected from the group consisting of:

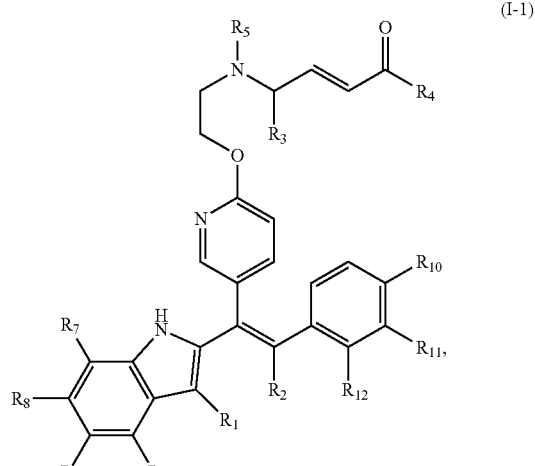
(I-1)

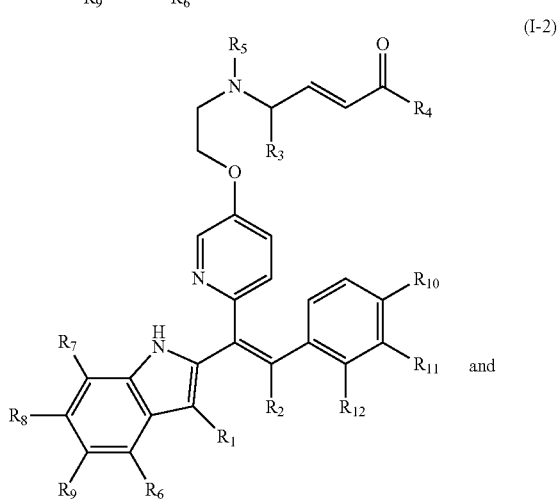
(I-2) and

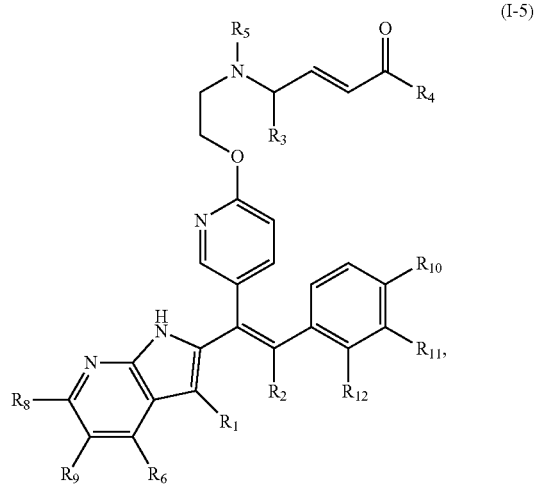
(I-5)

wherein, $R_1$, $R_2$, $R_3$, $R_4$, $R_5$, $R_6$, $R_7$, $R_8$, $R_9$, $R_{10}$, $R_{11}$ and $R_{12}$ are as defined in the present application.

In some embodiments of the present application, provided is the compound, the isomer thereof or the pharmaceutically acceptable salt thereof, selected from the group consisting of:

(I-3)

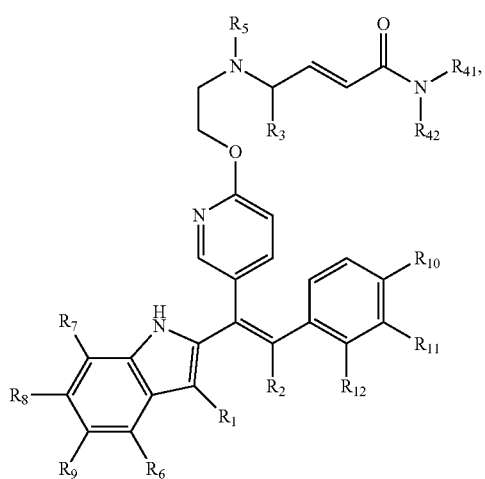

(I-4)

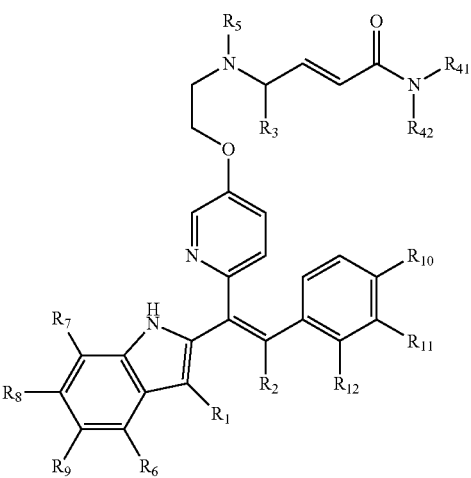 and (I-6)

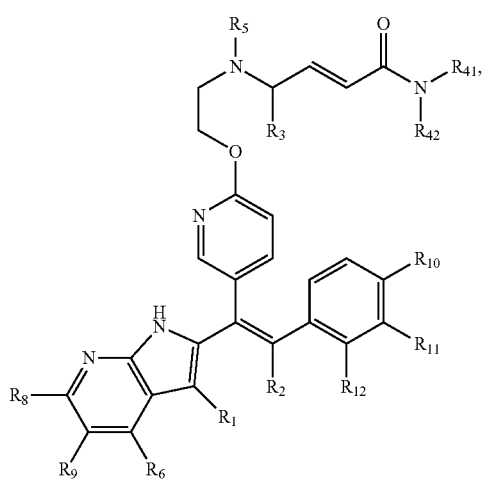

wherein,
R$_1$, R$_2$, R$_3$, R$_5$, R$_6$, R$_7$, R$_8$, R$_9$, R$_{10}$, R$_{11}$ and R$_{12}$ areas defined in the present application,
R$_{41}$ and R$_{42}$ are each independently selected from H and C$_{1-6}$ alkyl, the C$_{1-6}$ alkyl being optionally substituted with 1, 2 or 3 Ra,
R$_d$ is as defined in the present application.

The present application provides a compound of formula (I), an isomer thereof or a pharmaceutically acceptable salt thereof, (I)

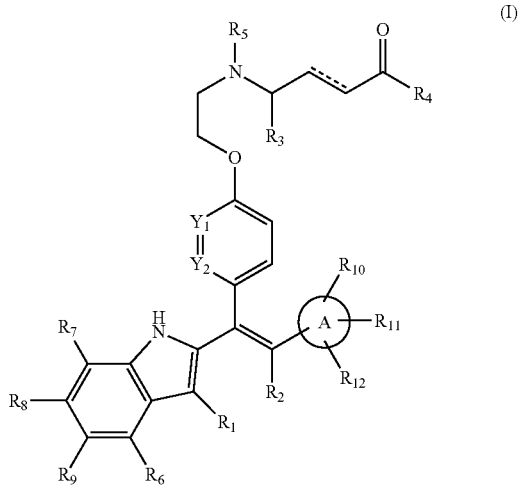

wherein,

⇌ is a single bond or double bond;
X is selected from the group consisting of NH, O and S;
Y$_1$ is CH, and Y$_2$ is N;
or, Y$_1$ is N, and Y$_2$ is CH;
ring A is selected from the group consisting of C$_{6-10}$ aryl and 5-10 membered heteroaryl;
R$_1$ is selected from the group consisting of H, halogen, CN, COOH, NH$_2$, C$_{1-6}$ alkyl, C$_{1-6}$ heteroalkyl, C$_{3-6}$ cycloalkyl and 3-6 membered heterocycloalkyl, the C$_{1-6}$ alkyl, C$_{1-6}$ heteroalkyl, C$_{3-6}$ cycloalkyl and 3-6 membered heterocycloalkyl being optionally substituted with 1, 2 or 3 R$_a$;
R$_2$ is selected from the group consisting of C$_{1-6}$ alkyl, C$_{1-6}$ heteroalkyl, C$_{3-6}$ cycloalkyl and 3-6 membered heterocycloalkyl, the C$_{1-6}$ alkyl, C$_{1-6}$ heteroalkyl, C$_{3-6}$ cycloalkyl and 3-6 membered heterocycloalkyl being optionally substituted with 1, 2 or 3 R$_b$;
R$_3$ is selected from the group consisting of H, halogen, CN, NO$_2$, OH, COOH, NH$_2$, C$_{1-6}$ alkyl, C$_{1-6}$ heteroalkyl, C$_{3-6}$ cycloalkyl and 3-6 membered heterocycloalkyl, the C$_{1-6}$ alkyl, C$_{1-6}$ heteroalkyl, C$_{3-6}$ cycloalkyl and 3-6 membered heterocycloalkyl being optionally substituted with 1, 2 or 3 R$_c$;
R$_4$ is selected from the group consisting of COOH, NH$_2$, C$_{1-6}$ alkyl, C$_{1-6}$ heteroalkyl, C$_{3-6}$ cycloalkyl, 3-6 membered heterocycloalkyl, phenyl and 5-6 membered heteroaryl, the C$_{1-6}$ alkyl, C$_{1-6}$ heteroalkyl, C$_{3-6}$ cycloalkyl, 3-6 membered heterocycloalkyl, phenyl and 5-6 membered heteroaryl being optionally substituted with 1, 2 or 3 R$_d$;
R$_5$ is selected from the group consisting of H, C$_{1-6}$ alkyl, C$_{1-6}$ heteroalkyl, C$_{3-6}$ cycloalkyl and 3-6 membered heteroalkyl, the C$_{1-6}$ alkyl, C$_{1-6}$ heteroalkyl, C$_{3-6}$ cycloalkyl and 3-6 membered heterocycloalkyl being optionally substituted with 1, 2 or 3 $R_e$;

$R_6$, $R_7$, $R_8$ and $R_9$ are each independently selected from the group consisting of H, halogen, CN, $NO_2$, OH, COOH, $NH_2$, $C_{1-6}$ alkyl, $C_{1-6}$ heteroalkyl, $C_{3-6}$ cycloalkyl and 3-6 membered heterocycloalkyl, the $C_{1-6}$ alkyl, $C_{1-6}$ heteroalkyl, $C_{3-6}$ cycloalkyl and 3-6 membered heterocycloalkyl being optionally substituted with 1, 2 or 3 $R_f$;

$R_{10}$, $R_{11}$ and $R_{12}$ are each independently selected from the group consisting of H, halogen, CN, $NO_2$, OH, COOH, $NH_2$, $C_{1-6}$ alkyl, $C_{1-6}$ heteroalkyl, $C_{3-6}$ cycloalkyl and 3-6 membered heterocycloalkyl, the $C_{1-6}$ alkyl, $C_{1-6}$ heteroalkyl, $C_{3-6}$ cycloalkyl and 3-6 membered heterocycloalkyl being optionally substituted with 1, 2 or 3 $R_g$;

$R_a$, $R_b$, $R_c$, $R_d$, $R_e$, $R_f$ and $R_g$ are each independently selected from the group consisting of H, F, Cl, Br, I, OH, CN, $NH_2$, COOH, $C(=O)NH_2$, $C_{1-8}$ alkyl, $C_{1-8}$ heteroalkyl, $C_{3-6}$ cycloalkyl, 3-6 membered heterocycloalkyl and $C_{3-6}$ cycloalkyl-$C_{1-3}$ alkyl-, the $C_{1-8}$ alkyl, $C_{1-8}$ heteroalkyl, $C_{3-6}$ cycloalkyl, 3-6 membered heterocycloalkyl and $C_{3-6}$ cycloalkyl-$C_{1-3}$ alkyl- being optionally substituted with 1, 2 or 3 R; R is independently selected from the group consisting of F, Cl, Br, I, OH, CN, $NH_2$, COOH, Me, Et, $CF_3$, $CHF_2$, $CH_2F$, $NHCH_3$, and $N(CH_3)_2$;

the $C_{1-6}$ heteroalkyl, 3-6 membered heterocycloalkyl and 5-6 membered heteroaryl each comprise 1, 2, 3 or 4 heteroatoms or heteroatom groups each independently selected from the group consisting of —NH—, —O—, —S—, —O—N=, —C(=O)—O—, —C(=O)—S—, —C(=O)—, —C(=S)—, —S(=O)—, —S(=O)$_2$— and N.

In some embodiments of the present application, $R_a$, $R_b$, $R_c$, $R_d$, $R_e$, $R_f$ and $R_g$ in the formula (I) are each independently selected from the group consisting of H, F, Cl, Br, I, OH, CN, $NH_2$, COOH, $C(=O)NH_2$, $C_{1-6}$ alkyl, $C_{1-6}$ heteroalkyl and cyclopropyl, the $C_{1-6}$ alkyl, $C_{1-6}$ heteroalkyl and cyclopropyl being optionally substituted with 1, 2 or 3 R.

In some embodiments of the present application, $R_a$, $R_b$, $R_c$, $R_d$, $R_e$, $R_f$ and $R_g$ in the formula (I) are each independently selected from the group consisting of H, F, Cl, Br, I, OH, CN, $NH_2$, COOH, $C(=O)NH_2$, Me, Et, $CF_3$, $CHF_2$, $CH_2F$, $NHCH_3$ and $N(CH_3)_2$.

In some embodiments of the present application, $R_1$ in the formula (I) is selected from the group consisting of H, F, Cl, Br, I, CN, COOH, $NH_2$, $C_{1-3}$ alkyl and $C_{1-3}$ heteroalkyl, the $C_{1-3}$ alkyl and $C_{1-3}$ heteroalkyl being optionally substituted with 1, 2 or 3 $R_a$.

In some embodiments of the present application, $R_1$ in the formula (I) is selected from the group consisting of H, F, Cl, Br, I, CN, COOH, $NH_2$, Me, Et, $CF_3$, $CHF_2$, $CH_2F$, —$NHCH_3$ and —$N(CH_3)_2$.

In some embodiments of the present application, $R_2$ in the formula (I) is selected from the group consisting of $C_{1-3}$ alkyl and $C_{1-3}$ heteroalkyl, the $C_{1-3}$ alkyl and $C_{1-3}$ heteroalkyl being optionally substituted with 1, 2 or 3 Rb.

In some embodiments of the present application, $R_2$ in the formula (I) is selected from the group consisting of Me, Et, $CF_3$, $CH_2CF_3$, $CHF_2$, $CH_2F$, —$NHCH_3$ and —$N(CH_3)_2$.

In some embodiments of the present application, $R_3$ in the formula (I) is H.

In some embodiments of the present application, $R_4$ in the formula (I) is selected from the group consisting of COOH, $NH_2$, $C_{1-6}$ alkyl, —NH—$C_{1-6}$ alkyl, —N($C_{1-6}$ alkyl)$_2$, —C(=O)—O—$C_{1-6}$ alkyl, —C(=O)—S—$C_{1-6}$ alkyl, $C_{3-6}$ cycloalkyl, 3-6 membered heterocycloalkyl and phenyl, the $C_{1-6}$ alkyl, —NH—$C_{1-6}$ alkyl, —N($C_{1-6}$ alkyl)$_2$, —C(=O)—O—$C_{1-6}$ alkyl, —C(=O)—S—$C_{1-6}$ alkyl, $C_{3-6}$ cycloalkyl, 3-6 membered heterocycloalkyl and phenyl being optionally substituted with 1, 2 or 3 $R_d$.

In some embodiments of the present application, $R_4$ in the formula (I) is selected from the group consisting of COOH, $NH_2$, $C_{1-6}$ alkyl, —NH—$C_{1-6}$ alkyl, —N($C_{1-6}$ alkyl)$_2$, —C(=O)—O—$C_{1-6}$ alkyl, —C(=O)—S—$C_{1-6}$ alkyl, cyclopropyl, cyclopentyl, cyclohexyl, azetidinyl and phenyl.

In some embodiments of the present application, $R_4$ in the formula (I) is selected from the group consisting of —$NHCH_3$ and —$N(CH_3)_2$.

In some embodiments of the present application, $R_5$ in the formula (I) is selected from the group consisting of H, $C_{1-3}$ alkyl and $C_{1-3}$ heteroalkyl, the $C_{1-3}$ alkyl and $C_{1-3}$ heteroalkyl being optionally substituted with 1, 2 or 3 $R_e$.

In some embodiments of the present application, $R_5$ in the formula (I) is H.

In some embodiments of the present application, $R_6$, $R_7$, $R_8$ and $R_9$ in the formula (I) are H.

In some embodiments of the present application, $R_{10}$, $R_{11}$ and $R_{12}$ in the formula (I) are each independently selected from the group consisting of H, F, Cl, Br, I, CN, $NO_2$, OH, COOH, $NH_2$, $C_{1-3}$ alkyl and $C_{1-3}$ heteroalkyl, the $C_{1-3}$ alkyl and $C_{1-3}$ heteroalkyl being optionally substituted with 1, 2 or 3 $R_g$.

In some embodiments of the present application, $R_{10}$, $R_{11}$ and $R_{12}$ in the formula (I) are each independently selected from the group consisting of H, F, Cl, Br, I, CN, $NO_2$, OH, COOH, $NH_2$, Me, Et, $CF_3$, OMe, $CHF_2$, $CH_2F$, $NHCH_3$ and $N(CH_3)_2$.

In some embodiments of the present application, ring A in the formula (I) is phenyl.

In some embodiments of the present application, the structural unit

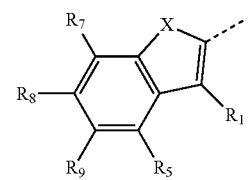

in the formula (I) is

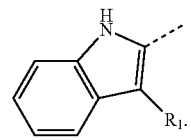

In some embodiments of the present application, the structural unit

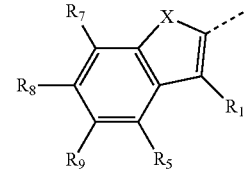

in the formula (I) is

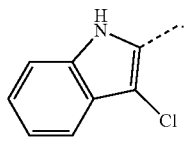

In some embodiments of the present application, the structural unit

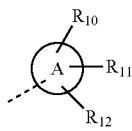

in the formula (I) is selected from the group consisting of

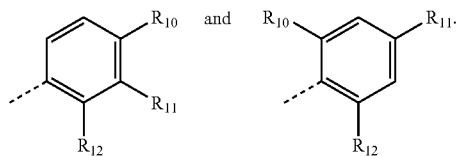

In some embodiments of the present application, the structural unit

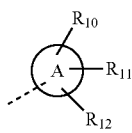

in the formula (I) is selected from the group consisting of

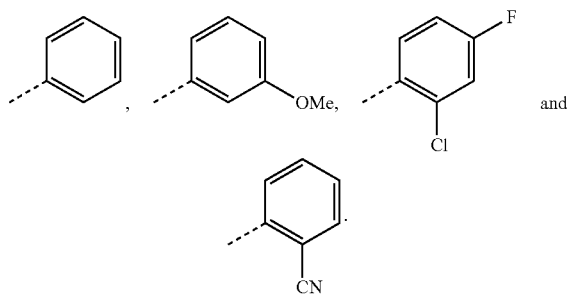

In some embodiments of the present application, $R_a$, $R_b$, $R_c$, $R_d$, $R_e$, $R_f$ and $R_g$ in the formula (I) are each independently selected from the group consisting of H, F, Cl, Br, I, OH, CN, $NH_2$, COOH, $C(=O)NH_2$, $C_{1-6}$ alkyl, $C_{1-6}$ heteroalkyl and cyclopropyl, the $C_{1-6}$ alkyl, $C_{1-6}$ heteroalkyl and cyclopropyl being optionally substituted with 1, 2 or 3 R; the other variables are as defined in the present application.

In some embodiments of the present application, $R_a$, $R_b$, $R_c$, $R_d$, $R_e$, $R_f$ and $R_g$ in the formula (I) are each independently selected from the group consisting of H, F, Cl, Br, I, OH, CN, $NH_2$, COOH, $C(=O)NH_2$, Me, Et, $CF_3$, $CHF_2$, $CH_2F$, $NHCH_3$ and $N(CH_3)_2$; the other variables are as defined in the present application.

In some embodiments of the present application, $R_1$ in the formula (I) is selected from the group consisting of H, F, Cl, Br, I, CN, COOH, $NH_2$, $C_{1-3}$ alkyl and $C_{1-3}$ heteroalkyl, the $C_{1-3}$ alkyl and $C_{1-3}$ heteroalkyl being optionally substituted with 1, 2 or 3 $R_a$; the other variables are as defined in the present application.

In some embodiments of the present application, $R_1$ in the formula (I) is selected from the group consisting of H, F, Cl, Br, I, CN, COOH, $NH_2$, Me, Et, $CF_3$, $CHF_2$, $CH_2F$, —$NHCH_3$ and —$N(CH_3)_2$; the other variables are as defined in the present application.

In some embodiments of the present application, $R_2$ in the formula (I) is selected from the group consisting of $C_{1-3}$ alkyl and $C_{1-3}$ heteroalkyl, the $C_{1-3}$ alkyl and $C_{1-3}$ heteroalkyl being optionally substituted with 1, 2 or 3 $R_b$; the other variables are as defined in the present application.

In some embodiments of the present application, $R_2$ in the formula (I) is selected from the group consisting of Me, Et, $CF_3$, $CH_2CF_3$, $CHF_2$, $CH_2F$, —$NHCH_3$ and —$N(CH_3)_2$.

In some embodiments of the present application, $R_3$ in the formula (I) is H; the other variables are as defined in the present application.

In some embodiments of the present application, $R_4$ in the formula (I) is selected from the group consisting of COOH, $NH_2$, $C_{1-6}$ alkyl, —NH—$C_{1-6}$ alkyl, —N($C_{1-6}$ alkyl)$_2$, —C(=O)—O—$C_{1-6}$ alkyl, —C(=O)—S—$C_{1-6}$ alkyl, $C_{3-6}$ cycloalkyl, 3-6 membered heterocycloalkyl and phenyl, the $C_{1-6}$ alkyl, —NH—$C_{1-6}$ alkyl, —N($C_{1-6}$ alkyl)$_2$, —C(=O)—O—$C_{1-6}$ alkyl, —C(=O)—S—$C_{1-6}$ alkyl, $C_{3-6}$ cycloalkyl, 3-6 membered heterocycloalkyl and phenyl being optionally substituted with 1, 2 or 3 $R_d$; the other variables are as defined in the present application.

In some embodiments of the present application, $R_4$ in the formula (I) is selected from the group consisting of COOH, $NH_2$, $C_{1-6}$ alkyl, —NH—$C_{1-6}$ alkyl, —N($C_{1-6}$ alkyl)$_2$, —C(=O)—O—$C_{1-6}$ alkyl, —C(=O)—S—$C_{1-6}$ alkyl, cyclopropyl, cyclopentyl, cyclohexyl, azetidinyl and phenyl; the other variables are as defined in the present application.

In some embodiments of the present application, $R_4$ in the formula (I) is selected from the group consisting of —$NHCH_3$ and —$N(CH_3)_2$; the other variables are as defined in the present application.

In some embodiments of the present application, $R_5$ in the formula (I) is selected from the group consisting of H, $C_{1-3}$ alkyl and $C_{1-3}$ heteroalkyl, the $C_{1-3}$ alkyl and $C_{1-3}$ heteroalkyl being optionally substituted with 1, 2 or 3 $R_e$; the other variables are as defined in the present application.

In some embodiments of the present application, $R_5$ in the formula (I) is H; the other variables are as defined in the present application.

In some embodiments of the present application, $R_6$, $R_7$, $R_8$ and $R_9$ in the formula (I) are H; the other variables are as defined in the present application.

In some embodiments of the present application, $R_{10}$, $R_{11}$ and $R_{12}$ in the formula (I) are each independently selected from the group consisting of H, F, Cl, Br, I, CN, $NO_2$, OH, COOH, $NH_2$, $C_{1-3}$ alkyl and $C_{1-3}$ heteroalkyl, the $C_{1-3}$ alkyl and $C_{1-3}$ heteroalkyl being optionally substituted with 1, 2 or 3 $R_g$; the other variables are as defined in the present application.

In some embodiments of the present application, $R_{10}$, $R_{11}$ and $R_{12}$ in the formula (I) are each independently selected from the group consisting of H, F, Cl, Br, I, CN, $NO_2$, OH, COOH, NH$_2$, Me, Et, CF$_3$, OMe, CHF$_2$, CH$_2$F, NHCH$_3$ and N(CH$_3$)$_2$; the other variables are as defined in the present application.

In some embodiments of the present application, ring A in the formula (I) is phenyl; the other variables are as defined in the present application.

In some embodiments of the present application, the structural unit

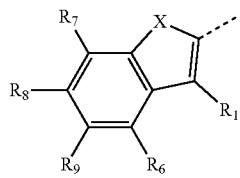

in the formula (I) is

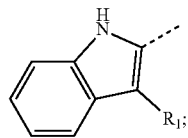

the other variables are as defined in the present application.

In some embodiments of the present application, the structural unit

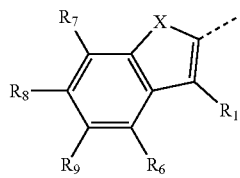

in the formula (I) is

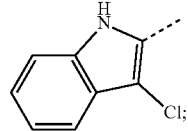

the other variables are as defined in the present application.

In some embodiments of the present application, the structural unit

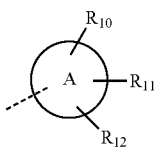

in the formula (I) is selected from the group consisting of

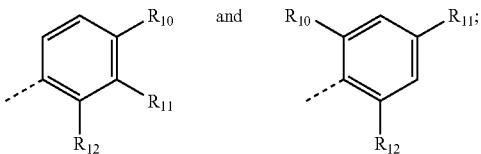

the other variables are as defined in the present application.

In some embodiments of the present application, the structural unit

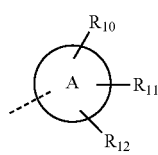

in the formula (I) is selected from the group consisting of

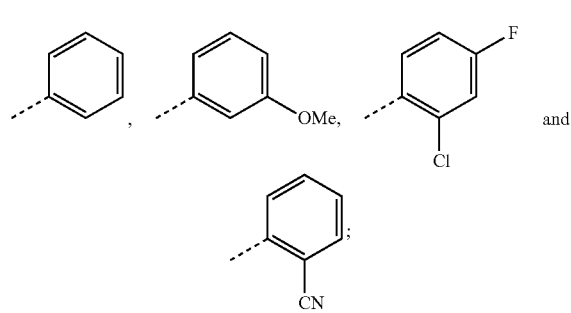

the other variables are as defined in the present application.

Some other embodiments of the present application are derived from any combination of the variables as described above.

The present application also provides a pharmaceutical composition, comprising a therapeutically effective amount of the compound, the isomer thereof or the pharmaceutically acceptable salt thereof as an active ingredient, and a pharmaceutically acceptable carrier.

The present application also provides a method for treating an ER-related disease in a mammal, comprising administering to the mammal, preferably a human, in need of such treatment a therapeutically effective amount of the compound, the isomer thereof or the pharmaceutically acceptable salt thereof, or the pharmaceutical composition thereof.

The present application also provides use of the compound, the isomer thereof or the pharmaceutically acceptable salt thereof, or the pharmaceutical composition thereof, in preparing a medicament for treating an ER-related disease.

The present application also provides use of the compound, the isomer thereof or the pharmaceutically acceptable salt thereof, or the pharmaceutical composition thereof, in treating an ER-related disease.

The present application also provides the compound, the isomer thereof or the pharmaceutically acceptable salt thereof, or the pharmaceutical composition thereof, for treating an ER-related disease.

The present application also provides use of the compound, the isomer thereof or the pharmaceutically acceptable salt thereof in preparing an ER inhibitor.

The present application also provides use of the composition in preparing an ER inhibitor.

In some embodiments of the present application, the ER-related disease is breast cancer.

In some embodiments of the present application, the breast cancer is ER-positive breast cancer.

The present application also provides use of the compound, the isomer thereof or the pharmaceutically acceptable salt thereof in preparing a medicament for treating ER-positive breast cancer.

Technical Effects

The compound of the present application has excellent inhibitory effect on cytochrome P450 enzymes. This provides great feasibility for developing combination therapies in clinic. The compounds of the present application can be used in the treatment of diseases related to the estrogen signaling pathway, such as breast cancer.

The compounds of the present application generally have excellent anti-proliferative activity against breast cancer cell MCF7.

The compounds of the present application have superior ADME properties in vitro: they show excellent liver microsomal stability (PPB), and minor species difference; they have good inhibitory activity against CYP1A2, CYP2C9, CYP2C19 and CYP2D6, etc., and significantly reduced risk of drug-drug interaction (DDI) in clinic; they also have good permeability.

As for PK properties in vivo, the compounds of the present application also demonstrate superior pharmacokinetic properties: the apparent volume of distribution (Vdss) in mice and rats suggests that the compounds of the present application may have a broader tissue distribution. The compounds of the present application demonstrate good exposure and bioavailability via oral administration. In a study investigating the efficacy in mice with MCF7 breast cancer, the compounds of the present application showed good tumor shrinkage efficacy.

Observation on inhibition of uterine wet weight in immature rats showed that the compounds of the present application significantly inhibited the growth of the uterus in rats, thus having lower risk in endometrial thickening or endometrial cancer and good safety.

Definitions and Description

Unless otherwise stated, the following terms and phrases used herein are intended to have the following meanings. A particular term or phrase, unless otherwise specifically defined, should not be considered as uncertain or unclear, but construed according to its common meaning. When referring to a trade name, it is intended to refer to its corresponding commercial product or its active ingredient.

The term "pharmaceutically acceptable" is used herein for those compounds, materials, compositions, and/or dosage forms which are, within the scope of sound medical judgment, suitable for use in contact with the tissues of human beings and animals without excessive toxicity, irritation, allergic response, or other problems or complications, and commensurate with a reasonable benefit/risk ratio.

The term "pharmaceutically acceptable salt" refers to a salt of the compound disclosed herein, which is prepared from the compound having particular substituents disclosed herein and a relatively nontoxic acid or base. When the compound of the present application contains a relatively acidic functional group, a base addition salt can be given by contacting such a compound with a sufficient amount of a base in a pure solution or a suitable inert solvent.

The pharmaceutically acceptable salts of the present application can be synthesized from a parent compound having an acidic or basic group by conventional chemical methods. In general, such salts are prepared by the following method: the free acid or base form of the compound reacting with a stoichiometric amount of the appropriate base or acid in water or an organic solvent or a mixture thereof.

The compound of the present application may have a specific geometric or stereoisomeric form. All such compounds are contemplated herein, including cis and trans isomers, (−)- and (+)-enantiomers, (R)- and (S)-enantiomers, diastereoisomers, (D)-isomers, (L)-isomers, and racemic mixtures and other mixtures thereof, such as an enantiomer or diastereomer enriched mixture, all of which are encompassed within the scope of the present application. Substituents such as alkyl may have an additional asymmetric carbon atom. All these isomers and mixtures thereof are encompassed within the scope of the present application.

Unless otherwise stated, the term "enantiomer" or "optical isomer" refers to stereoisomers that are mirror images of each other.

Unless otherwise stated, the term "cis-trans isomer" or "geometric isomer" results from the inability of a single bond of a ring carbon atom or a double bond to rotate freely.

Unless otherwise stated, the term "diastereoisomer" refers to stereoisomers in which molecules each have two or more chiral centers and are not mirror images of each other.

Unless otherwise stated, "(+)" stands for dextrorotation, "(−)" stands for levorotation, and "(±)" stands for racemization.

Unless otherwise stated, the absolute configuration of a stereogenic center is represented by a wedged solid bond ( ⬩) and a wedged dashed bond ( ⬩), and the relative vconfiguration of a stereogenic center is represented by a straight solid bond ( ⬩) and a straight dashed bond ( ⬩). A wavy line ( ⬩) represents a wedged solid bond ( ⬩) or a wedged dashed bond ( ⬩), or a wavy line ( ⬩) represents a straight solid bond ( ⬩) and a straight dashed bond ( ⬩).

Unless otherwise stated, when a double bond structure such as a carbon-carbon double bond, a carbon-nitrogen double bond, and a nitrogen-nitrogen double bond is present in the compound, and each atom on the double bond is linked to two different substituents (in the double bond including an nitrogen atom, a lone pair of electrons on the nitrogen atom is regarded as a substituent to which the nitrogen atom is linked), if the atom on the double bond of the compound and its substituents are linked using a wavy line ( ⬩) it means that the compound exists in the form of a (Z)-type isomer, a (E)-type isomer, or a mixture of the two isomers. For example, the following formula (A) represents that the compound exists in the form of a single isomer of formula (A-1) or formula (A-2) or in the form of a mixture of both isomers of formula (A-1) and formula (A-2); the following formula (B) represents that the compound exists in the form of a single isomer of formula (B-1) or formula (B-2) or in the form of a mixture of both isomers of formula (B-1) and formula (B-2); and the following formula (C) represents that the compound exists in the form of a single isomer of formula (C-1) or formula (C-2) or in the form of a mixture of both isomers of formula (C-1) and formula (C-2).

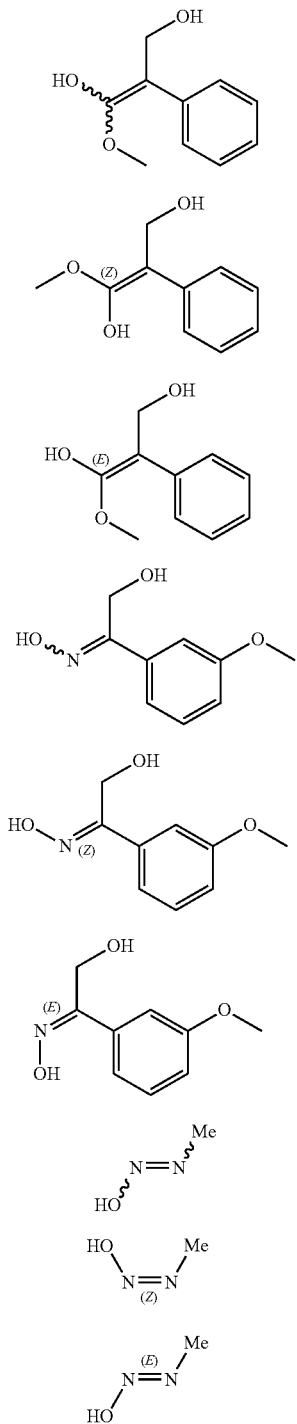

The compound of the present application may be present in a particular form. Unless otherwise stated, the term "tautomer" or "tautomeric form" means that different functional isomers are in dynamic equilibrium at room temperature and can be rapidly converted into each other. If tautomers are possible (e.g., in solution), the chemical equilibrium of the tautomers can be achieved. For example, a proton tautomer, also known as a prototropic tautomer, includes the interconversion by proton transfer, such as keto-enol isomerization and imine-enamine isomerization. A valence isomer includes the interconversion by recombination of some bonding electrons. A specific example of the keto-enol tautomerization is the interconversion between two tautomers pentane-2,4-dione and 4-hydroxypent-3-en-2-one.

Unless otherwise stated, the term "enriched with one isomer", "isomer enriched", "enriched with one enantiomer", or "enantiomer enriched" means that the content of one of the isomers or enantiomers is less than 100% and more than or equal to 60%, 70%, 80%, 90%, 95%, 96%, 97%, 98%, 99%, 99.5%, 99.6%, 99.7%, 99.8%, or 99.9%.

Unless otherwise stated, the term "isomeric excess" or "enantiomeric excess" refers to the difference between the relative percentages of two isomers or enantiomers. For example, if the content of one isomer or enantiomer is 90% and the content of the other isomer or enantiomer is 10%, the isomeric or enantiomeric excess (ee) is 80%.

Optically active (R)- and (S)-isomers and D and L isomers can be prepared by chiral synthesis or chiral reagents or other conventional techniques. If one enantiomer of a certain compound disclosed herein is to be obtained, the desired pure enantiomer can be prepared by asymmetric synthesis or derivatization using a chiral auxiliary, wherein the resulting diastereoisomeric mixture is separated and the auxiliary group is cleaved. Alternatively, when the molecule contains a basic functional group (such as amino) or an acidic functional group (such as carboxyl), the compound reacts with an appropriate optically active acid or base to form a salt of the diastereoisomer, which is then subjected to diastereoisomeric resolution through conventional methods in the art to get the pure enantiomer. Furthermore, the enantiomer and the diastereoisomer are generally isolated through chromatography using a chiral stationary phase, optionally in combination with chemical derivatization (e.g., carbamate generated from amines). The compound of the present application may contain an unnatural proportion of atomic isotope at one or more of the atoms that constitute the compound. For example, the compound may be labeled with a radioisotope, such as tritium ($^3H$), iodine-125 ($^{125}I$), or C-14 ($^{14}C$). For another example, hydrogen can be substituted by deuterium to form a deuterated drug, and the bond formed by deuterium and carbon is firmer than that formed by common hydrogen and carbon. Compared with an un-deuterated drug, the deuterated drug has the advantages of reduced toxic side effect, increased stability, enhanced efficacy, prolonged biological half-life and the like. All isotopic variations of the compound of the present application, whether radioactive or not, are encompassed within the scope of the present application. "Optional" or "optionally" means that the subsequently described event or circumstance may, but not necessarily, occur, and the description includes instances where the event or circumstance occurs and instances where it does not.

The term "substituted" means that one or more hydrogen atoms on a specific atom are substituted by substituents which may include deuterium and hydrogen variants, as long as the valence of the specific atom is normal and the substituted compound is stable. When the substituent is an oxygen (i.e., =O), it means that two hydrogen atoms are substituted. Substitution by oxygen does not occur on aromatic groups. The term "optionally substituted" means that an atom can be substituted by a substituent or not. Unless otherwise specified, the type and number of the substituent may be arbitrary as long as being chemically achievable.

When any variable (e.g., R) occurs more than once in the constitution or structure of a compound, the variable is independently defined in each case. Thus, for example, if a group is substituted by 0-2 R, the group can be optionally substituted by two R at most, and the definition of R in each case is independent. Furthermore, a combination of a substituent and/or a variant thereof is permissible only if the combination can result in a stable compound.

When the number of a linking group is 0, for example, —(CRR)$_0$—, it means that the linking group is a single bond.

When one of variants is a single bond, then two groups bonding by this variant are bonded directly. For example, in A-L-Z, when L represents a single bond, it means that the structure is actually A-Z.

When a substituent is absent, it means that the substituent does not exist. For example, when X in A-X is absent, the structure is actually A.

When a bond of a substituent is cross-linked to two or more atoms on a ring, the substituent can be bonded to any atom on the ring. For example, structural unit

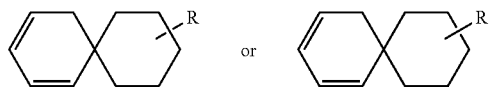

represents that the substituention of substituent R may occur in any one position on cyclohexyl or cyclohexadienyl.

When a substituent is listed without indicating the atom via which such substituent is bonded to the group to be substituted, then such substituent may be bonded via any atom in such substituent. For example, pyridinyl as a substituent can be linked to the group to be substituted through any carbon atom on the pyridine ring.

When the enumerative linking group does not indicate the direction for linking, the direction for linking is arbitrary. For example, when the linking group L contained in

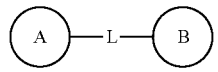

is -M-W—, -M-W— can either link ring A and ring B in a direction same as left-to-right reading order to form

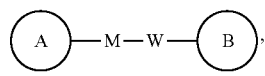

or link ring A and ring B in an opposing direction to form

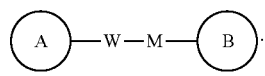

A combination of the linking group, a substituent and/or a variant thereof is permissible only if the combination can result in a stable compound.

Unless otherwise specified, when a group has one or more connectable sites, any one or more of the sites of the group may be connected to other groups by chemical bonds. The chemical bond that connects the site to another group may be represented by a straight solid bond (/), a straight dashed line bond (/), or a wavy line

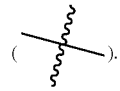

For example, the solid straight line in —OCH$_3$ indicates that the group is connected to another group through the oxygen atom; in

the straight dashed line indicates that the group is connected to another group through the two ends of the nitrogen atom; in

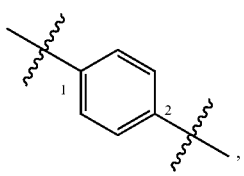 [SMILES: *c1ccc(*)cc1]

the wavy line indicates that the phenyl group is connected to other groups through the carbon atoms on positions 1 and 2.

Unless otherwise specified, the number of atoms on a ring is generally defined as the member number of the ring. For example, "5-7 membered ring" refers to a "ring" on which 5 to 7 atoms are arranged in a circle.

Unless otherwise specified, the term "C$_{1-8}$ alkyl" refers to a linear or branched saturated hydrocarbon group consisting of 1 to 8 carbon atoms. The C$_{1-8}$ alkyl includes C$_{1-6}$, C$_{1-5}$, C$_{1-4}$, C$_{1-3}$, C$_{1-2}$, C$_{2-6}$, C$_{2-4}$, C$_8$, C$_7$, C$_6$ and C$_5$ alkyl groups, etc., and may be monovalent (e.g., methyl), divalent (e.g., methylene), or polyvalent (e.g., methenyl). Examples of C$_{1-8}$ alkyl include, but are not limited to, methyl (Me), ethyl (Et), propyl (including n-propyl and isopropyl), butyl (including n-butyl, isobutyl, s-butyl, and t-butyl), pentyl (including n-pentyl, isopentyl, and neopentyl), hexyl, heptyl, octyl, and the like.

Unless otherwise specified, the term "C$_{1-6}$ alkyl" refers to a linear or branched saturated hydrocarbon group consisting of 1 to 6 carbon atoms. The C$_{1-6}$ alkyl includes C$_{1-5}$, C$_{1-4}$, C$_{1-3}$, C$_{1-2}$, C$_{2-6}$, C$_{2-4}$, C$_6$, and C$_5$ alkyl, etc., and may be monovalent (e.g., methyl), divalent (e.g., methylene), or polyvalent (e.g., methenyl). Examples of C$_{1-6}$ alkyl include, but are not limited to, methyl (Me), ethyl (Et), propyl (including n-propyl and isopropyl), butyl (including n-butyl, isobutyl, s-butyl, and t-butyl), pentyl (including n-pentyl, isopentyl, and neopentyl), hexyl, and the like.

Unless otherwise specified, the term "C$_{1-3}$ alkyl" refers to a linear or branched saturated hydrocarbon group consisting of 1 to 3 carbon atoms. The C$_{1-3}$ alkyl includes, but is not limited to, C$_{1-2}$ and C$_{2-3}$ alkyl, etc., and may be monovalent (e.g., methyl), divalent (e.g., methylene), or polyvalent (e.g., methenyl). Examples of C$_{1-3}$ alkyl include, but are not limited to, methyl (Me), ethyl (Et), propyl (including n-propyl and isopropyl), and the like. Unless otherwise specified, "$C_{2-8}$ alkenyl" is used to denote a linear or branched hydrocarbon group containing 2 to 8 carbon atoms and at least one carbon-carbon double bond, which may be located anywhere in the group. The $C_{2-8}$ alkenyl includes $C_{2-6}$, $C_{2-4}$, $C_{2-3}$, $C_4$, $C_3$, and $C_2$ alkenyl etc., and may be monovalent, divalent or polyvalent. Examples of $C_{2-8}$ alkenyl include, but are not limited to, ethenyl, propenyl, butenyl, pentenyl, hexenyl, butadienyl, 1,3-pentadienyl, 1,3-hexadienyl, and the like.

The term "heteroalkyl", by itself or in combination with another term, refers to a stable linear or branched alkyl radical or a combination thereof consisting of a specified number of carbon atoms and at least one heteroatom or heteroatom group. In some embodiments, the heteroatom is selected from the group consisting of B, O, N, and S, wherein nitrogen and sulfur atoms are optionally oxidized and the nitrogen heteroatom is optionally quaternized. In other embodiments, the heteroatom group is selected from the group consisting of —C(=O)O—, —C(=O)—, —C(=S)—, —S(=O), —S(=O)$_2$—, —C(=O)N(H)—, —N(H)—, —C(=NH)—, —S(=O)$_2$N(H)—, and —S(=O)N(H)—. In some embodiments, the heteroalkyl is $C_{1-6}$ heteroalkyl. In other embodiments, the heteroalkyl is $C_{1-3}$ heteroalkyl. The heteroatom or heteroatom group can be located at any interior position of heteroalkyl, including the position where the alkyl is linked to the rest part of the molecule. However, the terms "alkoxy", "alkylamino" and "alkylthio" (or thioalkxoy) are commonly used expressions and refer to those alkyl groups linked to the rest part of the molecule via an oxygen atom, an amino, or a sulfur atom, respectively. Examples of heteroalkyl include, but are not limited to, —OCH$_3$, —OCH$_2$CH$_3$, —OCH$_2$CH$_2$CH$_3$, —OCH$_2$(CH$_3$)$_2$, —CH$_2$—CH$_2$—O—CH$_3$, —NHCH$_3$, —N(CH$_3$)$_2$, —NHCH$_2$CH$_3$, —N(CH$_3$)(CH$_2$CH$_3$), —CH$_2$—CH$_2$—NH—CH$_3$, —CH$_2$—CH$_2$—N(CH$_3$)—CH$_3$, —SCH$_3$, —SCH$_2$CH$_3$, —SCH$_2$CH$_2$CH$_3$, —SCH$_2$(CH$_3$)$_2$, —CH$_2$—S—CH$_2$—CH$_3$, —CH$_2$—CH$_2$—S(=O)—CH$_3$, and —CH$_2$—CH$_2$—S(=O)$_2$—CH$_3$. At most two heteroatoms can be consecutive, such as, —CH$_2$—NH—OCH$_3$.

Unless otherwise specified, the term "halo" or "halogen", by itself or as part of another substituent, refers to a fluorine, chlorine, bromine or iodine atom.

Unless otherwise specified, "$C_{3-6}$ cycloalkyl" refers to a saturated cyclic hydrocarbon group consisting of 3 to 6 carbon atoms, including monocyclic and bicyclic ring systems. The $C_{3-6}$ cycloalkyl includes $C_{3-5}$ cycloalkyl, $C_{4-5}$ cycloalkyl, $C_{5-6}$ cycloalkyl and the like, and may be monovalent, divalent or polyvalent. Examples of $C_{3-6}$ cycloalkyl include, but are not limited to, cyclopropyl, cyclobutyl, cyclopentyl, cyclohexyl, and the like.

Unless otherwise specified, "$C_{3-5}$ cycloalkyl" denotes a saturated monocyclic hydrocarbon group consisting of 3 to 5 carbon atoms. The $C_{3-5}$ cycloalkyl includes $C_{3-4}$, $C_{4-5}$ cycloalkyl, and the like, and may be monovalent, divalent or polyvalent. Examples of $C_{3-5}$ cycloalkyl include, but are not limited to, cyclopropyl, cyclobutyl, cyclopentyl, and the like.

Unless otherwise specified, the term "3-6 membered heterocycloalkyl", by itself or in combination with other terms, refers to a saturated cyclic group consisting of 3 to 6 ring atoms, of which 1, 2, 3, or 4 ring atoms are heteroatoms independently selected from the group consisting of O, S, and N, with the remaining being carbon atoms. The nitrogen atom is optionally quaternized, and the nitrogen and sulfur heteroatoms can be optionally oxidized (i.e., NO and S(O)$_p$, wherein p is 1 or 2). This includes monocyclic and bicyclic systems, wherein the bicyclic system includes spirocyclic, fused, and bridged rings. Furthermore, with respect to the "3-6 membered heterocycloalkyl", a heteroatom may occupy the position where the heterocycloalkyl is connected to the rest of the molecule. The 3-6 membered heterocycloalkyl includes 4-6 membered, 5-6 membered, 4 membered, 5 membered, 6 membered heterocycloalkyl, and the like. Examples of 3-6 membered heterocycloalkyl include, but are not limited to, azetidinyl, oxetanyl, thietanyl, pyrrolidinyl, pyrazolidinyl, imidazolidinyl, tetrahydrothienyl (including tetrahydrothien-2-yl, tetrahydrothien-3-yl, etc.), tetrahydrofuranyl (including tetrahydrofuran-2-yl, etc.), tetrahydropyranyl, piperidinyl (including 1-piperidinyl, 2-piperidinyl, 3-piperidinyl, etc.), piperazinyl (including 1-piperazinyl, 2-piperazinyl, etc.), morpholinyl (including 3-morpholinyl, 4-morpholinyl, etc.), dioxanyl, dithianyl, isoxazolidinyl, isothiazolidinyl, 1,2-oxazinyl, 1,2-thiazinyl, hexahydropyridazinyl, homopiperazinyl, homopiperidinyl, etc.

Unless otherwise specified, the terms "$C_{6-10}$ aromatic ring" and "$C_{6-10}$ aryl" in the present application are used interchangeably. The term "$C_{6-10}$ aromatic ring" or "$C_{6-10}$ aryl" refers to a cyclic hydrocarbon group consisting of 6 to 10 carbon atoms and having a conjugated pi-electron system. The group may be a monocyclic, fused bicyclic or fused tricyclic system, where the rings are aromatic. It may be monovalent, divalent or multivalent, and the $C_{6-10}$ aryl includes $C_{6-9}$, $C_9$, $C_{10}$ and $C_6$ aryl groups, etc. Examples of $C_{6-10}$ aryl include, but are not limited to, phenyl, naphthyl (including 1-naphthyl, 2-naphthyl, etc.).

Unless otherwise specified, the terms "5-10 membered heteroaromatic ring" and "5-10 membered heteroaryl" are used interchangeably herein. The term "5-10 membered heteroaryl" refers to a cyclic group consisting of 5 to 10 ring atoms and having a conjugated pi-electron system, in which 1, 2, 3, or 4 ring atoms are heteroatoms independently selected from the group consisting of O, S and N, while the others are carbon atoms. It can be a monocyclic, fused bicyclic or fused tricyclic system, where the rings are aromatic. The nitrogen atom is optionally quaternized, and the nitrogen and sulfur heteroatoms are optionally oxidized (i.e., NO and S(O)$_p$, where p is 1 or 2). The 5-10 membered heteroaryl can be connected to the rest of the molecule via a heteroatom or a carbon atom. The 5-10 membered heteroaryl includes 5-8 membered, 5-7 membered, 5-6 membered, 5 membered and 6 membered heteroaryl groups, etc. Examples of the 5-10 membered heteroaryl include, but are not limited to, pyrrolyl (including N-pyrrolyl, 2-pyrrolyl, 3-pyrrolyl, etc.), pyrazolyl (including 2-pyrazolyl, 3-pyrazolyl, etc.), imidazolyl (including N-imidazolyl, 2-imidazolyl, 4-imidazolyl, 5-imidazolyl, etc.), oxazolyl (including 2-oxazolyl, 4-oxazolyl, 5-oxazolyl, etc.), triazolyl (including 1H-1,2,3-triazolyl, 2H-1,2,3-triazolyl, 1H-1,2,4-triazolyl, 4H-1,2,4-triazolyl, etc.), tetrazolyl, isoxazolyl (including 3-isoxazolyl, 4-isoxazolyl, 5-isoxazolyl, etc.), thiazolyl (including 2-thiazolyl, 4-thiazolyl, 5-thiazolyl, etc.), furanyl (including 2-furanyl, 3-furanyl, etc.), thienyl (including 2-thienyl, 3-thienyl, etc.), pyridinyl (including 2-pyridinyl, 3-pyridinyl, 4-pyridinyl, etc.), pyrazinyl, pyrimidinyl (including 2-pyrimidinyl, 4-pyrimidinyl, etc.), benzothiazolyl (including 5-benzothiazolyl, etc.), purinyl, benzimidazolyl (including 2-benzimidazolyl, etc.), benzoxazolyl, indolyl (including 5-indolyl, etc.), isoquinolinyl (including 1-isoquinolinyl, 5-isoquinolinyl, etc.), quinoxalinyl (including 2-quinoxalinyl, 5-quinoxalinyl, etc.) or quinolyl (including 3-quinolyl, 6-quinolyl, etc.).

Unless otherwise specified, the terms "5-6 membered heteroaromatic ring" and "5-6 membered heteroaryl" are used interchangeably herein. The term "5-6 membered heteroaryl" refers to a monocyclic group consisting of 5 to 6 ring atoms and having a conjugated pi-electron system, in which 1, 2, 3 or 4 ring atoms are heteroatoms independently selected from the group consisting of O, S, and N, while the others are carbon atoms. The nitrogen atom is optionally quaternized, and the nitrogen and sulfur heteroatoms are optionally oxidized (i.e., NO and S(O)$_p$, where p is 1 or 2). The 5-6 membered heteroaryl can be connected to the rest of the molecule via a heteroatom or a carbon atom. The 5-6 membered heteroaryl includes 5-membered and 6-membered heteroaryl. Examples of the 5-6 membered heteroaryl include, but are not limited to, pyrrolyl (including N-pyrrolyl, 2-pyrrolyl, 3-pyrrolyl, etc.), pyrazolyl (including 2-pyrazolyl, 3-pyrazolyl, etc.), imidazolyl (including N-imidazolyl, 2-imidazolyl, 4-imidazolyl, 5-imidazolyl, etc.), oxazolyl (including 2-oxazolyl, 4-oxazolyl, 5-oxazolyl, etc.), triazolyl (including 1H-1,2,3-triazolyl, 2H-1,2,3-triazolyl, 1H-1,2,4-triazolyl, 4H-1,2,4-triazolyl, etc.), tetrazolyl, isoxazolyl (including 3-isoxazolyl, 4-isoxazolyl, 5-isoxazolyl, etc.), thiazolyl (including 2-thiazolyl, 4-thiazolyl, 5-thiazolyl, etc.), furanyl (including 2-furanyl, 3-furanyl, etc.), thienyl (including 2-thienyl, 3-thienyl, etc.), pyridinyl (including 2-pyridinyl, 3-pyridinyl, 4-pyridinyl, etc.), pyrazinyl, or pyrimidinyl (including 2-pyrimidinyl, 4-pyrimidinyl, etc.).

Unless otherwise specified, $C_{n-n+m}$ or $C_n$-$C_{n+m}$ includes any one of the specific cases of n to n+m carbon atoms. For example, $C_{1-12}$ includes $C_1$, $C_2$, $C_3$, $C_4$, $C_5$, $C_6$, $C_7$, $C_8$, $C_9$, $C_{10}$, $C_{11}$ and $C_{12}$. Also, any range within n to n+m may be included. For example, $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$ and $C_{9-12}$, etc. Similarly, n–n+m membered represents that the number of atoms on the ring is n to n+m. For example, 3-12 membered ring includes 3 membered ring, 4 membered ring, 5 membered ring, 6 membered ring, 7 membered ring, 8 membered ring, 9 membered ring, 10 membered ring, 11 membered ring and 12 membered ring. n–n+m membered also represents any range within n to n+m. For example, 3-12 membered ring includes 3-6 membered ring, 3-9 membered ring, 5-6 membered ring, 5-7 membered ring, 6-7 membered ring, 6-8 membered ring, 6-10 membered ring, etc.

The term "leaving group" refers to a functional group or atom that can be replaced by another functional group or atom through a substitution reaction (e.g., nucleophilic substitution). For example, representative leaving groups include triflate; chlorine, bromine and iodine; sulfonate groups, such as mesylate, tosylate, p-bromobenzenesulfonate, p-toluenesulfonate, etc.; acyloxy groups, such as acetoxy, trifluoroacetoxy, etc.

The term "protecting group" includes, but is not limited to, "amino protecting group", "hydroxy protecting group" or "sulfydryl protecting group". The term "amino protecting group" refers to a protecting group suitable for preventing side reactions at the nitrogen atom of the amino. Representative amino protecting groups include, but are not limited to: formyl; acyl, such as alkanoyl (such as acetyl, trichloroacetyl or trifluoroacetyl); alkoxycarbonyl, such as tert-butoxycarbonyl (Boc); arylmethyloxycarbonyl, such as benzyloxycarbonyl (Cbz) and 9-fluorenylmethyloxycarbonyl (Fmoc); arylmethyl, such as benzyl (Bn), trityl (Tr), 1,1-di-(4'-methoxyphenyl)methyl; and silyl, such as trimethylsilyl (TMS) and tert-butyldimethylsilyl (TBS).

The term "hydroxyl protecting group" refers to a protecting group suitable for preventing side reactions of the hydroxyl group. Representative hydroxy protecting groups include, but are not limited to: alkyl, such as methyl, ethyl, and tert-butyl; acyl, such as alkanoyl (such as acetyl); arylmethyl, such as benzyl (Bn), p-methoxybenzyl (PMB), 9-fluorenylmethyl (Fm) and diphenylmethyl (DPM); and silyl, such as trimethylsilyl (TMS) and tert-butyldimethylsilyl (TBS).

The compounds of the present application can be prepared by a variety of synthetic methods well known to those skilled in the art, including the specific embodiments listed below, embodiments formed by combinations thereof with other chemical synthetic methods, and equivalents thereof known to those skilled in the art. Preferred embodiments include, but are not limited to, the examples disclosed herein.

Compounds are named according to conventional nomenclature rules in the art or using ChemDraw® software, and supplier's catalog names are given for commercially available compounds.

SPECIFIC EMBODIMENTS

The present application is described in detail below by way of examples. However, this is by no means disadvantageously limiting the scope of the present application.

It is known to those skilled in the art that in order to prepare the compound of the present application, the order of the reactions in each reaction scheme may be different, which also falls within the scope of the present application.

Example 1

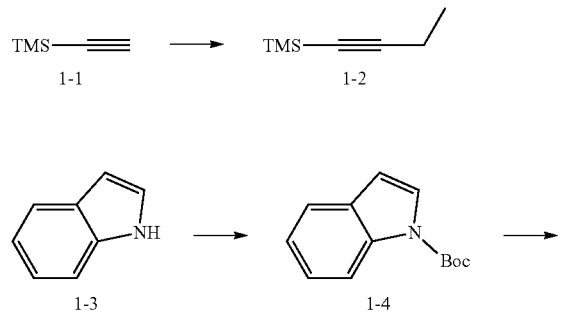

-continued
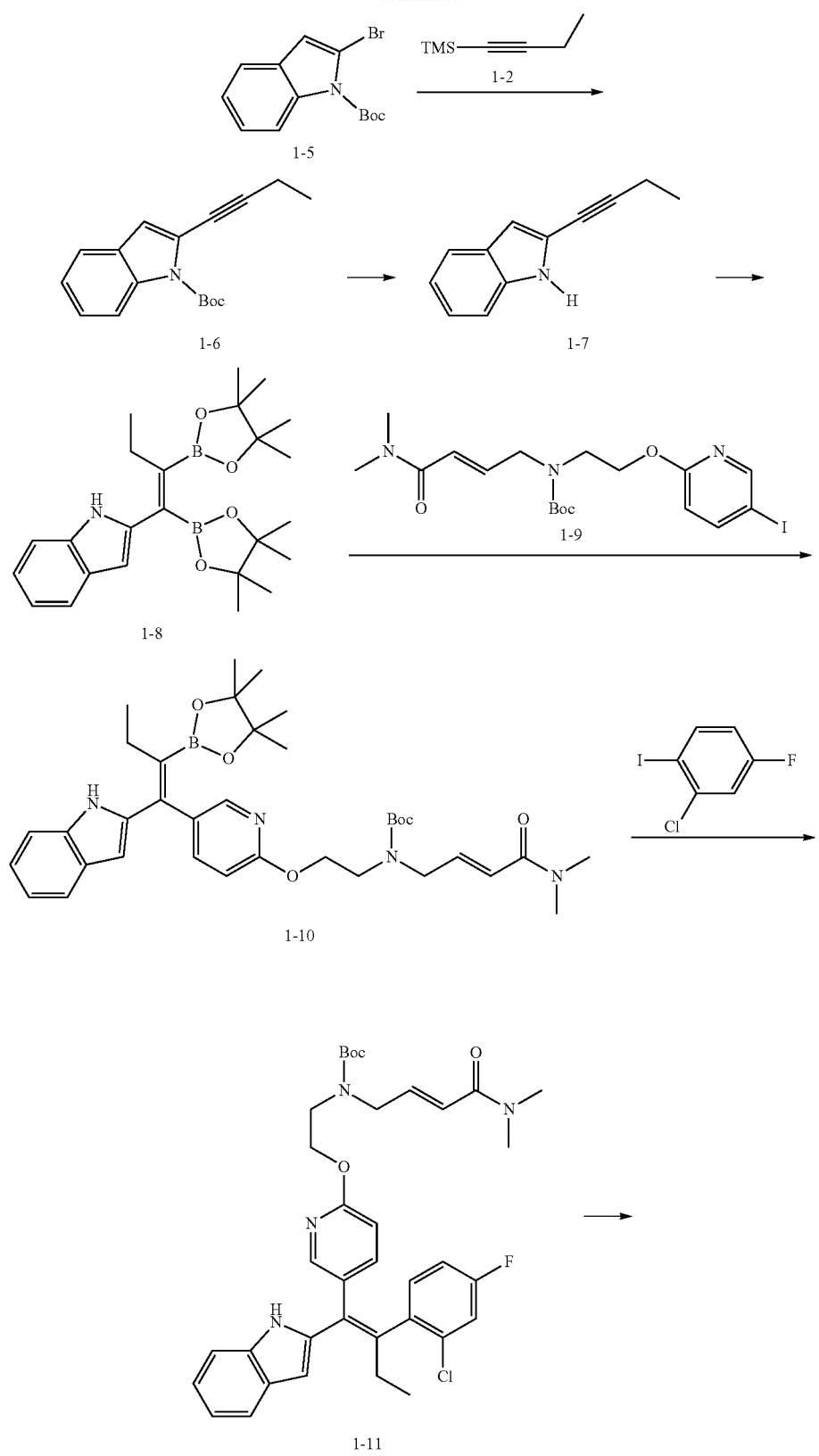

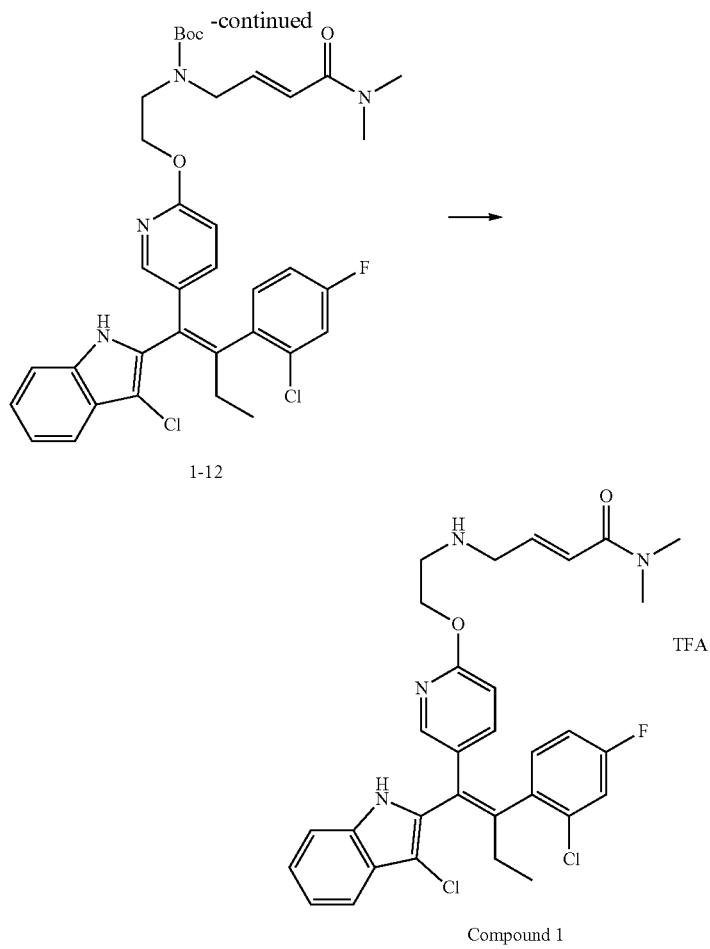

Compound 1

Step A: In nitrogen atmosphere at −75° C., n-butyllithium (2.5 M, 428.40 mL, 1.05 eq.) was added dropwise and slowly (in 1 hour) to a solution of compound 1-1 (100.00 g, 1.02 mol, 140.85 mL, 1.00 eq.) in tetrahydrofuran (500 mL). The reaction mixture was warmed up to 0° C. and stirred for 10 minutes, and was then cooled to −75° C. Hexamethylphosphoric triamide (201.06 g, 1.12 mol, 197.12 mL, 1.10 eq.) was added (in 1 hour). The reaction mixture was stirred at −75° C. for one hour and added with ethyl iodide (198.86 g, 1.27 mol, 101.98 mL, 1.25 eq.) (in one hour). The reaction mixture was warmed up to 20° C. and subjected to reaction for 10 hours before 400 mL of water was added. The organic phase was separated and washed three times with 400 mL of water, dried over anhydrous sodium sulfate, filtered and separated by distillation to give compound 1-2.

Step B: Dimethylaminopyridine (3.65 g, 29.88 mmol, 0.10 eq.) and Boc$_2$O (68.46 g, 313.70 mmol, 72.07 mL, 1.05 eq.) were added to a solution of compound 1-3 (35.00 g, 298.76 mmol, 1.00 eq.) in dichloromethane (400 mL). After subjected to reaction at 20° C. for 12 hours, the reaction mixture was extracted and washed twice with 400 mL of ammonium chloride solution. The organic phase was dried over anhydrous sodium sulfate, filtered and concentrated to give compound 1-4.

Step C: In nitrogen atmosphere at −75° C., lithium diisopropylamide (2 M, 75.95 mL, 1.10 eq.) was added dropwise and slowly to a solution of compound 1-4 (30.00 g, 138.08 mmol, 1.00 eq.) in tetrahydrofuran (400 mL). The reaction mixture was stirred at −75° C. for 30 minutes and added with cyanogen bromide (55.40 g, 523.04 mmol, 38.47 mL, 3.79 eq.). The reaction mixture was warmed up to 15° C. and subjected to reaction for 12 hours before 400 mL of water was added. The organic phase was separated and washed three times with 300 mL of water, dried over anhydrous sodium sulfate, and filtered to give a crude product. The crude product was separated by silica gel column chromatography (petroleum ether:ethyl acetate=1:0-50:1, v/v) to give compound 1-5.

Step D: To a solution of compound 1-5 (39.00 g, 131.69 mmol, 1.00 eq.) in N,N-dimethylacetamide (300 mL) were added cesium carbonate (85.81 g, 263.38 mmol, 2.00 eq.), copper(I) iodide (1.25 g, 6.58 mmol, 0.05 eq.), palladium acetate (1.48 g, 6.58 mmol, 0.05 eq.) and 1,1'-bis(diphenylphosphino)ferrocene (3.65 g, 6.58 mmol, 0.05 eq.). Then compound 1-2 (33.26 g, 263.38 mmol, 2.00 eq.) was added in nitrogen atmosphere. The reaction mixture was subjected to reaction at 80° C. for 12 hours, added with 1 L of ethyl acetate and 1 L of water, filtered and separated. The organic phase was extracted and washed three times with 1 L of water. The organic phase was dried over anhydrous sodium sulfate, filtered and concentrated to give a crude product. The crude product was separated by silica gel column chromatography (petroleum ether:ethyl acetate=1:0-30:1, v/v) to give compound 1-6.

Step E: Potassium carbonate (69.27 g, 501.25 mmol, 5.00 eq.) was added to a solution of compound 1-6 (27.00 g, 100.25 mmol, 1.00 eq.) in 300 mL of methanol and 15 mL of water. The reaction mixture was subjected to reaction at 70° C. for 12 hours, and then filtered and concentrated before 300 mL of ethyl acetate was added. The reaction mixture was extracted and washed twice with 300 mL of water. The organic phase was dried over anhydrous sodium sulfate, filtered and concentrated to give a crude product. The crude product was separated by silica gel column chromatography (petroleum ether:ethyl acetate=100:1-30:1, v/v) to give compound 1-7. MS [ESI, M+1]: 170.1.

Step F: Bis(pinacolato)diboron (600.25 mg, 2.36 mmol, 1.00 eq.) and tetrakis(triphenylphosphine)platinum(0) (58.82 mg, 47.28 μmol, 0.02 eq.) were added to a solution of compound 1-7 (400 mg, 2.36 mmol, 1.00 eq.) in 2-methyltetrahydrofuran (5 mL). The reaction mixture was subjected to reaction at 85° C. for 7 hours in nitrogen atmosphere and then cooled to room temperature to give compound 1-8 for direct use in the next reaction without purification. MS [ESI, M+1]: 424.3.

Step G: Compound 1-9 (791 mg, 1.66 mmol, 0.7 eq., see US 20160347717A1 for synthesis of the compound), cesium carbonate (1.08 g, 3.33 mmol, 2.00 eq.) and bis(triphenylphosphine)palladium(II) dichloride (58.41 mg, 83.21 μmol, 0.05 eq.) were added to a solution of compound 1-8 (1.0 g, 2.36 mmol, 1.00 eq.) in 2-methyltetrahydrofuran (5 mL) at room temperature. The reaction system was purged with nitrogen three times before water (0.2 mL) was added. The reaction mixture was subjected to reaction at 30° C. for 12 hours in nitrogen atmosphere to give compound 1-10 for direct use in the next reaction without purification. MS [ESI, M+1]: 645.5.

Step H: 2-Chloro-4-fluoroiodobenzene (510.81 mg, 1.99 mmol, 1.2 eq.) and aqueous potassium hydroxide (4 M, 2.9 mL, 7.00 eq.) were added to a solution of compound 1-10 (1.07 g, 1.66 mmol, 1.00 eq.) in 2-methyltetrahydrofuran (5 mL). The reaction system was purged with nitrogen three times. The reaction mixture was subjected to reaction at 85° C. for 6 hours in nitrogen atmosphere, added with bis(triphenylphosphine)palladium(II) dichloride (58.25 mg, 83 μmol, 0.05 eq.), and subjected to reaction at 85° C. for 16 hours in nitrogen atmosphere. The reaction mixture was cooled to room temperature and added with 10 mL of water and 10 mL of ethyl acetate. The aqueous phase was extracted three times with 10 mL of ethyl acetate, and the organic phases were combined and washed once with 50 mL of saturated brine. The organic phase was dried over anhydrous sodium sulfate, filtered and concentrated to give a crude product. The crude product was separated by silica gel column chromatography (petroleum ether:ethyl acetate=5:1-1:1, v/v) to give compound 1-11. MS [ESI, M+1]: 647.2.

Step I: N-chlorosuccinimide (171.83 mg, 1.29 mmol, 1.2 eq.) was added to a solution of compound 1-11 (694 mg, 1.07 mmol, 1.00 eq.) in dichloromethane (40 mL). The reaction mixture was subjected to reaction at 25° C. for 1 hour, and then washed twice with 30 mL of saturated aqueous sodium sulfite. The organic phase was dried over anhydrous sodium sulfate, filtered and concentrated to give compound 1-12. MS [ESI, M+1]: 681.1.

Step J: 8 mL of trifluoroacetic acid (TFA) was added to a solution of compound 1-12 (621 mg, 911.06 μmol, 1.00 eq.) in dichloromethane (8 mL). The reaction mixture was subjected to reaction at 25° C. for 1 hour, and concentrated to give a crude product. The crude product was separated by prep-HPLC (water (0.1% trifluoroacetic acid, v/v)/acetonitrile system) to give compound 1. MS [ESI, M+1]: 581.1.

$^1$H NMR (400 MHz, CDCl$_3$): 9.19 (s, 1H), 7.77-7.69 (m, 1H), 7.69-7.61 (m, 1H), 7.35 (dd, J=2.4, 8.8 Hz, 1H), 7.32-7.28 (m, 1H), 7.25-7.11 (m, 3H), 7.07 (dd, J=2.4, 8.4 Hz, 1H), 6.95-6.90 (m, 1H), 6.60-6.55 (m, 2H), 6.51-6.44 (m, 1H), 5.81 (br s, 2H), 4.39 (br s, 2H), 3.70 (br d, J=4.4 Hz, 2H), 3.28 (br s, 2H), 2.97 (s, 3H), 2.92 (s, 3H), 2.68-2.48 (m, 2H), 0.96 (t, J=7.6 Hz, 3H)

Example 2

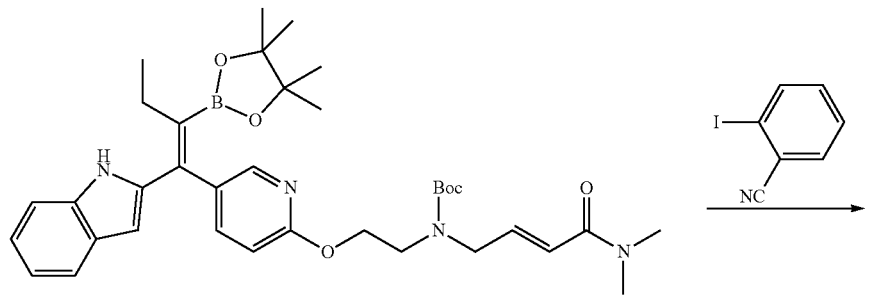

1-10

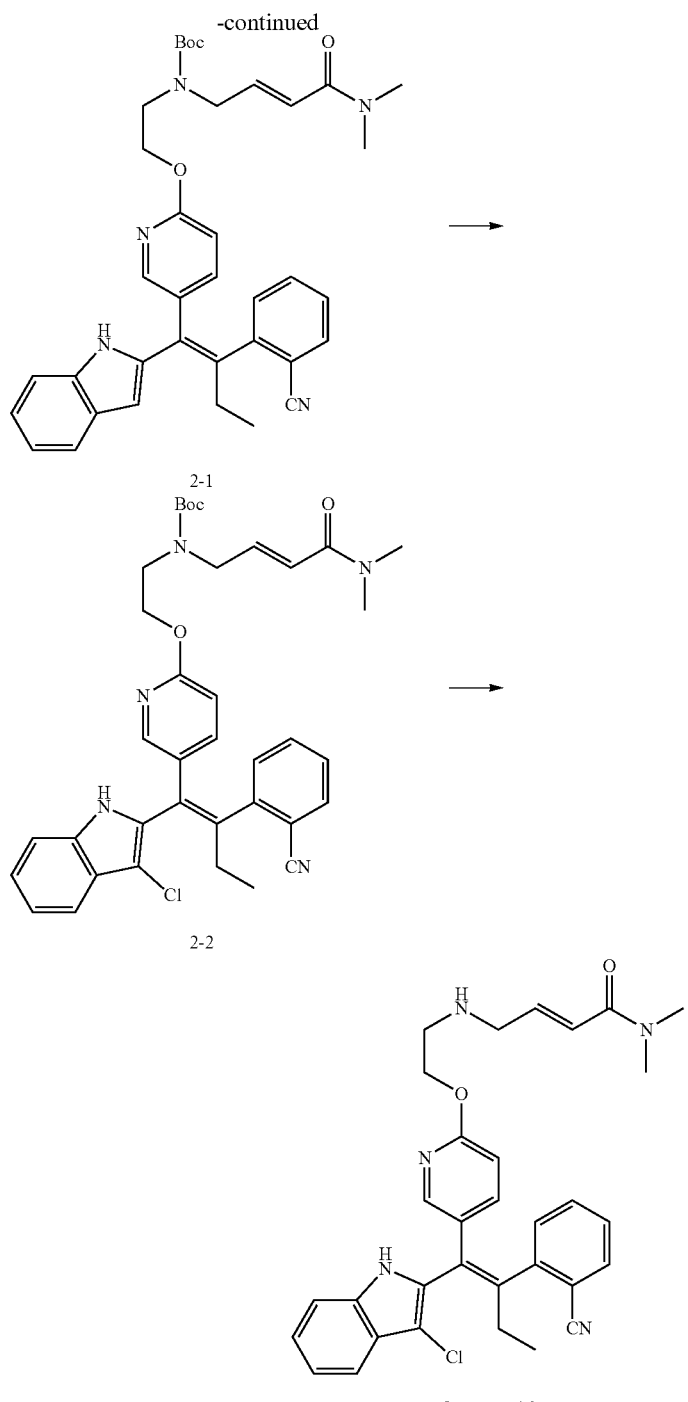

Step A: 2-Iodobenzonitrile (760.3 mg, 3.32 mmol, 2 eq.), aqueous potassium hydroxide (4 M, 2.90 mL, 7 eq.) and bis(triphenylphosphine)palladium(II) dichloride (58.25 mg, 83 μmol, 0.05 eq.) were added to a solution of compound 1-10 (1.07 g, 1.66 mmol, 1.00 eq.) in 2-methyltetrahydrofuran (5 mL). The reaction mixture was purged with nitrogen three times, and subjected to reaction at 85° C. for 8 hours in nitrogen atmosphere. The reaction mixture was then added with bis(triphenylphosphine)palladium(II) dichloride (58.25 mg, 83 μmol, 0.05 eq.), and subjected to reaction at 85° C. for 24 hours. The reaction mixture was diluted with 15 mL of water and 15 mL of ethyl acetate, and extracted three times with 15 mL of ethyl acetate. The organic phases were combined, washed once with 50 mL of saturated brine, dried over anhydrous sodium sulfate, filtered and concentrated to give a crude product. The crude product was separated by silica gel column chromatography (PE:EA=5:1-1:2) to give compound 2-1. MS [ESI, M+1]: 620.4.

Step B: N-chlorosuccinimide (152.55 mg, 1.14 mmol, 1.2 eq.) was added to a solution of compound 2-1 (590 mg, 952 μmol, 1.00 eq.) in dichloromethane (10 mL). The reaction mixture was subjected to reaction at 25° C. for 2 hours. The reaction mixture was then washed twice with 10 mL of saturated aqueous sodium sulfite, and the organic phase was dried over anhydrous sodium sulfate, filtered and concentrated to give compound 2-2. MS [ESI, M+1]: 654.3.

Step C: 7 mL of trifluoroacetic acid was added to a solution of compound 2-2 (584 mg, 892.70 μmol, 1.00 eq.) in dichloromethane (7 mL). The reaction mixture was subjected to reaction at 25° C. for 1 hour, and concentrated to give a crude product. The crude product was separated by prep-HPLC (water (0.05% aqueous ammonia, v/v)/acetonitrile system) to give compound 2. MS [ESI, M+1]: 554.3.

1H NMR (400 MHz, CDCl$_3$) 8.54 (br s, 1H), 7.62-7.56 (m, 2H), 7.49-7.48 (m, 2H), 7.35 (br d, J=7.2 Hz, 1H), 7.27-7.22 (m, 2H), 7.19-7.13 (m, 3H), 6.75-6.71 (m, 1H), 6.40-6.30 (m, 2H), 4.18 (br s, 2H), 3.34 (br d, J=3.6 Hz, 2H), 2.96 (br s, 3H), 2.91 (br s, 3H), 2.85 (br s, 2H), 2.71-2.42 (m, 2H), 0.92 (br t, J=6.8 Hz, 3H)

Example 3

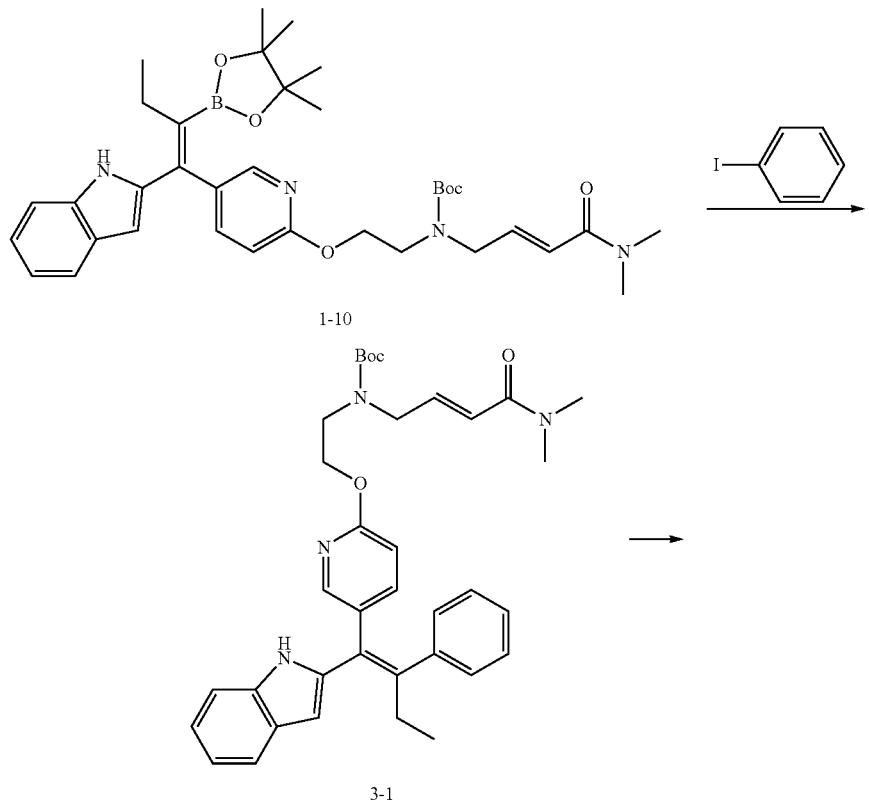

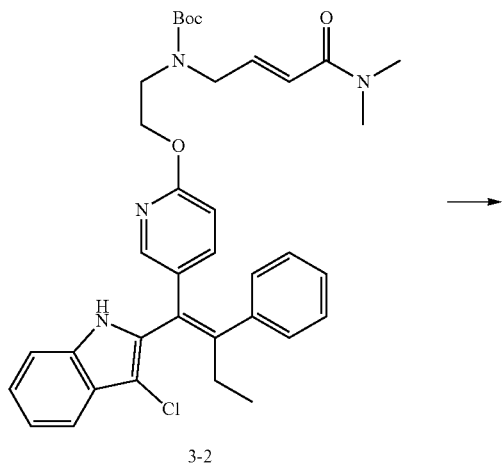

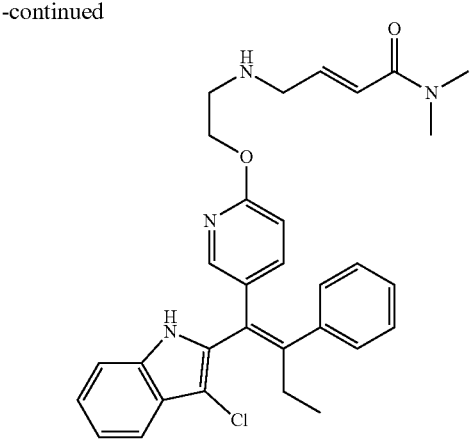

Compound 3

Step A: In nitrogen atmosphere, to a solution of compound 1-10 (500 mg, 775.67 μmol, 1.00 eq.), iodobenzene (205.71 mg, 1.01 mmol, 112.41 μL, 1.3 eq.), potassium hydroxide (261.12 mg, 4.65 mmol, 6 eq.) in 2-methyltetrahydrofuran (10 mL) and water (3 mL) was added bis(triphenylphosphine)palladium(II) dichloride (54.44 mg, 77.57 μmol, 0.1 eq.). The reaction mixture was purged with nitrogen three times, and subjected to reaction at 80° C. for 12 hours in nitrogen atmosphere. The reaction mixture was diluted with 20 mL of water and separated, and the aqueous phase was extracted three times with 50 mL of ethyl acetate. The organic phases were combined, washed once with 20 mL of saturated brine, dried over anhydrous sodium sulfate, filtered and concentrated to give a crude product. The crude product was separated by prep-HPLC (water (0.1% formic acid, v/v)/acetonitrile system) to give compound 3-1. MS [ESI, M+1]: 595.3.

Step B: In nitrogen atmosphere, N-chlorosuccinimide (17.96 mg, 134.51 μmol, 1 eq.) was added to a solution of compound 3-1 (80 mg, 134.51 μmol, 1 eq.) in dichloromethane (5 mL). The reaction mixture was subjected to reaction at 20° C. for 1 hour. The reaction was quenched with 2 mL of saturated aqueous sodium sulfite and the reaction mixture was separated. The aqueous phase was extracted three times with 20 mL of ethyl acetate, and the organic phases were combined, dried over anhydrous sodium sulfate, filtered and concentrated to give compound 3-2. MS [ESI, M+1]: 629.3.

Step C: In nitrogen atmosphere, 1 mL of trifluoroacetic acid was added to a solution of compound 3-2 (90 mg, 143.04 μmol, 1 eq.) in dichloromethane (5 mL). The reaction mixture was subjected to reaction at 20° C. for 10 minutes, and concentrated to give a crude product. The crude product was separated by prep-HPLC with a water (0.1% trifluoroacetic acid, v/v)/acetonitrile system and a water (0.05% aqueous ammonia, v/v)/acetonitrile system sequentially to give compound 3. MS [ESI, M+1]: 529.1.

$^1$H NMR (400 MHz, METHANOL-d$_4$) δ=7.67 (d, J=2.4 Hz, 1H), 7.57-7.51 (m, 1H), 7.36 (d, J=8.0 Hz, 1H), 7.31-7.09 (m, 8H), 6.77 (td, J=5.6, 15.2 Hz, 1H), 6.59-6.50 (m, 2H), 4.25 (br t, J=4.8 Hz, 2H), 3.43 (br dd, J=2.0, 4.0 Hz, 2H), 3.07 (d, J=2.0 Hz, 3H), 2.96 (d, J=0.8 Hz, 3H), 2.94-2.88 (m, 2H), 2.55 (q, J=7.6 Hz, 2H), 0.98 (t, J=7.2 Hz, 3H)

Compound 3 was adjusted to pH 3 with 1 M hydrochloric acid, and the solvent was removed under reduced pressure to give the monohydrochloride of compound 3.

$^1$H NMR (400 MHz, DMSO-d$_6$) 11.57 (s, 1H), 9.43 (br s, 2H), 7.67 (d, J=1.6 Hz, 1H), 7.50 (d, J=7.6 Hz, 1H), 7.40 (d, J=8.0 Hz, 1H), 7.34-7.28 (m, 2H), 7.27-7.11 (m, 6H), 6.83 (d, J=15.2 Hz, 1H), 6.67-6.53 (m, 2H), 4.39 (t, J=5.2 Hz, 2H), 3.77 (br d, J=5.2 Hz, 2H), 3.28-3.19 (m, 2H), 3.03 (s, 3H), 2.87 (s, 3H), 2.48-2.42 (m, 2H), 0.90 (t, J=7.2 Hz, 3H)

Example 4

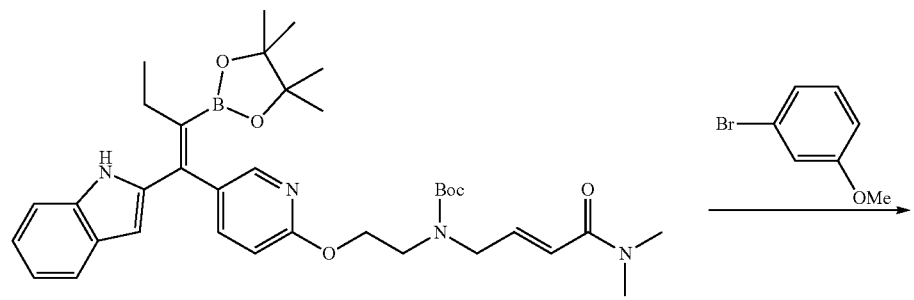

1-10

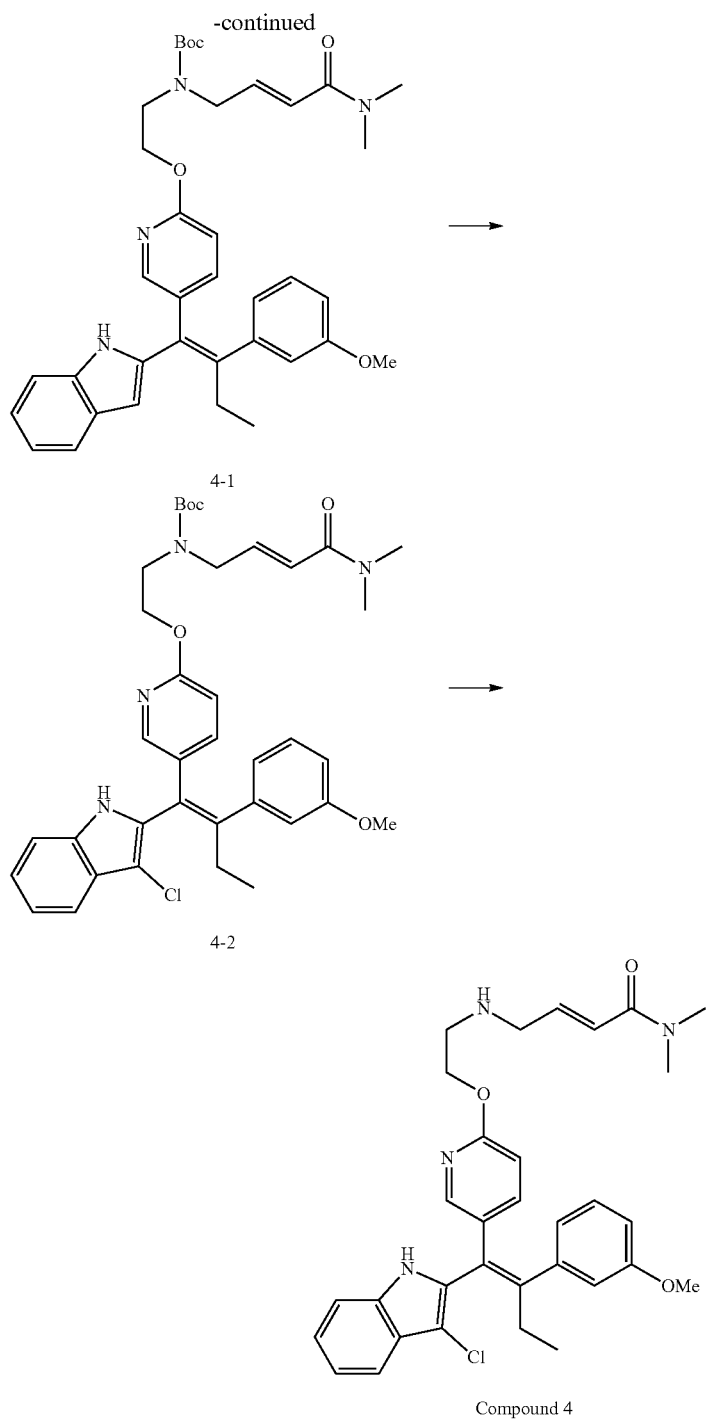

Step A: In nitrogen atmosphere, to a solution of compound 1-10 (500 mg, 775.67 μmol, 1.00 eq.), 1-bromo-3-methoxybenzene (188.60 mg, 1.01 mmol, 127.43 μL, 1.3 eq.), potassium hydroxide (261.12 mg, 4.65 mmol, 6 eq.) in 2-methyltetrahydrofuran (10 mL) and water (3 mL) was added bis(triphenylphosphine)palladium(II) dichloride (54.44 mg, 77.57 μmol, 0.1 eq.). The reaction mixture was purged with nitrogen three times, and subjected to reaction at 80° C. for 12 hours in nitrogen atmosphere. The reaction mixture was diluted with 20 mL of water and separated, and the aqueous phase was extracted three times with 50 mL of ethyl acetate. The organic phases were combined, washed once with 20 mL of saturated brine, dried over anhydrous sodium sulfate, filtered and concentrated to give a crude product. The crude product was separated by prep-HPLC (water (0.1% formic acid, v/v)/acetonitrile system) to give compound 4-1. MS [ESI, M+1]: 625.3

By Step B and Step C with reference to Step B and Step C in synthesis of compound 3, compound 4-2 (MS[ESI, M+1]: 625.3) and a crude product of compound 4 were obtained, respectively. The crude product was separated by prep-HPLC with a water (0.1% trifluoroacetic acid, v/v)/ acetonitrile system and a water (0.05% aqueous ammonia, v/v)/acetonitrile system sequentially to give compound 4. MS [ESI, M+1]: 559.1.

¹H NMR (400 MHz, DMSO-d₆) δ=11.45 (br s, 1H), 7.70-7.60 (m, 1H), 7.50 (br d, J=7.8 Hz, 1H), 7.39 (br d, J=7.8 Hz, 1H), 7.34-7.06 (m, 5H), 6.83-6.72 (m, 2H), 6.66-6.54 (m, 2H), 6.53-6.44 (m, 1H), 4.16 (br t, J=5.2 Hz, 2H), 3.69 (s, 3H), 3.30 (br d, J=4.4 Hz, 2H), 2.98 (s, 3H), 2.84 (s, 3H), 2.80-2.73 (m, 2H), 2.45 (br d, J=7.2 Hz, 2H), 2.06 (br d, J=13.2 Hz, 1H), 0.91 (br t, J=7.2 Hz, 3H)

The crude product was separated by prep-HPLC (water (0.05% hydrochloric acid, v/v)/acetonitrile system) to give the monohydrochloride of compound 4. MS [ESI, M+1]: 559.3

¹H NMR (400 MHz, DMSO-d₆) δ=11.59 (s, 1H), 9.54 (br s, 2H), 7.73-7.66 (m, 1H), 7.49 (d, J=7.6 Hz, 1H), 7.40 (d, J=8.0 Hz, 1H), 7.32-7.28 (m, 1H), 7.26 (br d, J=2.4 Hz, 1H), 7.23-7.17 (m, 2H), 7.16-7.09 (m, 1H), 6.88-6.80 (m, 1H), 6.80-6.72 (m, 2H), 6.66 (d, J=8.4 Hz, 1H), 6.63-6.55 (m, 1H), 4.51-4.31 (m, 2H), 3.78 (br d, J=5.6 Hz, 2H), 3.69 (s, 3H), 3.25 (br s, 2H), 3.02 (s, 3H), 2.85 (s, 3H), 2.45 (br d, J=7.2 Hz, 2H), 0.96-0.84 (m, 3H)

Example 5

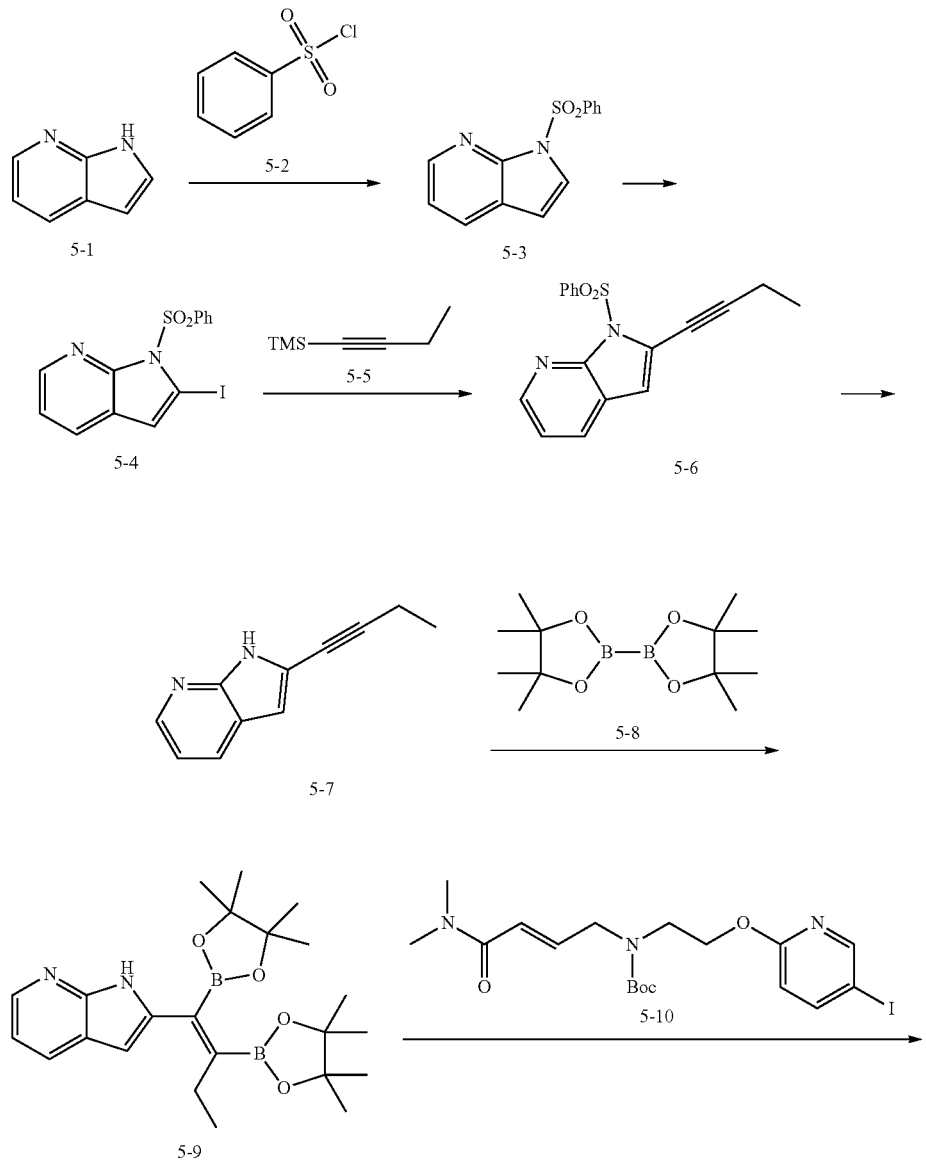

-continued
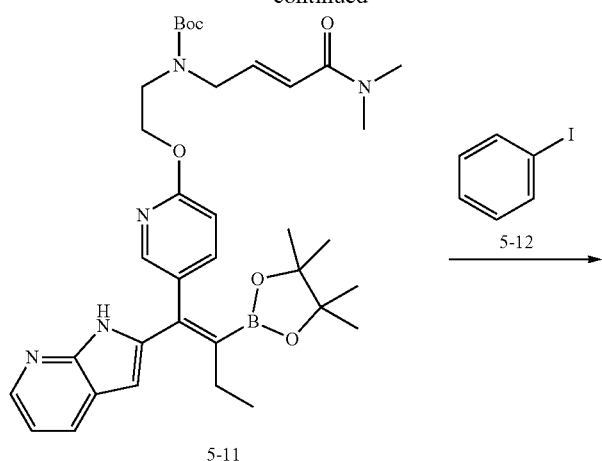
5-11
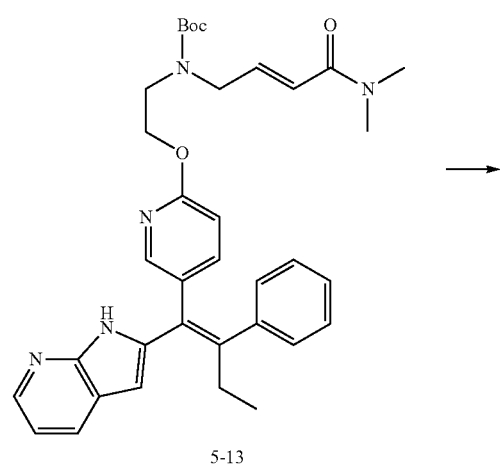
5-13
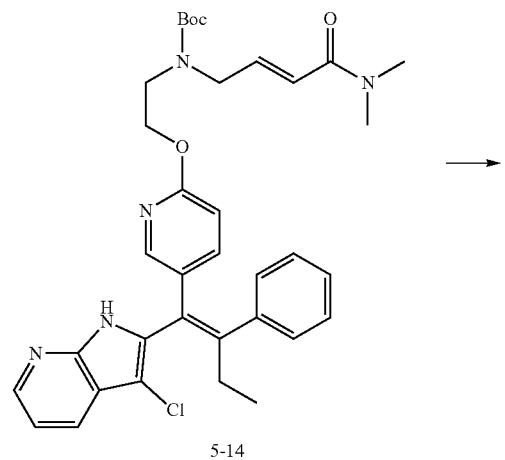
5-14

-continued

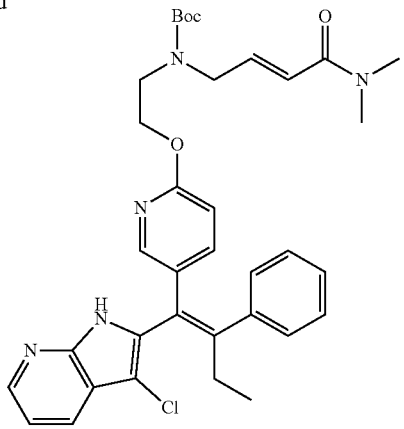

Compound 5

Step A: A solution of compound 5-1 (5 g, 42.32 mmol, 1 eq.) in N,N-dimethylformamide (50 mL) was cooled to 0° C., and added with sodium hydride (2.54 g, 63.49 mmol, 60% purity, 1.5 eq.) in batches. The reaction mixture was stirred at 0° C. for half an hour, added with compound 5-2 (8.22 g, 46.56 mmol, 5.96 mL, 1.1 eq.), warmed up to 20° C. and subjected to reaction for 1 hour before 50 mL of saturated aqueous ammonium chloride was added. The separated aqueous phase was extracted three times with 50 mL of ethyl acetate, and the organic phases were combined, washed twice with 50 mL of saturated brine, dried over anhydrous sodium sulfate, filtered and concentrated to give compound 5-3. MS [ESI, M+1]: 259.1

Step B: In nitrogen atmosphere at −70° C., lithium diisopropylamide (2 M, 6.39 mL, 1.1 eq.) was added dropwise and slowly to a solution of compound 5-3 (3 g, 11.61 mmol, 1 eq.) in tetrahydrofuran (20 mL). The reaction mixture was stirred at −70° C. for 30 minutes and added with iodine (4.42 g, 17.42 mmol, 3.51 mL, 1.5 eq.). The reaction mixture was warmed up to 25° C. and subjected to reaction for 2 hours before 20 mL of saturated aqueous ammonium chloride and 20 mL of saturated aqueous sodium sulfite were added. The aqueous phase was separated and washed three times with 50 mL of ethyl acetate, and the organic phases were combined, washed twice with 50 mL of saturated brine, dried over anhydrous sodium sulfate, filtered and concentrated to give a crude product. The crude product was separated by silica gel column chromatography (petroleum ether:ethyl acetate=5:1-3:1, v/v) to give compound 5-4. MS [ESI, M+1]: 384.9

Step C: To a solution of compound 5-4 (2 g, 5.21 mmol, 1 eq.) in N,N-dimethylacetamide (10 mL) were added cesium carbonate (8(3.39 g, 10.41 mmol, 2 eq.), copper(I) iodide (49.57 mg, 260.29 µmol, 0.05 eq.), palladium acetate (58.44 mg, 260.29 µmol, 0.05 eq.) and 1,1'-bis(diphenylphosphino)ferrocene (144.30 mg, 260.29 µmol, 0.05 eq.). Then compound 5-5 (1.31 g, 10.41 mmol, 2 eq.) was added in nitrogen atmosphere. The reaction mixture was subjected to reaction at 80° C. for 12 hours, added with 20 mL of ethyl acetate and 20 mL of water, filtered and separated. The aqueous phase was extracted three times with 20 mL of ethyl acetate, and the organic phases were combined and washed once with 20 mL of saturated brine, dried over anhydrous sodium sulfate, filtered and concentrated to give a crude product. The crude product was separated by silica gel column chromatography (petroleum ether:ethyl acetate=1:0-5:1, v/v) to give compound 5-6. MS [ESI, M+1]: 311.1

Step D: Sodium hydroxide (4 M, 708.83 µL, 4 eq.) was added to a 10-mL solution of compound 5-6 (220 mg, 708.83 µmol, 1 eq.). The reaction mixture was subjected to reaction at 60° C. for 2 hours, added with 10 mL of water and then extracted three times with 50 mL of ethyl acetate. The organic phase was dried over anhydrous sodium sulfate, filtered and concentrated to give compound 5-7. MS [ESI, M+1]: 171.2

Step E: Compound 5-8 (164.11 mg, 646.26 µmol, 1 eq.) and tetrakis(triphenylphosphine)platinum(0) (16.08 mg, 12.93 µmol, 0.02 eq.) were added to a solution of compound 5-7 (110 mg, 646.26 µmol, 1 eq.) in 2-methyltetrahydrofuran (10 mL). The reaction mixture was subjected to reaction at 85° C. for 12 hours in nitrogen atmosphere and then cooled to room temperature to give compound 5-9 for direct use in the next reaction without purification.

Step F: Compound 5-10 (215.03 mg, 452.38 µmol, 0.7 eq.), cesium carbonate (421.13 mg, 1.29 mmol, 2 eq.) and bis(triphenylphosphine)palladium(II) dichloride (22.68 mg, 32.31 µmol, 0.05 eq.) were added to a solution of compound 5-9 (274.11 mg, 646.26 µmol, 1 eq.) in 2-methyltetrahydrofuran (10 mL) at room temperature. The reaction system was purged with nitrogen three times before water (2.5 mL) was added. The reaction mixture was subjected to reaction at 30° C. for 12 hours in nitrogen atmosphere to give compound 5-11.

Step G: Compound 5-12 (131.84 mg, 646.26 µmol, 72.04 µL, 1 eq.), aqueous potassium hydroxide (4 M, 1.13 mL, 7 eq.) and bis(triphenylphosphine)palladium(II) dichloride (22.68 mg, 32.31 µmol, 0.05 eq.) were added to a solution of compound 5-11 (417.22 mg, 646.26 µmol, 1 eq.) in 2-methyltetrahydrofuran (10 mL). The reaction system was subjected to reaction at 85° C. for 12 hours in nitrogen atmosphere, then cooled to room temperature, and added with 20 mL of water and 20 mL of ethyl acetate. The aqueous phase was extracted three times with 20 mL of ethyl acetate, and the organic phases were combined and washed once with 20 mL of saturated brine. The organic phase was dried over anhydrous sodium sulfate, filtered and concentrated to give a crude product. The crude product was separated by reversed-phase column chromatography (water (0.1% formic acid, v/v)/acetonitrile system) to give compound 5-13. MS [ESI, M+1]: 596.3

Step H: N-chlorosuccinimide (6.72 mg, 50.36 μmol, 1.2 eq.) was added to a solution of compound 5-13 (25 mg, 41.97 μmol, 1 eq.) in dichloromethane (5 mL). The reaction mixture was subjected to reaction at 25° C. for 12 hours. The reaction was quenched with 10 mL of saturated aqueous sodium sulfite. The aqueous phase was separated and extracted three times with 20 mL of dichloromethane, and the organic phases were combined and washed twice with 20 mL of saturated brine. The organic phase was dried over anhydrous sodium sulfate, filtered and concentrated to give compound 5-14. MS [ESI, M+1]: 630.3.

Step I: 0.1 mL of trifluoroacetic acid was added to a solution of compound 5-14 (20 mg, 31.74 μmol, 1 eq.) in dichloromethane (2 mL). The reaction mixture was subjected to reaction at 25° C. for 1 hour, and concentrated to give a crude product. The crude product was separated by prep-HPLC (water (10 mM ammonium bicarbonate)/acetonitrile system) 45-75%) to give compound 5. MS [ESI, M+1]: 530.3.

1H NMR (400 MHz, METHANOL-d$_4$) δ=8.28 (dd, J=1.6, 4.8 Hz, 1H), 8.01 (dd, J=1.6, 8.0 Hz, 1H), 7.70 (d, J=2.0 Hz, 1H), 7.33-7.20 (m, 7H), 6.78 (td, J=5.6, 15.2 Hz, 1H), 6.60-6.53 (m, 2H), 4.26 (t, J=5.4 Hz, 2H), 3.44 (dd, J=1.5, 5.6 Hz, 2H), 3.09 (s, 3H), 2.98 (s, 3H), 2.96-2.88 (m, 2H), 2.59-2.50 (m, 2H), 0.98 (t, J=7.2 Hz, 3H).

Example 6

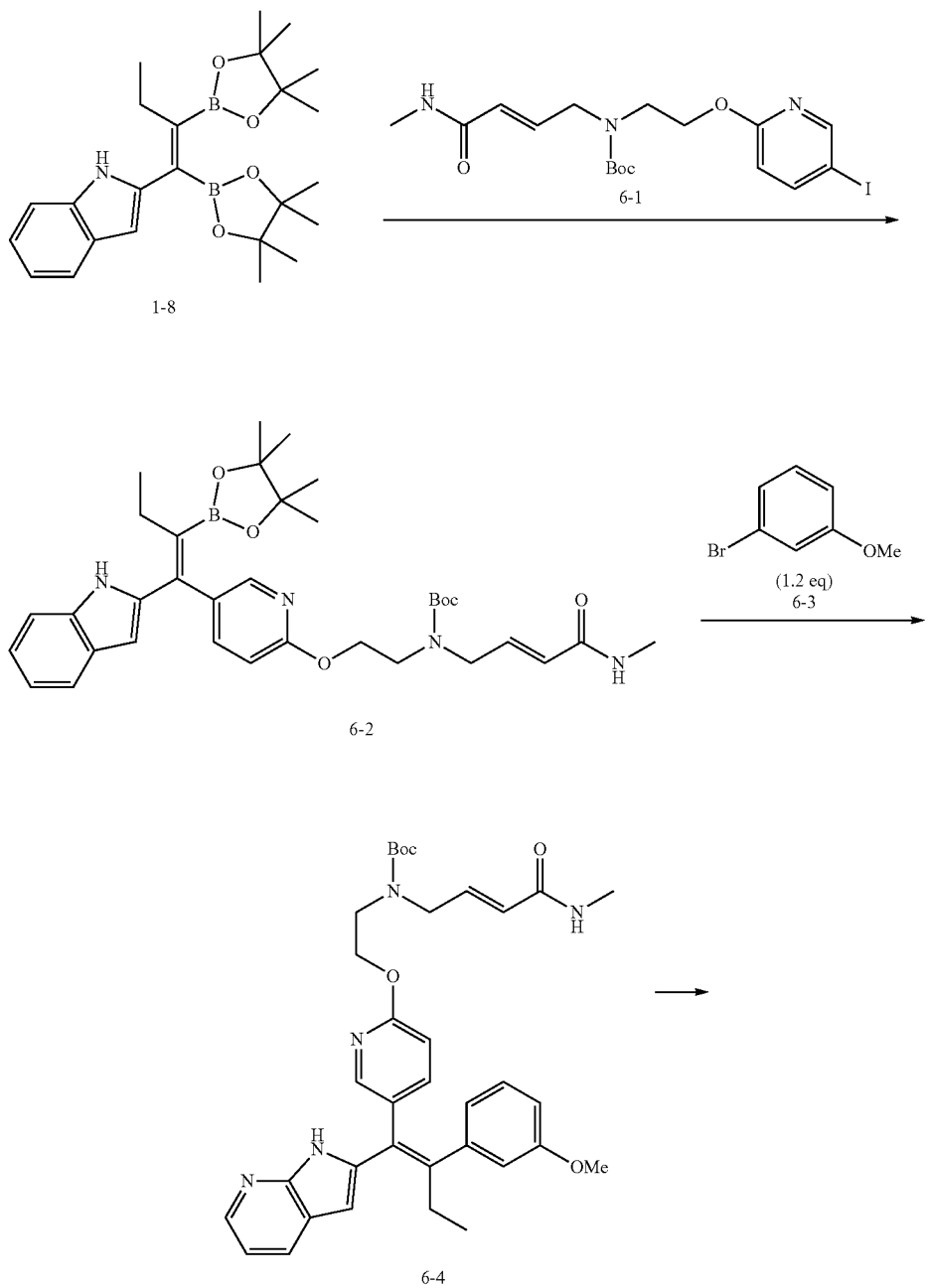

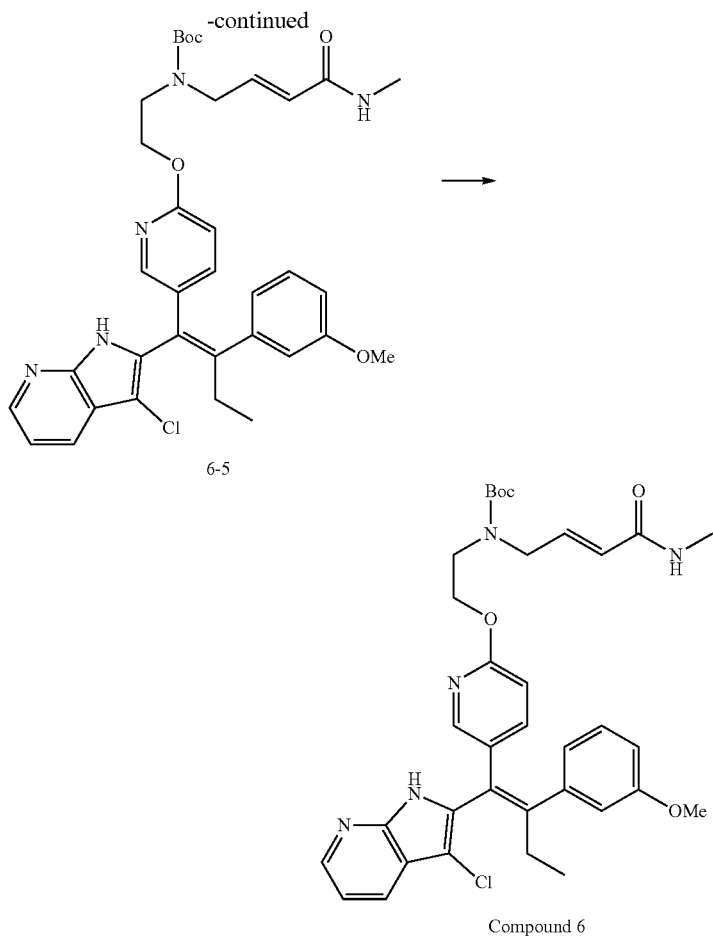

Step A: Compound 6-1 (1.15 g, 2.49 mmol, 1 eq.), cesium carbonate (1.62 g, 4.99 mmol, 2 eq.) and bis(triphenylphosphine)palladium(II) dichloride (87.49 mg, 124.65 μmol, 0.05 eq.) were added to a solution of compound 1-8 (1.50 g, 3.54 mmol, 1.42 eq.) in 2-methyltetrahydrofuran (10 mL) at room temperature. The reaction system was purged with nitrogen three times before water (1 mL) was added. The reaction mixture was subjected to reaction at 30° C. for 12 hours in nitrogen atmosphere to give compound 6-2 for direct use in the next reaction without purification.

Step B: 1-Bromo-3-methoxybenzene (558.81 mg, 2.99 mmol, 377.57 μL, 1.2 eq.), aqueous potassium hydroxide (4 M, 4.36 mL, 7 eq.) and bis(triphenylphosphine)palladium (II) dichloride (87.38 mg, 124.49 μmol, 0.05 eq.) were added to a solution of compound 6-2 (1.07 g, 1.66 mmol, 1.00 eq.) in 2-methyltetrahydrofuran (10 mL). The reaction system was purged with nitrogen three times, and subjected to reaction at 85° C. for 12 hours in nitrogen atmosphere. After cooling to room temperature, the reaction mixture was added with 30 mL of water. The aqueous phase was extracted three times with 50 mL of ethyl acetate, and the organic phases were combined and washed twice with 50 mL of saturated brine. The organic phase was dried over anhydrous sodium sulfate, filtered and concentrated to give a crude product. The crude product was separated by silica gel column chromatography (petroleum ether:ethyl acetate=1:0-4:5, v/v) to give compound 6-4. MS [ESI, M+1]: 611.3.

Step C: N-chlorosuccinimide (314.84 mg, 2.36 mmol, 1.2 eq.) was added to a solution of compound 6-4 (1.2 g, 1.96 mmol, 1 eq.) in dichloromethane (20 mL). The reaction mixture was subjected to reaction at 25° C. for 12 hours, and then washed with 5 mL of saturated aqueous sodium sulfite. The organic phase was dried over anhydrous sodium sulfate, filtered and concentrated to give compound 6-5. MS [ESI, M+1]: 645.2.

Step D: 5 mL of trifluoroacetic acid was added to a solution of compound 6-5 (450 mg, 697.47 μmol, 1 eq.) in dichloromethane (5 mL). The reaction mixture was subjected to reaction at 25° C. for 1 hour in nitrogen atmosphere, and concentrated to give a crude product. The crude product was separated by prep-HPLC (water (0.05% hydrochloric acid, v/v)/acetonitrile system) to give compound 6. MS [ESI, M+1]: 545.2.

$^1$H NMR (400 MHz, DMSO-$d_6$) δ=11.93-11.15 (m, 1H), 9.43 (br s, 2H), 8.24 (br d, J=4.8 Hz, 1H), 7.77-7.62 (m, 1H), 7.48 (d, J=7.6 Hz, 1H), 7.39 (d, J=8.4 Hz, 1H), 7.33-7.26 (m, 1H), 7.25 (d, J=3.2 Hz, 1H), 7.26-7.22 (m, 1H), 7.22-7.17 (m, 2H), 7.15-7.08 (m, 1H), 6.84-6.78 (m, 1H), 6.76 (br d, J=2.8 Hz, 1H), 6.19 (d, J=15.4 Hz, 1H), 4.47-4.34 (m, 2H), 3.73 (br d, J=5.6 Hz, 2H), 3.69 (s, 3H), 3.22 (br s, 2H), 2.64 (d, J=4.8 Hz, 3H), 2.47-2.40 (m, 2H), 1.12-0.72 (m, 3H).

Example 7
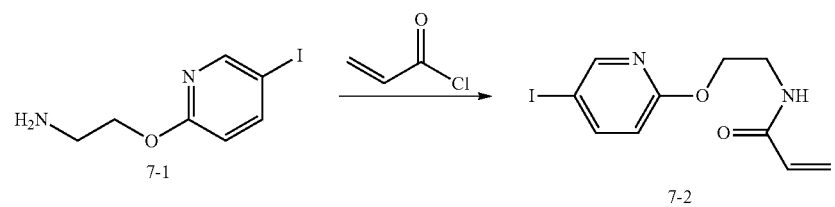
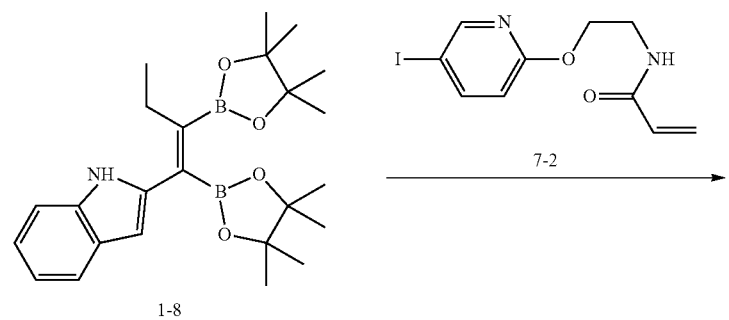
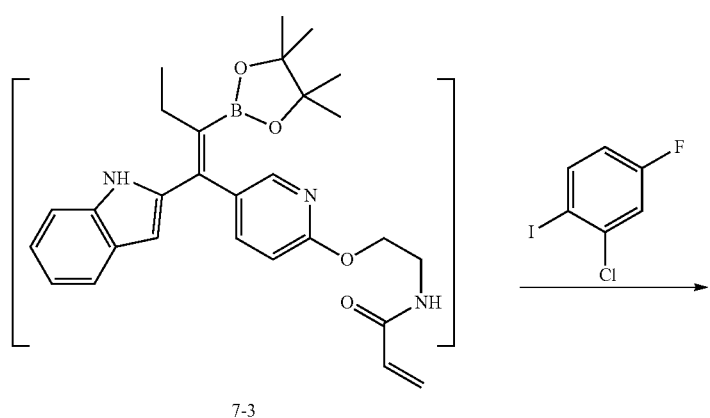
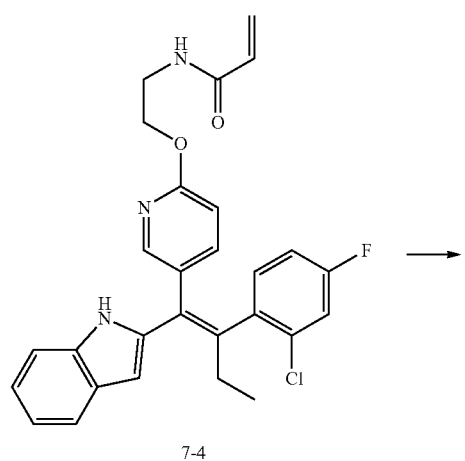

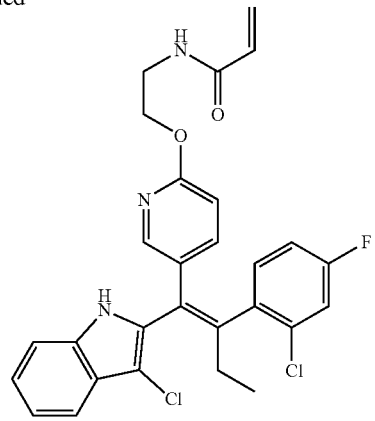

7

Step A: Sodium carbonate (2.41 g, 22.72 mmol, 5 eq.) was added to a solution of compound 7-1 (1.2 g, 4.54 mmol, 1 eq.) in dichloromethane (10 mL) and N,N-dimethylformamide (1 mL). The reaction system was subjected to reaction at 25° C. for 15 minutes, cooled to 0° C., added with acryloyl chloride (1.23 g, 13.63 mmol, 1.11 mL, 3 eq.) and subjected to reaction at 25° C. for 11 hours and 45 minutes. The system was added with 10 mL of water, and extracted three times with 20 mL of a mixture of dichloromethane and methanol (10/1, v/v). The organic phases were combined, washed once with 10 mL of saturated brine, dried over sodium sulfate, filtered and concentrated to give a crude product of compound 7-2. MS [ESI, M+1]: 318.9 Step B: Pd(PPh$_3$)$_2$Cl$_2$ (73.01 mg, 104.01 μmol, 0.05 eq.) and Cs$_2$CO$_3$ (1.36 g, 4.16 mmol, 2 eq.) were added to a solution of compounds 1-8 (1.25 g, 2.95 mmol, 1.42 eq.) and 7-2 (661.75 mg, 2.08 mmol, 1 eq.) in 2-methyltetrahydrofuran (5 mL). The reaction system was purged with nitrogen three times, added with 0.2 mL of water, and subjected to reaction at 30° C. for 12 hours to give compound 7-3 for direct use in the next reaction without purification. MS [ESI, M+1]: 488.3

Step C: Aqueous potassium hydroxide (4 M, 4.36 mL, 7 eq.) and bis(triphenylphosphine)palladium(II) dichloride (72.72 mg, 103.61 μmol, 0.05 eq.) were added to a solution of compound 7-3 (1.01 g, 2.07 mmol, 1 eq.) and 2-chloro-4-fluoroiodobenzene (637.69 mg, 2.49 mmol, 1.2 eq.) in 2-methyltetrahydrofuran (5 mL). The reaction system was purged with nitrogen three times, and subjected to reaction at 85° C. for 12 hours in nitrogen atmosphere. The reaction system was added with 30 mL of water, and extracted three times with 50 mL of ethyl acetate. The organic phases were combined and washed twice with 50 mL of saturated brine. The organic phase was dried over anhydrous sodium sulfate, filtered and concentrated to give a crude product. The crude product was separated by silica gel column chromatography (petroleum ether:ethyl acetate=1:0-2:3, v/v) to give compound 7-4 (360 mg, 734.74 μmol). MS [ESI, M+1]: 490.2

Step D: N-chlorosuccinimide (52.33 mg, 391.86 μmol, 1.2 eq.) was added to a solution of compound 7-4 (160 mg, 326.55 μmol, 1 eq.) in dichloromethane (10 mL). The reaction system was purged with nitrogen 3 times, subjected to reaction at 25° C. for 12 hours, and diluted with 10 mL of dichloromethane. The organic phase was washed twice with 20 mL of saturated brine, dried over anhydrous sodium sulfate, filtered, and concentrated to give a crude product. The crude product was separated by prep-HPLC (water (0.225% formic acid)-acetonitrile system, v/v) to give compound 7. MS [ESI, M+1]: 524.2

$^1$H NMR (400 MHz, DMSO-d$_6$) δ=11.47 (s, 1H), 8.24 (br t, J=5.3 Hz, 1H), 7.72 (d, J=2.3 Hz, 1H), 7.68-7.54 (m, 1H), 7.52-7.34 (m, 3H), 7.26-7.11 (m, 4H), 6.61 (d, J=8.7 Hz, 1H), 6.20 (dd, J=10.0, 17.1 Hz, 1H), 6.06 (dd, J=2.3, 17.1 Hz, 1H), 5.58-5.54 (m, 1H), 4.16 (t, J=5.6 Hz, 2H), 3.47-3.36 (m, 2H), 2.48-2.39 (m, 2H), 0.90 (t, J=7.5 Hz, 3H).

Example 8

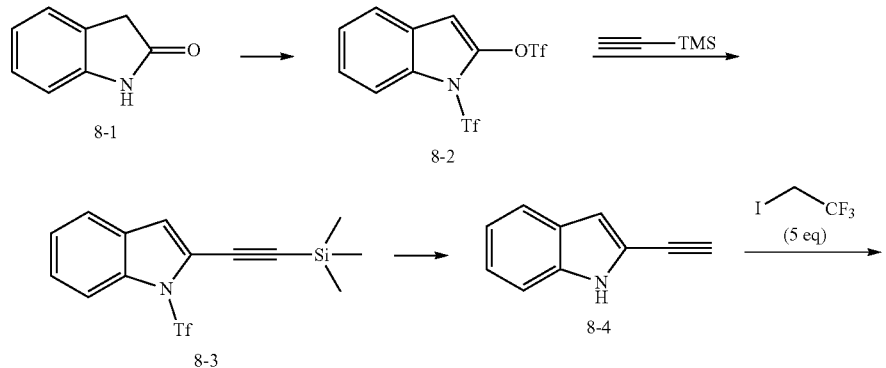

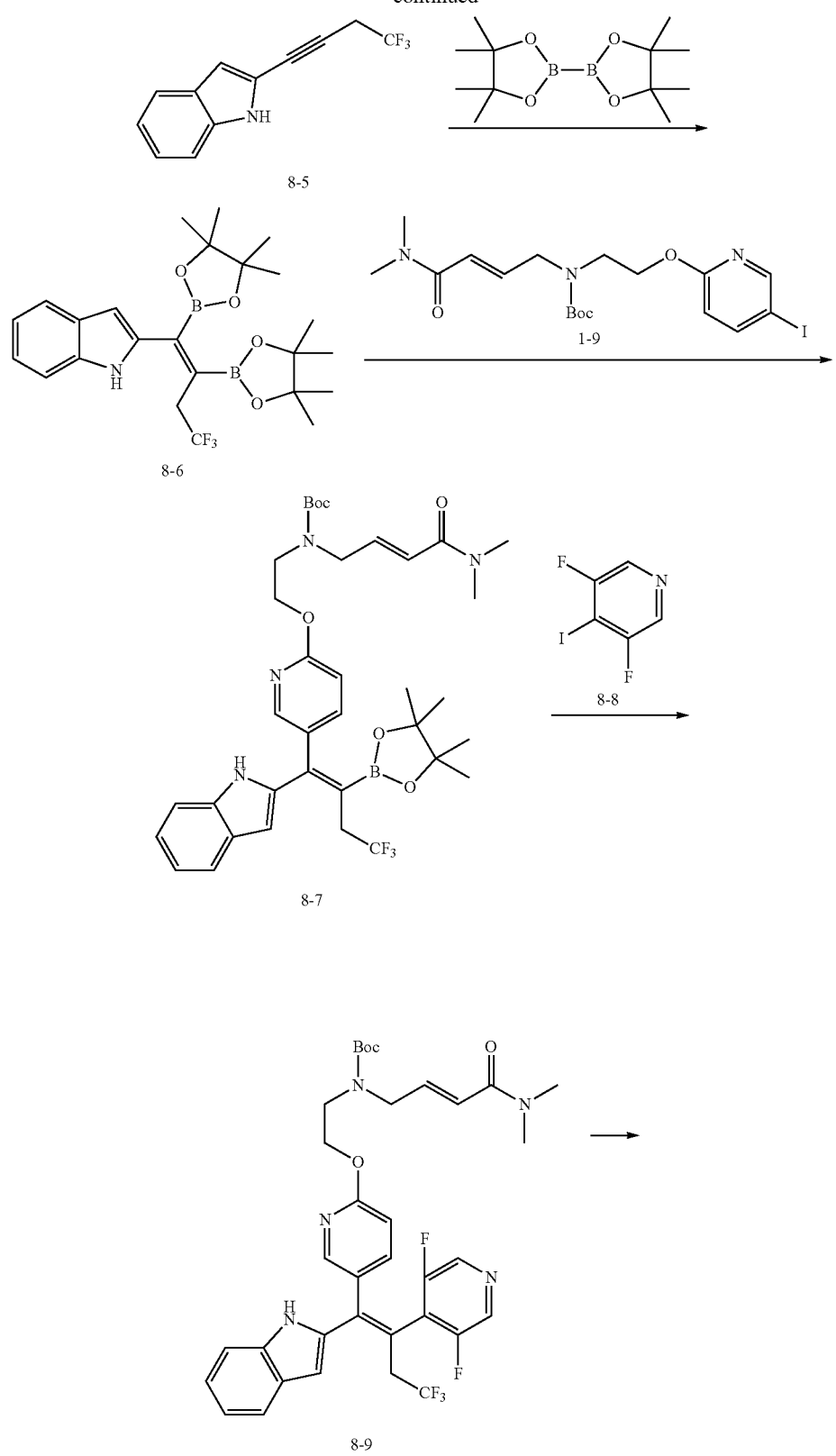

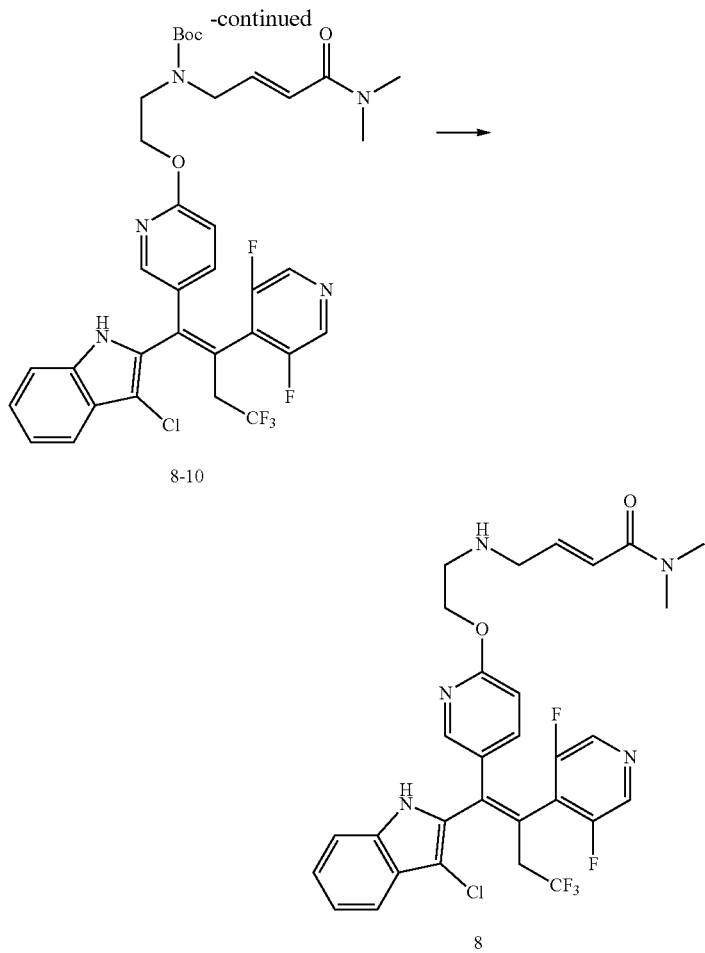

Step A: A solution of indolin-2-one 8-1 (10 g, 75.10 mmol, 1 eq.) and triethylamine (22.80 g, 225.31 mmol, 31.36 mL, 3 eq.) in dichloromethane (100 mL) was purged with nitrogen three times, cooled to −70° C., and added dropwise with trifluoromethanesulfonic anhydride (46.62 g, 165.23 mmol, 27.26 mL, 2.2 eq.) while keeping the temperature below −60° C. After the dropwise addition, the reaction system was subjected to reaction at −60° C. for 2 hours. 1 M hydrochloric acid was added dropwise and slowly to the system to adjust the pH value to 1 while keeping the temperature below 30° C. The reaction system was washed twice with 100 mL of 0.5 M hydrochloric acid and once with 100 mL of saturated brine. The organic phase was dried over anhydrous sodium sulfate and concentrated to give a crude product of compound 8-2.

$^1$H NMR (400 MHz, CDCl$_3$) δ ppm 7.86 (d, J=8.4 Hz, 1H), 7.54 (d, J=8.8 Hz, 1H), 7.35-7.40 (m, 2H), 6.61 (s, 1H).

Step B: Pd(PPh$_3$)$_4$(4.36 g, 3.78 mmol, 0.1 eq.) and copper(I) iodide (719.09 mg, 3.78 mmol, 0.1 eq.) were added to a solution of compound 8-2 (15 g, 37.76 mmol, 1 eq.) in triethylamine (150 mL). The system was purged with nitrogen three times, and added with trimethylsilylacetylene (18.54 g, 188.80 mmol, 26.15 mL, 5 eq.). In nitrogen atmosphere, the reaction system was subjected to reaction a 65° C. for 12 hours. The reaction system was added with 100 mL of water for quenching, and extracted 3 times with 150 mL of ethyl acetate. The organic phases were combined, washed twice with 100 mL of saturated brine, and dried over sodium sulfate. The reaction mixture was filtered and concentrated to give a crude product. The crude product was separated by silica gel column chromatography (petroleum ether:ethyl acetate=1:0-10:1, v/v) to give compound 8-3.

$^1$H NMR (400 MHz, CDCl$_3$) δ ppm 7.97 (d, J=8.8 Hz, 1H), 7.57 (d, J=8.0 Hz, 1H), 7.37-7.44 (m, 2H), 7.07 (s, 1H), 0.31 (s, 9H).

Step C: Potassium carbonate (6.72 g, 48.64 mmol, 2 eq.) was added to a solution of compound 8-3 (8.4 g, 24.32 mmol, 1 eq.) in methanol (50 mL), and the reaction system was subjected to reaction at 70° C. for 0.5 hours. After cooling to room temperature, the reaction was quenched with 100 mL of water, and the reaction system was extracted three times with 150 mL of dichloromethane. The organic phases were combined, washed twice with 100 mL of saturated brine, dried over anhydrous sodium sulfate, filtered and concentrated to give a crude product of compound 8-4.

$^1$H NMR (400 MHz, CDCl3) ppm 8.19 (s, 1H), 7.51 (d, J=8.4 Hz, 1H), 7.24 (d, J=7.6 Hz, 1H), 7.17-7.19 (m, 1H), 7.06-7.08 (m, 1H), 6.75 (s, 1H), 3.24 (s, 1H).

Step D: Pd$_2$(dba)$_3$ (648.67 mg, 708.37 μmol, 0.05 eq.), bis[(2-diphenylphosphino)phenyl] ether (DPEphos, 1.53 g, 2.83 mmol, 0.2 eq.) and DABCO (3.18 g, 28.33 mmol, 3.12 mL, 2 eq.) were added to a dry flask. The reaction system was purged with nitrogen three times, and sequentially added with compound 8-4 (2 g, 14.17 mmol, 1 eq.), 1,1,1-trifluoroiodoethane (2.97 g, 14.17 mmol, 1.39 mL, 1 eq.) and toluene (20 mL) in nitrogen atmosphere. The reaction mixture was subjected to reaction at 80° C. for 12 hours, filtered and washed with 50 mL of ethyl acetate. The organic phase was concentrated to give a crude product. The crude product was separated by silica gel column chromatography (petroleum ether:ethyl acetate=1:0-5/1, v/v) to give compound 8-5. MS [ESI, M+1]: 224.1

Step E: Tetrakis(triphenylphosphine)platinum(0) (55.75 mg, 44.80 μmol, 0.02 eq.) was added to a solution of compound 8-5 (0.5 g, 2.24 mmol, 1 eq.) and bis(pinacolato)diboron (568.87 mg, 2.24 mmol, 1 eq.) in 2-methyltetrahydrofuran (10 mL). The reaction mixture was subjected to reaction at 85° C. for 12 hours in nitrogen atmosphere and then cooled to room temperature to give compound 8-6 for direct use in the next reaction without purification.

Step F: Compound 1-9 (532.97 mg, 1.12 mmol, 0.50 eq.), Pd(PPh$_3$)$_2$Cl$_2$ (78.70 mg, 112.13 μmol, 0.05 eq.) and cesium carbonate (1.46 g, 4.49 mmol, 2 eq.) were added to a solution of compound 8-6 (1.07 g, 2.24 mmol, 1 eq.) in 2-methyltetrahydrofuran (10 mL). The reaction system was purged with nitrogen three times, added with 2.5 mL of water, and subjected to reaction at 30° C. for 12 hours to give compound 8-7 for direct use in the next reaction without purification.

Step G: Compound 8-8 (649.89 mg, 2.70 mmol, 1.2 eq.), aqueous potassium hydroxide (4 M, 3.93 mL, 7 eq.) and Pd(PPh$_3$)$_2$Cl$_2$ (78.87 mg, 112.37 μmol, 0.05 eq.) were added to a solution of compound 8-7 (1.57 g, 2.25 mmol, 1 eq.) in 2-methyltetrahydrofuran (10 mL). The reaction system was purged with nitrogen three times, and subjected to reaction at 85° C. for 12 hours. After cooling to room temperature, the reaction system was diluted with 10 mL of water and 10 mL of ethyl acetate. The aqueous phase was extracted 3 times with 10 mL of ethyl acetate. The organic phases were combined, washed with saturated brine, dried over anhydrous sodium sulfate, filtered and concentrated to give a crude product. The crude product was separated by silica gel column chromatography to give compound 8-9. MS [ESI, M+1]: 686.2

Step H: A solution of compound 8-9 (500 mg, 729.20 μmol, 1 eq.) and N-chlorosuccinimide (116.84 mg, 875.04 μmol, 1.2 eq.) in dichloromethane (5 mL) was subjected to reaction at 20° C. for 12 hours. The reaction was quenched with 10 mL of water, and the aqueous phase was extracted 3 times with 20 mL of dichloromethane. The organic phases were combined, washed twice with 20 mL of saturated brine, dried over anhydrous sodium sulfate, filtered and concentrated to give a crude product of compound 8-10. MS [ESI, M+1]: 720.4

Step I: Trifluoroacetic acid (71.25 mg, 624.89 μmol, 46.27 μL, 1 eq.) was added to a solution of compound 8-10 (450 mg, 624.89 μmol, 1 eq.) in dichloromethane (5 mL). The reaction mixture was subjected to reaction at 20° C. for 1 hour, and concentrated to give a crude product. The crude product was separated sequentially by prep-HPLC (water (0.025% formic acid, v/v)/acetonitrile system), thin layer chromatography (petroleum ether/ethyl acetate=0/1, v/v) and prep-HPLC (water (0.025% formic acid, v/v)/acetonitrile system) to give compound 8. MS [ESI, M+1]: 620.2

$^1$H NMR (400 MHz, DMSO-d$_6$) δ ppm 11.79 (s, 1H) 8.50-8.60 (m, 2H) 8.23 (s, 1H) 7.85 (d, J=2.4 Hz, 1H) 7.56 (d, J=7.6 Hz, 1H) 7.34-7.47 (m, 2H) 7.12-7.29 (m, 2H) 6.70 (d, J=8.4 Hz, 1H) 6.55-6.63 (m, 1H) 6.46-6.53 (m, 1H) 4.18 (t, J=5.6 Hz, 2H) 3.50-3.63 (m, 2H) 3.31-3.32 (m, 2H) 2.97 (s, 3H) 2.83-2.87 (m, 3H) 2.77 (t, J=5.6 Hz, 2H).

Example 9

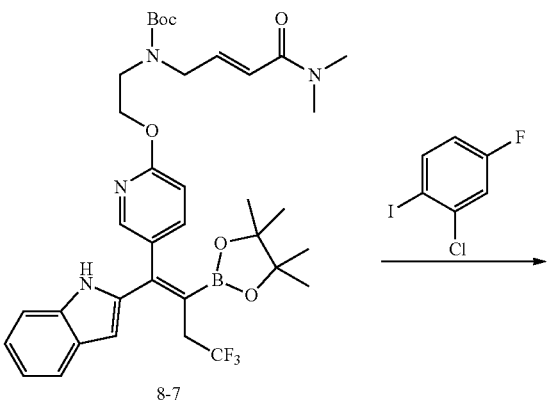

8-7

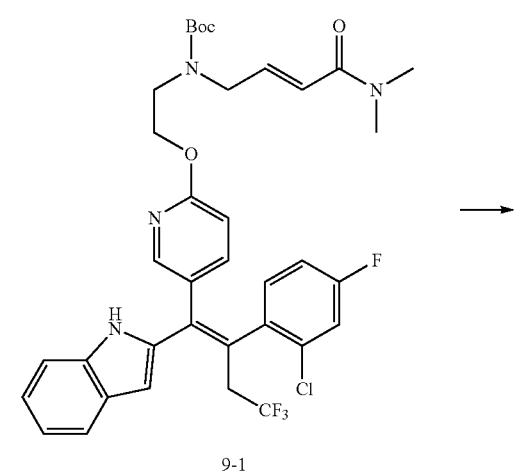

9-1

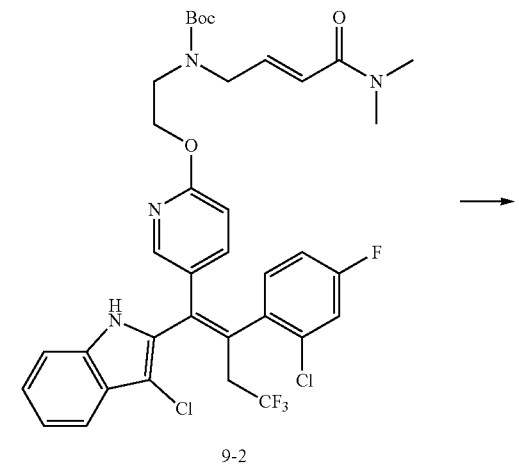

9-2

83
-continued

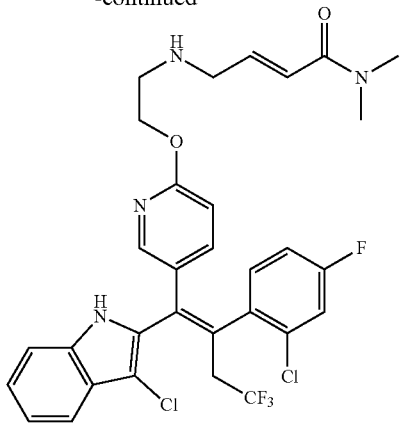
9

84
Example 10

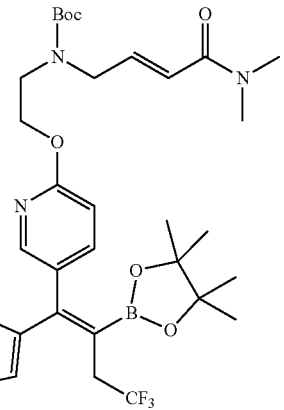
8-7

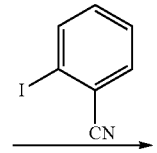

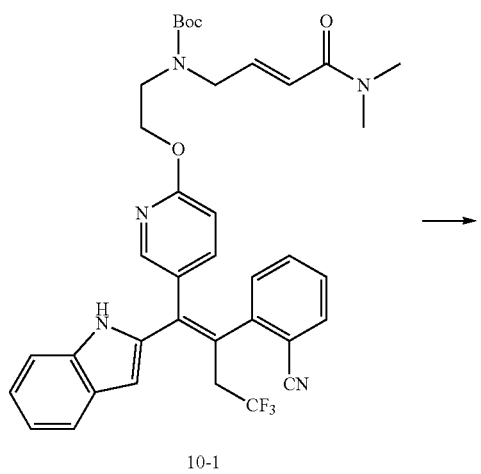
10-1

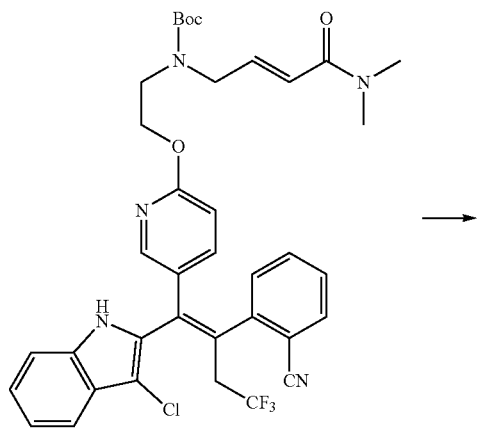
10-2

Step A: 2-Chloro-4-fluoroiodobenzene (692.40 mg, 2.70 mmol, 1.2 eq.), aqueous potassium hydroxide (4 M, 3.93 mL, 7 eq.) and Pd(PPh$_3$)$_2$Cl$_2$ (78.87 mg, 112.37 μmol, 0.05 eq.) were added to a solution of compound 8-7 (1.57 g, 2.25 mmol, 1 eq.) in 2-methyltetrahydrofuran (10 mL). The reaction system was purged with nitrogen three times, and subjected to reaction at 85° C. for 12 hours. After cooling to room temperature, the reaction system was diluted with 10 mL of water and 10 mL of ethyl acetate. The aqueous phase was extracted 3 times with 10 mL of ethyl acetate. The organic phases were combined, washed with saturated brine, dried over anhydrous sodium sulfate, filtered and concentrated to give a crude product. The crude product was separated by silica gel column chromatography to give compound 9-1. MS [ESI, M+1]: 701.2.

Step B: A solution of compound 9-1 (200 mg, 285.25 μmol, 1 eq.) and N-chlorosuccinimide (45.71 mg, 342.30 μmol, 1.2 eq.) in dichloromethane (10 mL) was subjected to reaction at 20° C. for 12 hours. The reaction was quenched with 10 mL of water, and the aqueous phase was extracted 3 times with 20 mL of dichloromethane. The organic phases were combined, washed twice with 20 mL of saturated brine, dried over anhydrous sodium sulfate, filtered and concentrated to give a crude product of compound 9-2. MS [ESI, M+1]: 735.1.

Step C: Trifluoroacetic acid (3.08 g, 27.01 mmol, 2 mL, 132.47 eq.) was added to a solution of compound 9-2 (150 mg, 203.92 μmol, 1 eq.) in dichloromethane (2 mL). The reaction mixture was subjected to reaction at 20° C. for 1 hour, and concentrated to give a crude product. The crude product was separated twice by prep-HPLC (water (0.025% formic acid, v/v)/acetonitrile system) to give compound 9. MS [ESI, M+1]: 635.2.

$^1$H NMR (EW16419-73-P1A, 400 MHz, DMSO-d$_6$) δ ppm 11.66 (s, 1H) 7.79 (d, J=2.00 Hz, 1H) 7.53 (d, J=7.6 Hz, 1H) 7.42-7.49 (m, 3H) 7.21-7.33 (m, 3H) 7.13-7.19 (m, 1H) 6.55-6.67 (m, 2H) 6.46-6.53 (m, 1H) 4.16 (t, J=5.6 Hz, 2H) 3.41-3.62 (m, 2H) 3.30-3.31 (m, 2H) 2.97 (s, 3H) 2.83 (s, 3H) 2.77 (t, J=5.6 Hz, 2H).

85
-continued

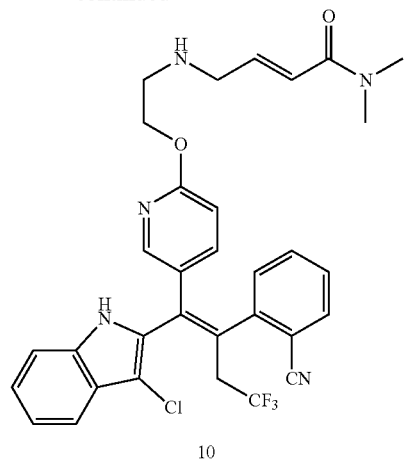

10

Step A: o-Iodobenzonitrile (104.22 mg, 572.59 μmol, 1 eq.), aqueous potassium hydroxide (4 M, 715.74 uL, 5 eq.) and Pd(PPh₃)₂Cl₂ (20.10 mg, 28.63 μmol, 0.05 eq.) were added to a solution of compound 8-7 (400 mg, 572.59 μmol, 1 eq.) in 2-methyltetrahydrofuran (10 mL) and water (2.5 mL). The reaction system was purged with nitrogen three times, and subjected to reaction at 85° C. for 12 hours. After cooling to room temperature, the reaction system was diluted with 10 mL of water and 10 mL of ethyl acetate. The aqueous phase was extracted 3 times with 10 mL of ethyl acetate. The organic phases were combined, washed with 20 mL of saturated brine, dried over anhydrous sodium sulfate, filtered and concentrated to give a crude product. The crude product was separated by silica gel thin layer chromatography to give compound 10-1. MS [ESI, M+1]: 674.2

Step B: A solution of compound 10-1 (35 mg, 51.95 μmol, 1 eq.) and N-chlorosuccinimide (8.32 mg, 62.34 μmol, 1.2 eq.) in dichloromethane (5 mL) was subjected to reaction at 20° C. for 12 hours. The reaction was quenched with 10 mL of saturated aqueous sodium sulfite, and the aqueous phase was extracted 3 times with 20 mL of dichloromethane. The organic phases were combined, washed twice with 20 mL of saturated brine, dried over anhydrous sodium sulfate, filtered and concentrated to give a crude product of compound 10-2. MS [ESI, M+1]: 708.2

Step C: Trifluoroacetic acid (770.00 mg, 6.75 mmol, 0.5 mL, 159.41 eq.) was added to a solution of compound 10-2 (30 mg, 42.36 μmol, 1 eq.) in dichloromethane (3 mL). The reaction mixture was subjected to reaction at 20° C. for 1 hour, and concentrated to give a crude product. The crude product was separated by prep-HPLC (water (0.025% formic acid, v/v)/acetonitrile system) and prep-HPLC (water (0.05% aqueous ammonia, v/v)/acetonitrile system) to give compound 10. MS [ESI, M+1]: 608.3

¹H NMR (EW16419-216-P1A, 400 MHz, DMSO-d₆) δ=11.59 (s, 1H), 7.81-7.68 (m, 4H), 7.60-7.42 (m, 3H), 7.32-7.12 (m, 3H), 6.66-6.43 (m, 3H), 4.21-4.11 (m, 2H), 3.47-3.43 (m, 2H), 3.48-3.41 (m, 2H), 2.96 (s, 3H), 2.89 (s, 3H), 2.76 (t, J=6.0 Hz, 2H).

86
Example 11

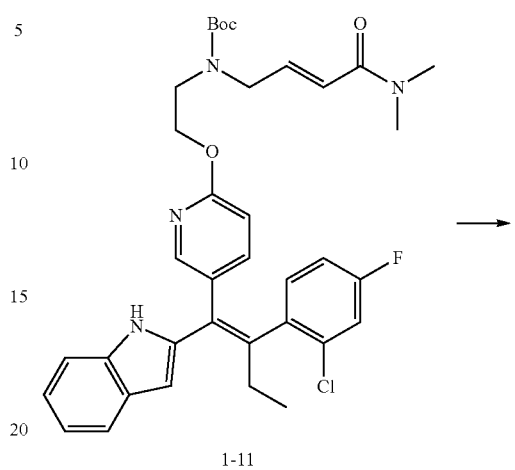

1-11

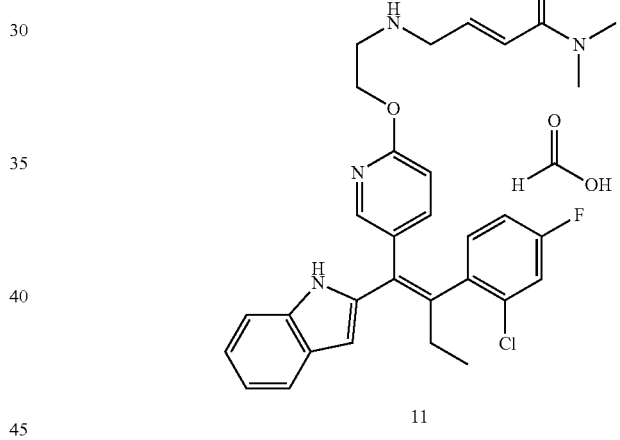

11

Step A: 1 mL of trifluoroacetic acid was added to a solution of compound 11-1 (100 mg, 154.52 μmol, 1 eq.) in dichloromethane (1 mL). The reaction mixture was subjected to reaction at 25° C. for 1 hour in nitrogen atmosphere, and concentrated to give a crude product. The crude product was separated by prep-HPLC (water (0.225% formic acid, v/v)/acetonitrile system) to give compound 11. MS [ESI, M+1]: 547.3

¹H NMR (400 MHz, DMSO-d₆) δ ppm 10.77 (s, 1H) 8.90 (br s, 2H) 7.74 (d, J=2.45 Hz, 1H) 7.57 (d, J=7.46 Hz, 1H) 7.26-7.41 (m, 4H) 7.18 (m, 1H) 7.08 (t, J=7.23 Hz, 1H) 7.01 (t, J=7.04 Hz, 1H) 6.81 (d, J=15.16 Hz, 1H) 6.67 (d, J=8.68 Hz, 1H) 6.52-6.60 (m, 2H) 4.37 (t, J=5.07 Hz, 2H) 3.81 (brd, J=4.40 Hz, 2H) 3.04 (s, 3H) 2.88 (s, 3H) 2.59-2.75 (m, 2H) 2.31-2.44 (m, 2H) 1.01 (t, J=7.52 Hz, 3H).

Example 12

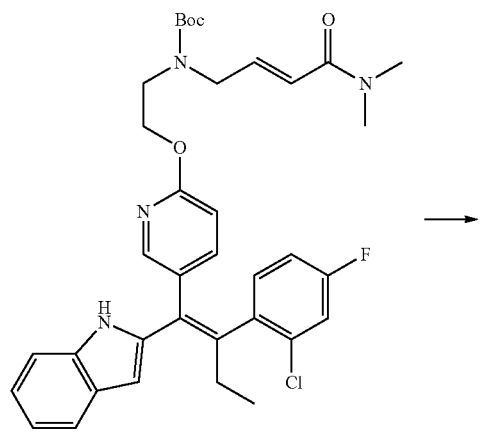

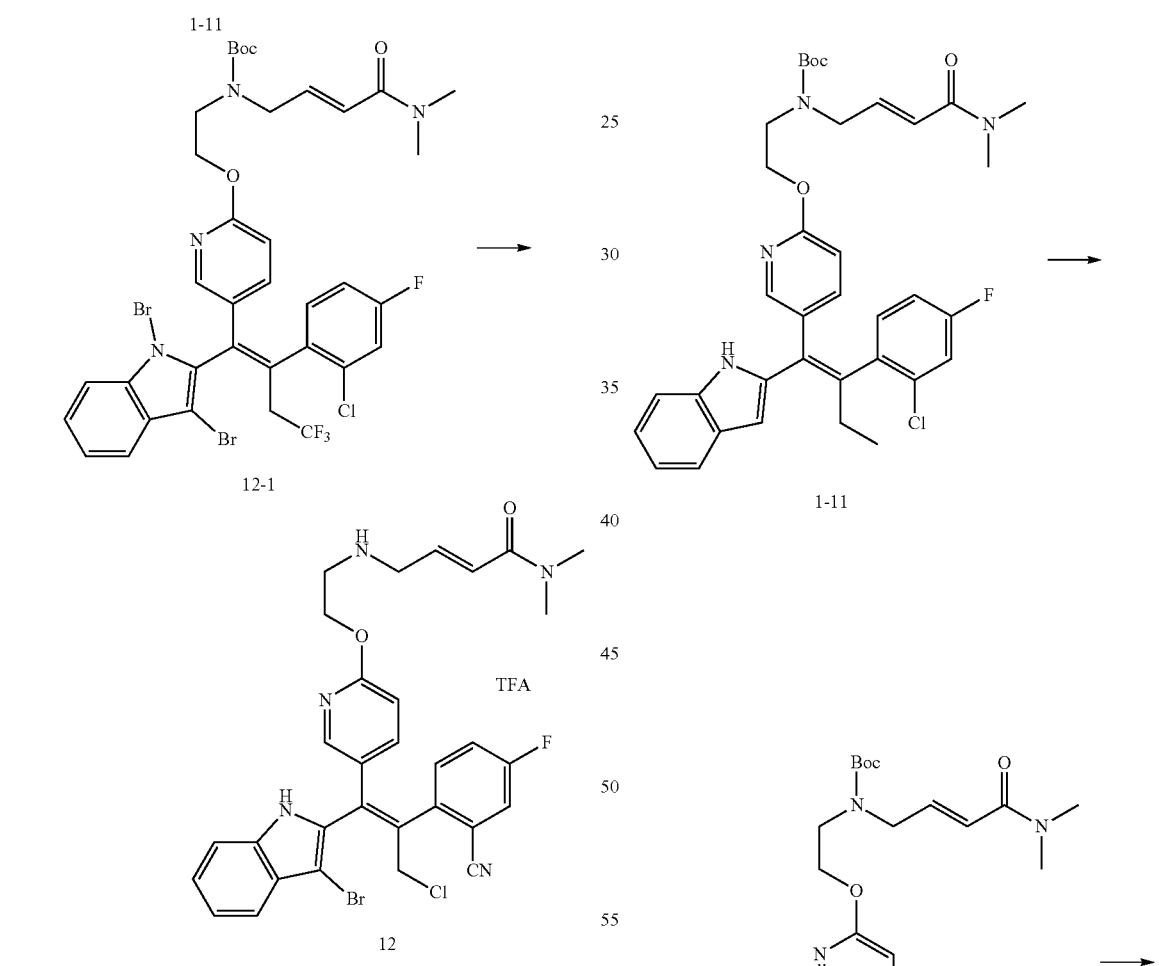

Step A: N-bromosuccinimide (33.00 mg, 185.42 μmol, 1.2 eq.) was added to a solution of compound 11-1 (100 mg, 154.52 μmol, 1 eq.) in dichloromethane (3 mL). The reaction system was purged with nitrogen three times, and subjected to reaction at 25° C. for 2 hours. The reaction mixture was added with 10 mL of dichloromethane. The organic phase was washed twice with 20 mL of saturated brine, dried over anhydrous sodium sulfate, filtered and concentrated to give a crude product of compound 12-1. MS [ESI, M+1]: 804.9

Step B: 1 mL of trifluoroacetic acid was added to a solution of compound 12-1 (140.00 mg, 173.92 μmol, 1 eq.) in dichloromethane (1 mL). The reaction mixture was subjected to reaction at 25° C. for 1 hour in nitrogen atmosphere, and concentrated to give a crude product. The crude product was separated by prep-HPLC (water (0.1% trifluoroacetic acid, v/v)/acetonitrile system) to give compound 12. MS [ESI, M+1]: 627.1

$^1$H NMR (400 MHz, DMSO-$d_6$) δ ppm 11.70 (s, 1H) 8.91 (br s, 2H) 7.78 (d, J=2.02 Hz, 1H) 7.31-7.38 (m, 1H) 7.35-7.28 (m, 2H) 7.25-7.18 (m, 2H) 7.12-7.27 (m, 2H) 7.19 (d, J=13.28 Hz, 1H) 6.79 (d, J=15.18 Hz, 1H) 6.68 (d, J=8.54 Hz, 1H) 6.54 (m, 1H) 4.35 (br t, J=4.96 Hz, 2H) 3.97 (br s, 2H) 3.79 (br d, J=5.14 Hz, 2H) 3.02 (s, 3H) 2.87 (s, 3H) 2.36-2.47 (m, 2H) 0.90 (t, J=7.56 Hz, 3H).

Example 13

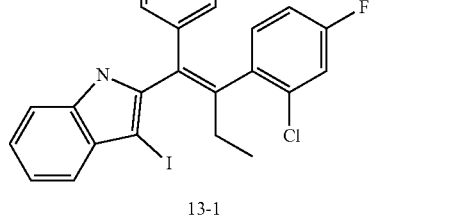

Example 14

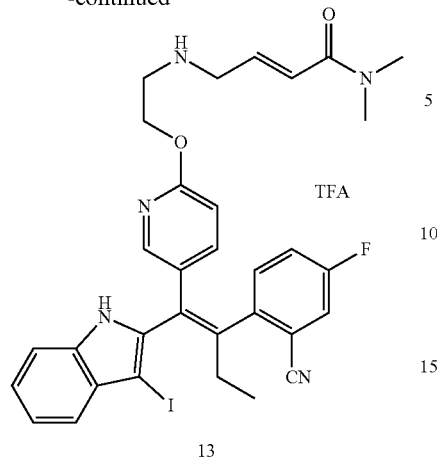

13

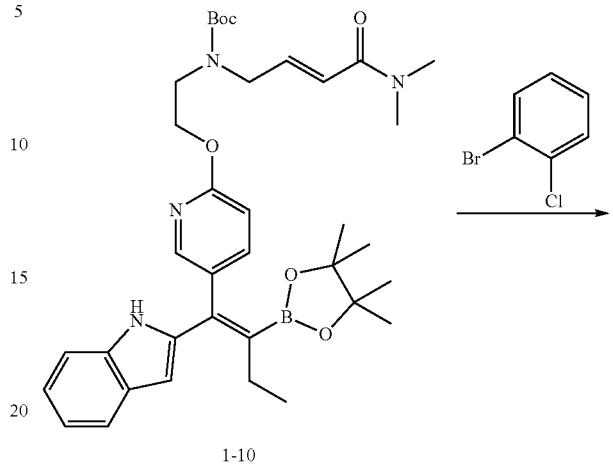

1-10

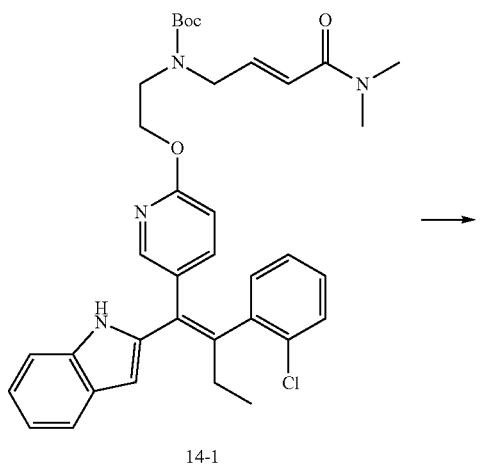

14-1

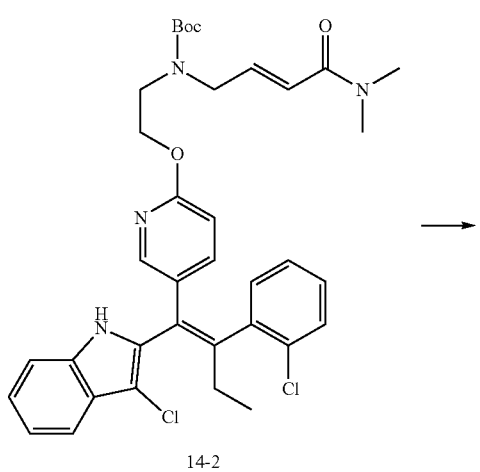

14-2

Step A: N-iodosuccinimide (83.43 mg, 370.84 µmol, 1.2 eq.) was added to a solution of compound 11-1 (200 mg, 309.03 µmol, 1 eq.) in dichloromethane (10 mL). The reaction system was purged with nitrogen three times, and subjected to reaction at 25° C. for 2 hours. The reaction was quenched with 5 mL of saturated aqueous sodium sulfite. The reaction mixture was added with 10 mL of dichloromethane. The organic phase was washed twice with 20 mL of saturated brine, dried over anhydrous sodium sulfate, filtered and concentrated to give a crude product of compound 13-1. MS [ESI, M+1]: 773.3.

Step B: 3 mL of trifluoroacetic acid was added to a solution of compound 13-1 (200 mg, 258.71 µmol, 1 eq.) in dichloromethane (3 mL). The reaction mixture was subjected to reaction at 25° C. for 1 hour in nitrogen atmosphere, and concentrated to give a crude product. The crude product was separated by prep-HPLC (water (0.1% trifluoroacetic acid, v/v)/acetonitrile system) to give compound 13. MS [ESI, M+1]: 673.1.

$^1$H NMR (400 MHz, DMSO-$d_6$) δ ppm 11.79 (s, 1H) 8.86 (br s, 2H) 7.81 (m, 1H) 7.47 (d, J=8.84 Hz, 1H) 7.39-7.42 (m, 1H) 7.30-7.37 (m, 1H) 7.27-7.29 (m, 2H) 7.17-7.26 (m, 1H) 7.11-7.15 (m, 1H) 6.88 (d, J=15.18 Hz, 1H) 6.78 (d, J=15.16 Hz, 1H) 6.68 (d, J=8.66 Hz, 1H) 6.54 (m, 1H) 4.36 (t, J=5.02 Hz, 2H) 3.72-3.98 (m, 2H) 3.19-3.44 (m, 2H) 3.02 (s, 3H) 2.87 (s, 3H) 2.30-2.48 (m, 2H) 0.90 (t, J=7.52 Hz, 3H).

-continued

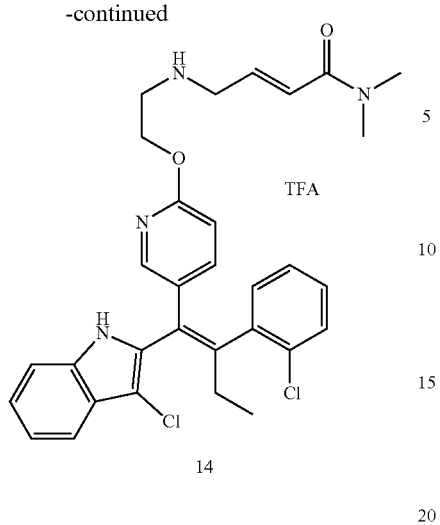

14

Example 15

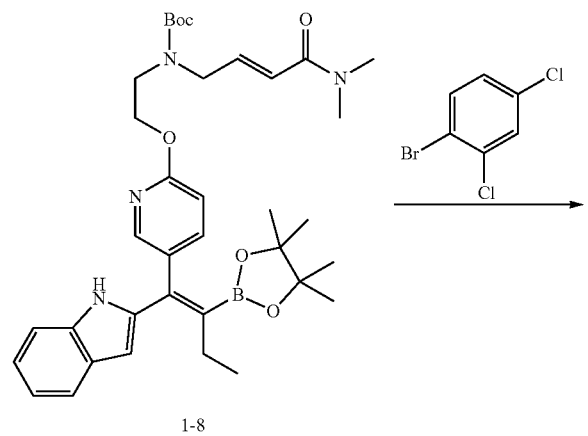

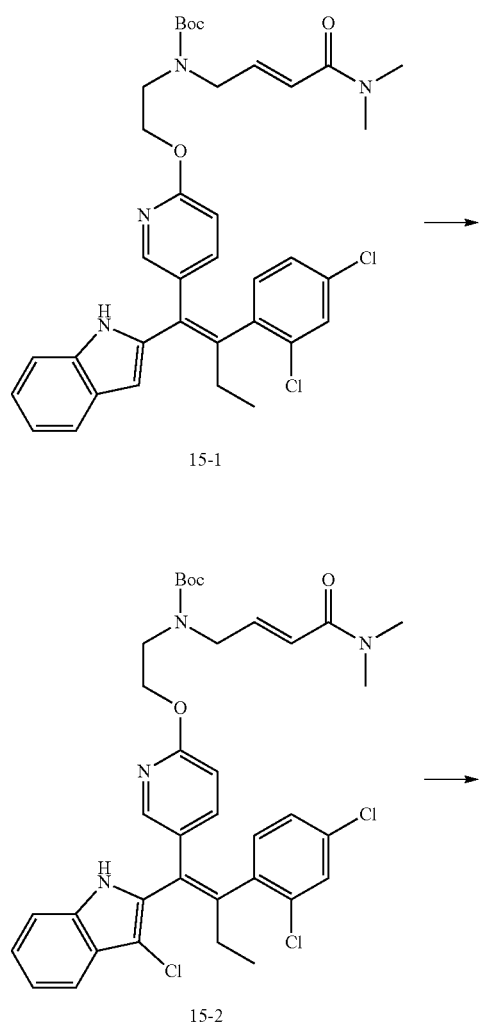

Step A: 1-Bromo-2-chlorobenzene (317.20 mg, 1.66 mmol, 193.42 uL, 1.2 eq.), aqueous potassium hydroxide (4 M, 2.42 mL, 7 eq.) and Pd(PPh$_3$)$_2$Cl$_2$ (48.45 mg, 69.03 μmol, 0.05 eq.) were added to a solution of compound 1-10 (0.89 g, 1.38 mmol, 1 eq.) in 2-methyltetrahydrofuran (10 mL). The reaction system was purged with nitrogen three times, and subjected to reaction at 85° C. for 12 hours. After cooling to room temperature, the reaction system was diluted with 30 mL of water. The aqueous phase was extracted 3 times with 50 mL of ethyl acetate. The organic phases were combined, washed twice with 50 mL of saturated brine, dried over anhydrous sodium sulfate, filtered and concentrated to give a crude product. The crude product was separated by silica gel column chromatography to give compound 14-1. MS [ESI, M+1]: 629.3.

Step B: N-chlorosuccinimide (43.30 mg, 324.23 μmol, 1.2 eq.) was added to a solution of compound 14-1 (170 mg, 270.19 μmol, 1 eq.) in dichloromethane (10 mL). The reaction system was purged with nitrogen three times, and subjected to reaction at 25° C. for 2 hours. The reaction was quenched with 5 mL of saturated aqueous sodium sulfite. The reaction mixture was added with 10 mL of dichloromethane. The organic phase was washed twice with 20 mL of saturated brine, dried over anhydrous sodium sulfate, filtered and concentrated to give a crude product of compound 14-2. MS [ESI, M+1]: 663.4.

Step C: 3 mL of trifluoroacetic acid was added to a solution of compound 14-2 (200 mg, 301.37 μmol, 1 eq.) in dichloromethane (3 mL). The reaction mixture was subjected to reaction at 25° C. for 1 hour in nitrogen atmosphere, and concentrated to give a crude product. The crude product was separated by prep-HPLC (water (0.1% trifluoroacetic acid, v/v)/acetonitrile system) to give compound 14. MS [ESI, M+1]: 563.2.

$^1$H NMR (400 MHz, DMSO-d$_6$) δ ppm 11.54 (s, 1H) 8.88 (br s, 2H) 8.75 (m, 1H) 7.81-8.53 (m, 1H) 7.77 (m, 2H) 7.40-7.65 (m, 4H) 7.22-7.35 (m, 1H) 7.12-7.21 (m, 1H) 6.78 (d, J=15.28 Hz, 1H) 6.65 (d, J=8.40 Hz, 1H) 6.54 (m, 1H) 4.35 (t, J=5.04 Hz, 2H) 3.58 (br s, 2H) 3.27 (br s, 2H) 3.02 (s, 3H) 2.87 (s, 3H) 2.39-2.48 (m, 2H) 0.90 (t, J=7.52 Hz, 3H).

-continued

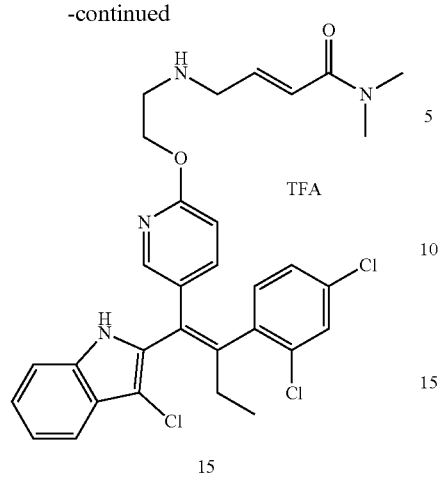

15

Example 16

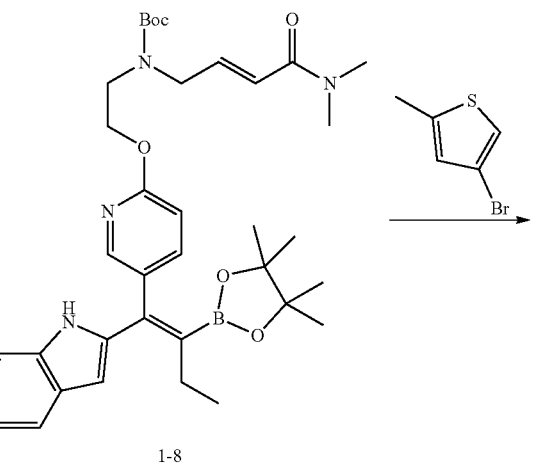

16-1

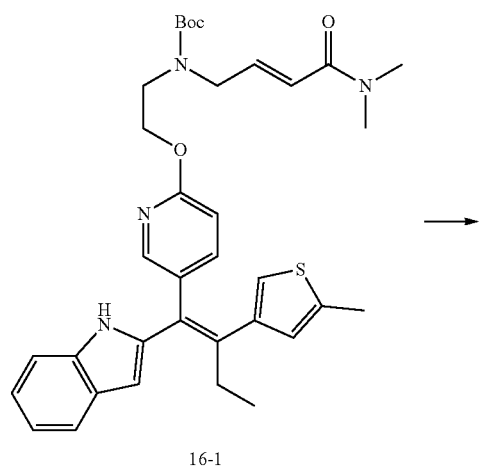

16-2

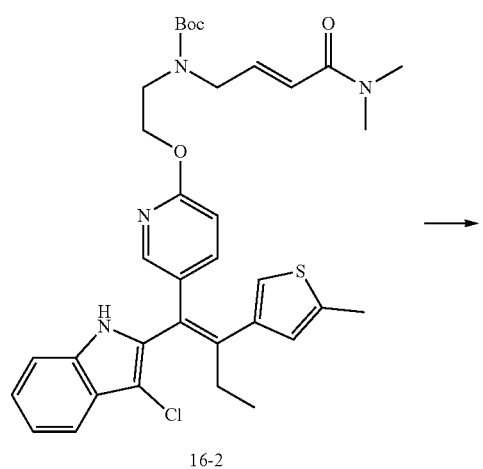

Step A: 1-Bromo-2,4-dichlorobenzene (239.70 mg, 1.06 mmol, 1.2 eq.), aqueous potassium hydroxide (4 M, 1.55 mL, 7 eq.) and Pd(PPh$_3$)$_2$Cl$_2$ (31.03 mg, 44.21 μmol, 0.05 eq.) were added to a solution of compound 1-8 (0.57 g, 884.26 μmol, 1 eq.) in 2-methyltetrahydrofuran (10 mL). The reaction system was purged with nitrogen three times, and subjected to reaction at 85° C. for 12 hours. After cooling to room temperature, the reaction system was diluted with 10 mL of water and 10 mL of ethyl acetate. The aqueous phase was extracted 3 times with 10 mL of ethyl acetate. The organic phases were combined, washed 3 times with 10 mL of saturated brine, dried over anhydrous sodium sulfate, filtered and concentrated to give a crude product. The crude product was separated by reversed-phase HPLC (0.1% trifluoroacetic acid condition) to give compound 15-1. MS [ESI, M+1]: 663.3.

Step B: A solution of compound 15-1 (125 mg, 188.36 μmol, 1 eq.) and N-chlorosuccinimide (30.18 mg, 226.03 μmol, 1.2 eq.) in dichloromethane (10 mL) was subjected to reaction at 20° C. for 1 hour. The reaction was quenched with 10 mL of water, and the aqueous phase was extracted 3 times with 20 mL of dichloromethane. The organic phases were combined, washed twice with 20 mL of saturated brine, dried over anhydrous sodium sulfate, filtered and concentrated to give a crude product of compound 15-2. MS [ESI, M+1]: 697.2.

Step C: Trifluoroacetic acid (24.50 mg, 214.88 μmol, 15.91 μL, 1 eq.) was added to a solution of compound 15-2 (150 mg, 214.88 μmol, 1 eq.) in dichloromethane (2 mL). The reaction mixture was subjected to reaction at 20° C. for 1 hour, and concentrated to give a crude product. The crude product was separated by prep-HPLC (water (0.025% formic acid, v/v)/acetonitrile system) to give compound 15. MS [ESI, M+3]: 599.3

$^1$H NMR (400 MHz, DMSO-d$_6$) δ ppm 11.52 (s, 1H) 8.85 (br s, 2H) 7.77 (dd, J=2.4, 0.8 Hz, 1H) 7.63 (d, J=2.0 Hz, 1H) 7.51 (d, J=8.0 Hz, 1H) 7.39-7.46 (m, 2H) 7.31-7.37 (m, 2H) 7.13-7.24 (m, 2H) 6.79 (d, J=15.2 Hz, 1H) 6.69 (dd, J=8.4, 0.61 Hz, 1H) 6.50-6.58 (m, 1H) 4.34-4.39 (m, 2H) 3.80 (br d, J=4.8 Hz, 2H) 3.28 (br s, 2H) 3.03 (s, 3H) 2.87 (s, 3H) 2.42-2.47 (m, 2H) 0.90 (t, J=7.6 Hz, 3H).

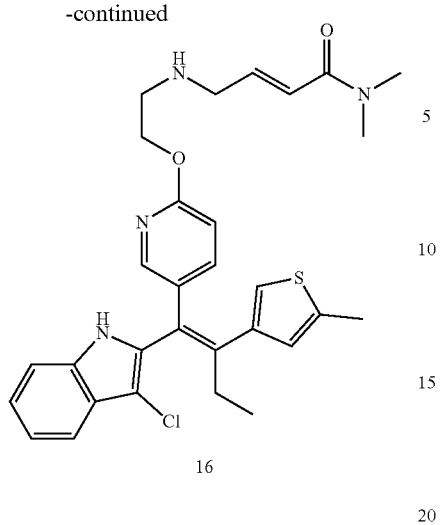

Example 17

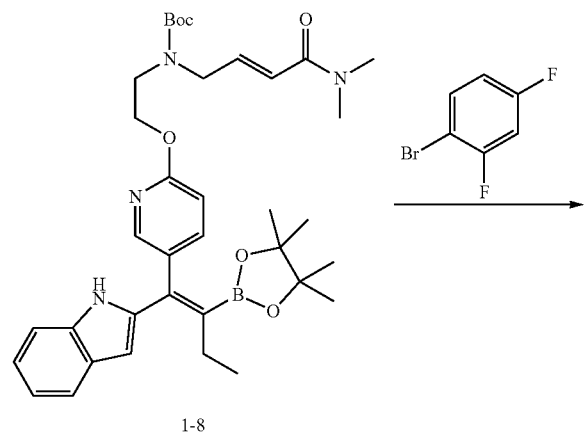

Step A: 4-Bromo-2-methylthiophene (187.88 mg, 1.06 mmol, 1.2 eq.), aqueous potassium hydroxide (4 M, 1.55 mL, 7 eq.) and Pd(PPh$_3$)$_2$Cl$_2$ (31.03 mg, 44.21 μmol, 0.05 eq.) were added to a solution of compound 1-8 (0.57 g, 884.26 μmol, 1 eq.) in 2-methyltetrahydrofuran (10 mL). The reaction system was purged with nitrogen three times, and subjected to reaction at 85° C. for 12 hours. After cooling to room temperature, the reaction system was diluted with 10 mL of water and 10 mL of ethyl acetate. The aqueous phase was extracted 3 times with 10 mL of ethyl acetate. The organic phases were combined, washed 3 times with 10 mL of saturated brine, dried over anhydrous sodium sulfate, filtered and concentrated to give a crude product. The crude product was separated by reversed-phase HPLC (water (0.1% trifluoroacetic acid, v/v)/acetonitrile system) to give compound 16-1. MS [ESI, M+1]: 615.4

Step B: A solution of compound 16-1 (65 mg, 105.73 μmol, 1 eq.) and N-chlorosuccinimide (16.94 mg, 126.87 μmol, 1.2 eq.) in dichloromethane (10 mL) was subjected to reaction at 20° C. for 12 hours. The reaction was quenched with 10 mL of water, and the aqueous phase was extracted 3 times with 20 mL of dichloromethane. The organic phases were combined, washed twice with 20 mL of saturated brine, dried over anhydrous sodium sulfate, filtered and concentrated to give a crude product of compound 16-2. MS [ESI, M+1]: 649.2

Step C: Trifluoroacetic acid (17.56 mg, 154.03 μmol, 11.40 μL, 1 eq.) was added to a solution of compound 16-2 (100 mg, 154.03 μmol, 1 eq.) in dichloromethane (2 mL). The reaction mixture was subjected to reaction at 20° C. for 1 hour, and concentrated to give a crude product. The crude product was separated by prep-HPLC (water (0.025% formic acid, v/v)/acetonitrile system) to give compound 16 (10.13 mg, 18.01 μmol). MS [ESI, M+1]: 549.4

$^1$H NMR (EW16419-130-P1A, 400 MHz, DMSO-d$_6$) δ ppm 11.42 (s, 1H) 7.72 (dd, J=2.4, 0.67 Hz, 1H) 7.48 (d, J=7.6 Hz, 1H) 7.34-7.39 (m, 1H) 7.23-7.28 (m, 1H) 7.09-7.20 (m, 2H) 7.04 (d, J=1.6 Hz, 1H) 6.57-6.67 (m, 2H) 6.50-6.56 (m, 2H) 4.22 (t, J=5.6 Hz, 2H) 3.32-3.36 (m, 5H) 2.99 (s, 2H) 2.84 (s, 3H) 2.35-2.43 (m, 5H) 0.93-0.99 (m, 3H)

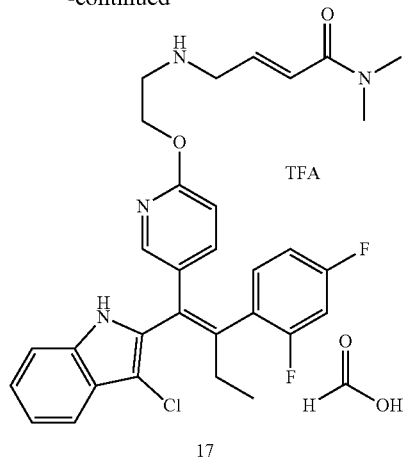

17

Step A: 1-Bromo-2,4-difluorobenzene (409.57 mg, 2.12 mmol, 1.2 eq.), aqueous potassium hydroxide (4 M, 3.09 mL, 7 eq.) and Pd(PPh₃)₂Cl₂ (62.07 mg, 88.43 μmol, 0.05 eq.) were added to a solution of compound 1-8 (1.14 g, 1.77 mmol, 1 eq.) in 2-methyltetrahydrofuran (10 mL) and water (2 mL). The reaction system was purged with nitrogen three times, and subjected to reaction at 85° C. for 12 hours. After cooling to room temperature, the reaction system was diluted with 10 mL of water and 10 mL of ethyl acetate. The aqueous phase was extracted 3 times with 10 mL of ethyl acetate. The organic phases were combined, washed with saturated brine, dried over anhydrous sodium sulfate, filtered and concentrated to give a crude product. The crude product was separated by reversed-phase HPLC (water (0.1% trifluoroacetic acid, v/v)/acetonitrile system) to give compound 17-1. MS [ESI, M+1]: 631.4

Step B: A solution of compound 17-1 (287 mg, 455.03 μmol, 1 eq.) and N-chlorosuccinimide (72.91 mg, 546.04 μmol, 1.2 eq.) in dichloromethane (5 mL) was subjected to reaction at 25° C. for 1 hour. The reaction was quenched with 10 mL of water, and the aqueous phase was extracted 3 times with 20 mL of dichloromethane. The organic phases were combined, washed twice with 20 mL of saturated brine, dried over anhydrous sodium sulfate, filtered and concentrated to give a crude product of compound 17-2. MS [ESI, M+1]: 665.2

Step C: Trifluoroacetic acid (1.54 g, 13.51 mmol, 1 mL, 29.95 eq.) was added to a solution of compound 17-2 (300 mg, 451.01 μmol, 1 eq.) in dichloromethane (5 mL). The reaction mixture was subjected to reaction at 25° C. for 0.5 hours, and concentrated to give a crude product. The crude product was separated by prep-HPLC (water (0.025% formic acid, v/v)/acetonitrile system) to give compound 17. MS [ESI, M+1]: 565.2

¹H NMR (EW16419-174-P1, 400 MHz, DMSO-d₆) δ ppm 11.50 (s, 1H) 8.19 (s, 1H) 7.68 (s, 1H) 7.50 (d, J=7.82 Hz, 1H) 7.28-7.41 (m, 2H) 7.04-7.24 (m, 5H) 6.45-6.65 (m, 3H) 4.16 (t, J=5.75 Hz, 2H) 3.32 (br d, J=4.40 Hz, 2H) 2.98 (s, 3H) 2.83 (s, 3H) 2.78 (t, J=5.75 Hz, 2H) 2.43 (q, J=7.30 Hz, 2H) 0.90 (t, J=7.46 Hz, 3H).

Example 18

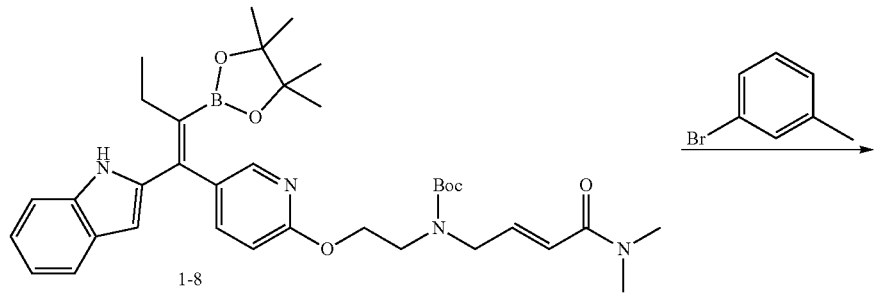

1-8

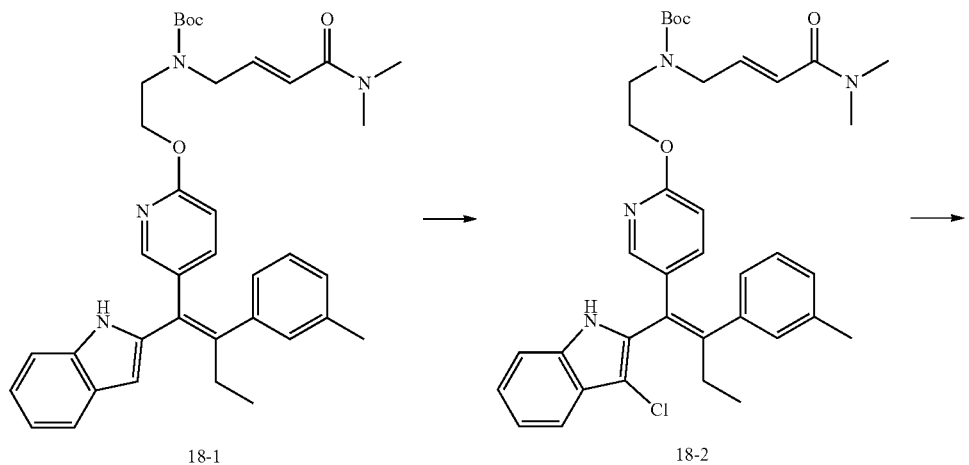

18-1    18-2

-continued

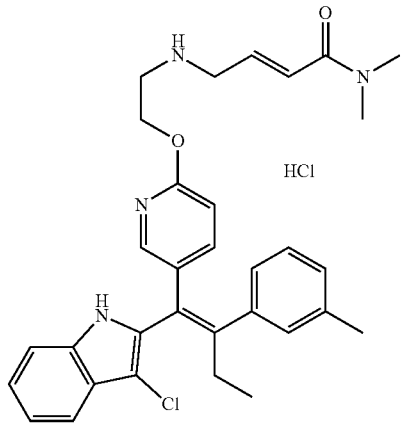

18

Step A: 1-Bromo-3-methylbenzene (504.13 mg, 2.95 mmol, 357.54 μL, 1 eq.), aqueous potassium hydroxide (4 M, 20.63 mmol, 5.16 mL, 7 eq.) and Pd(PPh$_3$)$_2$Cl$_2$ (103.44 mg, 147.38 μmol, 0.05 eq.) were added to a solution of compound 1-8 (1.9 g, 2.95 mmol, 1 eq.) in 2-methyltetrahydrofuran (5 mL). The reaction system was purged with nitrogen three times, and subjected to reaction at 85° C. for 12 hours. After cooling to room temperature, the reaction system was diluted with 20 mL of water and 20 mL of ethyl acetate. The aqueous phase was extracted 3 times with 10 mL of ethyl acetate. The organic phases were combined, washed with saturated brine, dried over anhydrous sodium sulfate, filtered and concentrated to give a crude product. The crude product was separated by reversed-phase HPLC (0.1% trifluoroacetic acid) to give compound 18-1. MS [ESI, M+1]: 609.3

Step B: N-chlorosuccinimide (71.33 mg, 534.19 μmol, 1.2 eq.) was added to a solution of compound 18-1 (271 mg, 445.16 μmol, 1 eq.) in dichloromethane (5 mL). The reaction mixture was subjected to reaction at 25° C. for 1 hour. The reaction was quenched with 10 mL of water, and the aqueous phase was extracted 3 times with 20 mL of dichloromethane. The organic phases were combined, washed twice with 20 mL of saturated brine, dried over anhydrous sodium sulfate, filtered and concentrated to give a crude product of compound 18-2. MS [ESI, M+1]: 643.4

Step C: Trifluoroacetic acid (770.00 mg, 6.75 mmol, 0.5 mL, 17.37 eq.) was added to a solution of compound 18-2 (250 mg, 388.67 μmol, 1 eq.) in dichloromethane (5 mL). The reaction mixture was subjected to reaction at 25° C. for 1 hour, and concentrated to give a crude product. The crude product was separated by prep-HPLC (water (0.025% formic acid, v/v)/acetonitrile system) to give compound 18. MS [ESI, M+1]: 543.3

$^1$H NMR (400 MHz, DMSO-d$_6$) δ=11.54 (s, 1H), 9.42 (br s, 2H), 7.67 (d, J=2.0 Hz, 1H), 7.49 (d, J=7.6 Hz, 1H), 7.40 (d, J=8.0 Hz, 1H), 7.28-7.01 (m, 6H), 6.95 (d, J=7.6 Hz, 1H), 6.83 (d, J=15.2 Hz, 1H), 6.69 -6.54 (m, 2H), 4.40 (t, J=5.2 Hz, 2H), 3.79-3.75 (m, 2H), 3.24 (br s, 2H), 3.03 (s, 3H), 2.87 (s, 3H), 2.44 (q, J=7.2 Hz, 2H), 2.27 (s, 3H), 0.90 (t, J=7.6 Hz, 3H).

Example 19

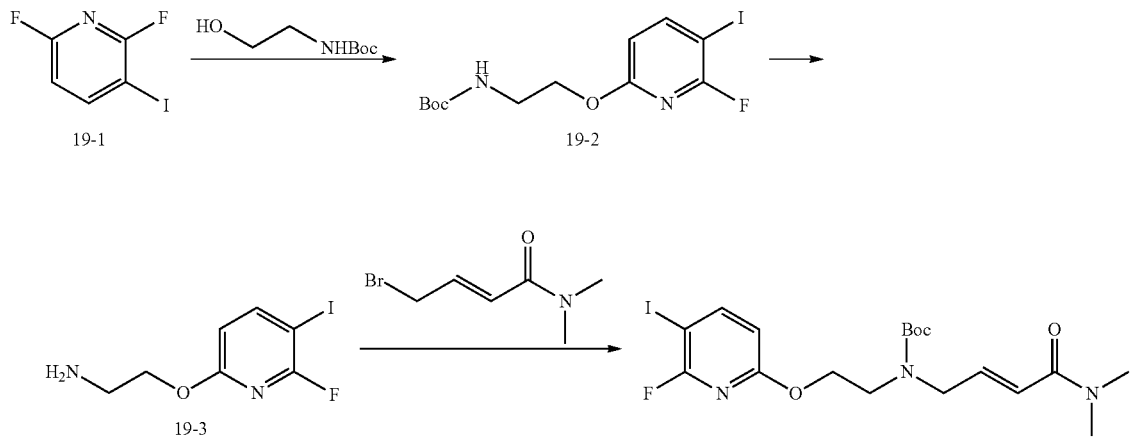

-continued

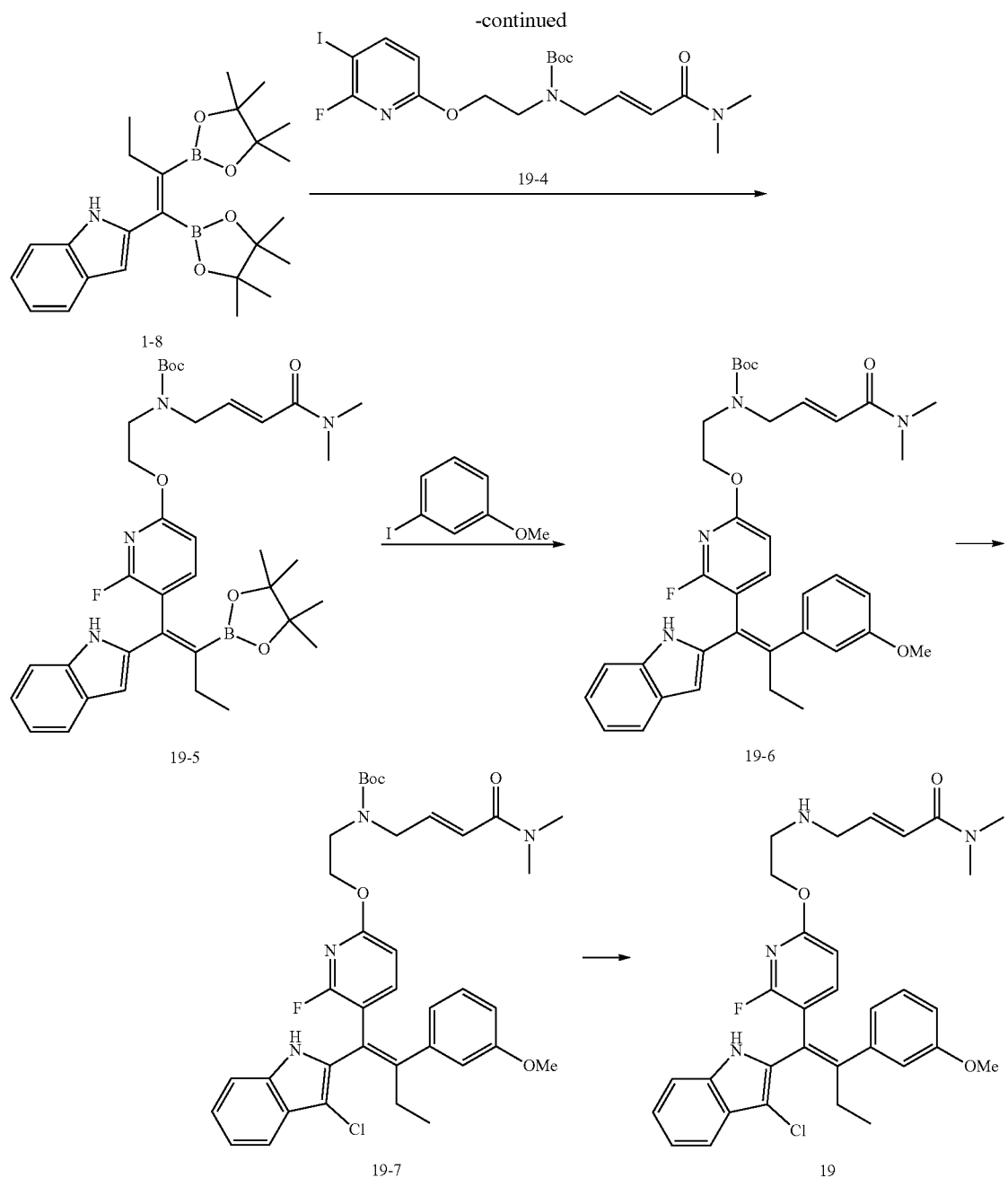

Step A: A solution of 2,6-difluoro-3-iodopyridine 19-1 (10 g, 41.50 mmol, 1 eq.) in N,N-dimethylformamide (80 mL) was cooled to 0° C. and added with sodium hydride (2.49 g, 62.25 mmol, 60% purity, 1.5 eq.) in batches while keeping the temperature below 0° C. After the addition, the reaction system was subjected to reaction at 0° C. for 0.5 hours. A solution of N-Boc-ethanolamine (6.69 g, 41.50 mmol, 6.43 mL, 1 eq.) in N,N-dimethylformamide (20 mL) was added dropwise to the reaction system while keeping the temperature below 0° C. After the dropwise addition, the reaction system was subjected to reaction at 0° C. for 1 hour. The reaction system was added with 50 mL of water for quenching, and extracted 3 times with 50 mL of ethyl acetate. The organic phases were combined, washed twice with 50 mL of saturated brine, dried over sodium sulfate, filtered and concentrated to give a crude product. The crude product was separated by silica gel column chromatography (petroleum ether:ethyl acetate=1:0-5:1, v/v) to give compound 19-2.

$^1$H NMR (400 MHz, CHLOROFORM-d) δ=7.85 (t, J=8.4 Hz, 1H), 6.45-6.31 (m, 1H), 4.30-4.13 (m, 2H), 3.44 (br d, J=4.8 Hz, 2H), 1.37 (s, 9H)

Step B: Methanolic hydrochloric acid (4 M, 2 mL, 1.50 eq.) was added to a solution of compound 19-2 (2.04 g, 5.34 mmol, 1 eq.) in ethanol (20 mL). The reaction system was subjected to reaction at 45° C. for 2 hours, and concentrated under reduced pressure to give compound 19-3. MS [ESI, M+1]: 283.4

Step C: A solution of N,N-dimethyl bromocrotonamide (615.03 mg, 3.20 mmol, 0.6 eq.) in N,N-dimethylformamide (1 mL) was added dropwise to a solution of compound 19-3

(1.7 g, 5.34 mmol, 1 eq., HCl) and N,N-diisopropylethylamine (2.07 g, 16.01 mmol, 2.79 mL, 3 eq.) in N,N-dimethylformamide (5 mL). The reaction system was subjected to reaction at 25° C. for 12 hours. A solution of (Boc)₂O (1.40 g, 6.40 mmol, 1.47 mL, 1.2 eq.) in dichloromethane (2 mL) was added dropwise to the reaction system while keeping the temperature below 0° C. The reaction system was subjected to reaction at 25° C. for 2 hours. The reaction system was diluted with 20 mL of water and 20 mL of ethyl acetate and separated. The aqueous phase was extracted three times with 10 mL of ethyl acetate. The organic phases were combined, washed twice with 20 mL of saturated brine, dried over anhydrous sodium sulfate, filtered and concentrated to give a crude product. The crude product was separated by silica gel column chromatography (petroleum ether:ethyl acetate=1:0-0:1, v/v) to give compound 19-4. MS [ESI, M+1]: 494.2

Step D: Compound 19-4 (440.66 mg, 893.28 μmol, 0.6 eq.), Pd(PPh₃)₂Cl₂ (52.25 mg, 74.44 μmol, 0.05 eq.) and cesium carbonate (970.16 mg, 2.98 mmol, 2 eq.) were added to a solution of compound 1-8 (0.63 g, 1.49 mmol, 1 eq.) in 2-methyltetrahydrofuran (5 mL). The reaction system was purged with nitrogen three times, added with 1 mL of water, and subjected to reaction at 30° C. for 12 hours to give compound 19-5 for direct use in the next reaction without purification. MS [ESI, M+1]: 663.4

Step E: 1-Bromo-3-methylbenzene (278.68 mg, 1.49 mmol, 188.30 μL, 1 eq.), aqueous potassium hydroxide (4 M, 2.61 mL, 7 eq.) and Pd(PPh₃)₂Cl₂ (52.25 mg, 74.50 μmol, 0.05 eq.) were added to a solution of compound 19-5 (986.47 mg, 1.49 mmol, 1 eq.) in 2-methyltetrahydrofuran (20 mL). The reaction system was purged with nitrogen three times, and subjected to reaction at 85° C. for 12 hours. After cooling to room temperature, the reaction system was diluted with 10 mL of water and 10 mL of ethyl acetate. The aqueous phase was extracted 3 times with 10 mL of ethyl acetate. The organic phases were combined, washed with saturated brine, dried over anhydrous sodium sulfate, filtered and concentrated to give a crude product. The crude product was separated by reversed-phase chromatography (0.1% trifluoroacetic acid) to give compound 19-6. MS [ESI, M+1]: 643.4

Step F: N-chlorosuccinimide (24.93 mg, 186.70 μmol, 1.2 eq.) was added to a solution of compound 19-6 (0.1 g, 155.58 μmol, 1 eq.) in dichloromethane (5 mL). The reaction system was subjected to reaction at 25° C. for 1 hour. The reaction was quenched with 10 mL of saturated aqueous sodium sulfite, and the aqueous phase was extracted 3 times with 20 mL of dichloromethane. The organic phases were combined, washed twice with 20 mL of saturated brine, dried over anhydrous sodium sulfate, filtered and concentrated to give a crude product. The crude product was separated by prep-HPLC (water (0.025% formic acid, v/v)/acetonitrile system) to give compound 19-7. MS [ESI, M+1]: 677.4

Step G: Trifluoroacetic acid (770.00 mg, 6.75 mmol, 0.5 mL, 228.66 eq.) was added to a solution of compound 19-7 (20 mg, 29.53 μmol, 1 eq.) in dichloromethane (3 mL). The reaction mixture was subjected to reaction at 25° C. for 1 hour, and concentrated to give a crude product. The crude product was separated by prep-HPLC (water (0.05% hydrochloric acid, v/v)/acetonitrile system) to give compound 19. MS [ESI, M+1]: 577.3

¹H NMR (400 MHz, METHANOL-d4) δ=7.44 (dd, J=8.4, 9.2 Hz, 1H), 7.37 (d, J=8.0 Hz, 1H), 7.26 (d, J=8.0 Hz, 1H), 7.10-6.98 (m, 3H), 6.76-6.62 (m, 4H), 6.58-6.46 (m, 2H), 4.39-4.32 (m, 2H), 3.77 (d, J=6.4 Hz, 2H), 3.61 (s, 3H), 3.33-3.27 (m, 2H), 3.00 (s, 3H), 2.88 (s, 3H), 2.46 (q, J=7.6 Hz, 2H), 0.89 (t, J=7.6 Hz, 3H).

Example 20

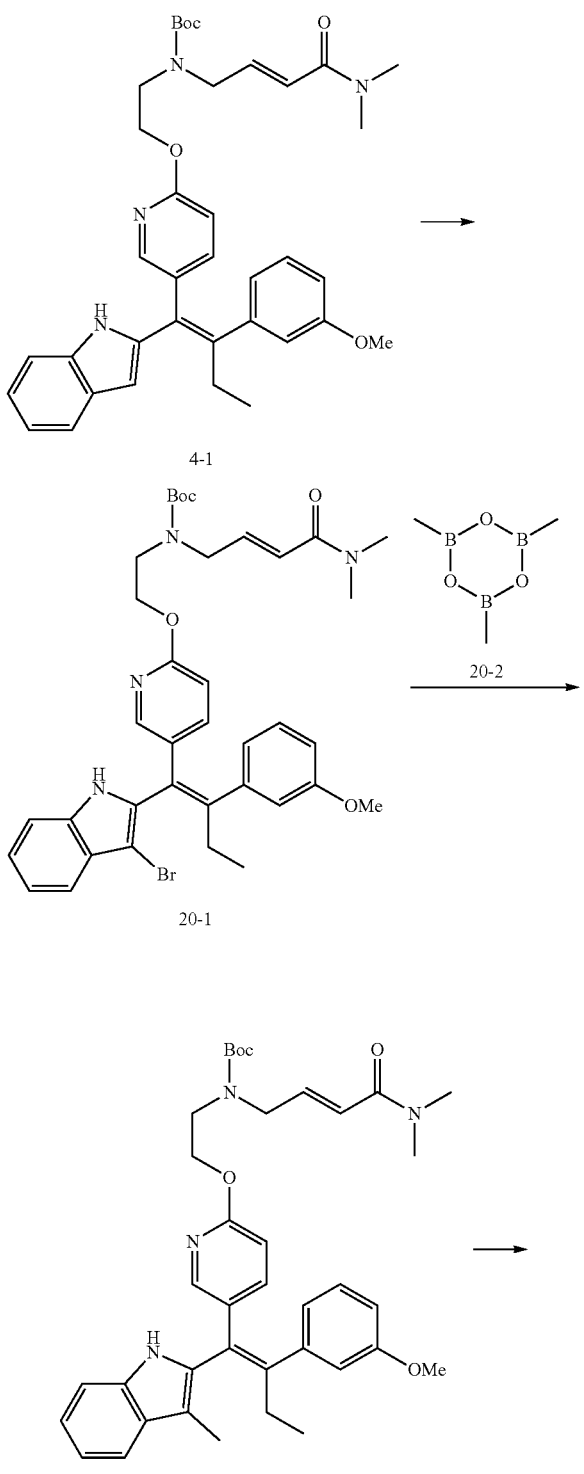

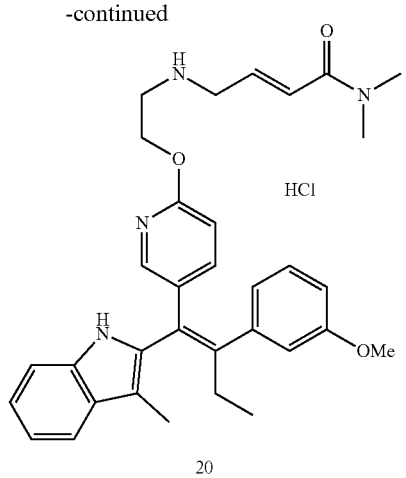

Step A: N-bromosuccinimide (329.55 mg, 1.85 mmol, 1.2 eq.) was added to a solution of compound 4-1 (964 mg, 1.54 mmol, 1 eq.) in dichloromethane (20 mL). The reaction system was purged with nitrogen three times, and subjected to reaction at 25° C. for 1 hour. The reaction was quenched with 10 mL of saturated aqueous sodium sulfite, and the aqueous phase was extracted 3 times with 20 mL of dichloromethane. The organic phases were combined, washed twice with 20 mL of saturated brine, dried over anhydrous sodium sulfate, and concentrated to give compound 20-1. MS [ESI, M+1]: 703.3

Step B: Compound 20-2 (1.07 g, 4.26 mmol, 1.19 mL, 3 eq.), cesium carbonate (1.39 g, 4.26 mmol, 3 eq.) and Pd(dppf)Cl$_2$·CH$_2$Cl$_2$ (116.06 mg, 142.11 μmol, 0.1 eq.) were added to a solution of compound 20-1 (1 g, 1.42 mmol, 1 eq.) in dioxane (10 mL). The reaction system was purged with nitrogen three times, and subjected to reaction at 110° C. for 3 hours. After cooling to room temperature, the reaction system was added with 10 mL of water and 10 mL of ethyl acetate for quenching and separated. The aqueous phase was extracted 3 times with 10 mL of ethyl acetate. The organic phases were combined, washed with 10 mL of saturated brine, dried over anhydrous sodium sulfate, filtered and concentrated to give a crude product. The crude product was separated by reversed-phase column chromatography (water (0.1% trifluoroacetic acid, v/v)/acetonitrile system) to give compound 20-3. MS [ESI, M+1]: 639.6

Step C: Trifluoroacetic acid (3.08 g, 27.01 mmol, 2.00 mL, 26.55 eq.) was added to a solution of compound 20-3 (650 mg, 1.02 mmol, 1 eq.) in dichloromethane (10 mL). The reaction mixture was subjected to reaction at 25° C. for 0.5 hours, and concentrated to give a crude product. The crude product was separated by prep-HPLC (water (0.05% hydrochloric acid, v/v)/acetonitrile system) to give compound 20. MS [ESI, M+1]: 539.3

$^1$H NMR (400 MHz, DMSO-d$_6$) δ=10.80 (s, 1H), 9.27-9.03 (m, 2H), 7.67 (d, J=2.0 Hz, 1H), 7.48 (d, J=7.6 Hz, 1H), 7.35-7.15 (m, 3H), 7.10-6.95 (m, 2H), 6.87-6.74 (m, 4H), 6.69-6.49 (m, 2H), 4.37 (br t, J=5.2 Hz, 2H), 3.78 (br d, J=6.0 Hz, 2H), 3.70 (s, 3H), 3.25 (br s, 2H), 3.03 (s, 3H), 2.87 (s, 3H), 2.45 (br d, J=7.6 Hz, 2H), 2.24-2.18 (m, 3H), 0.87 (t, J=7.4 Hz, 3H).

Example 21

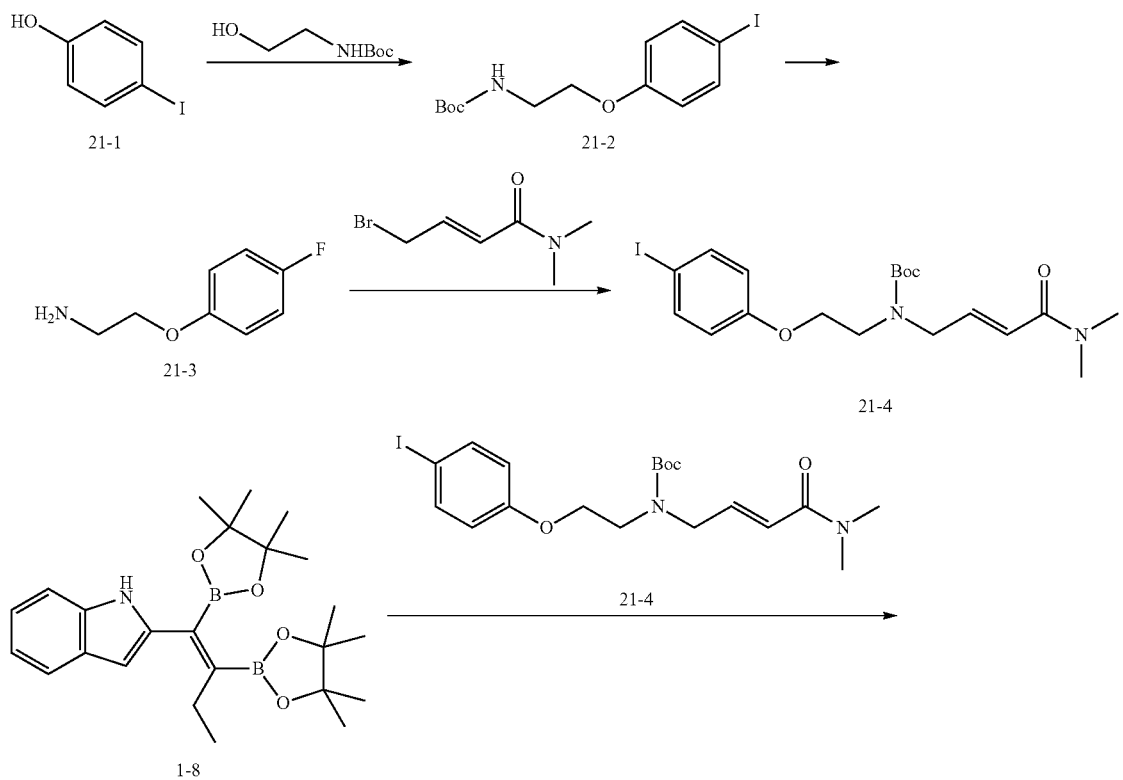

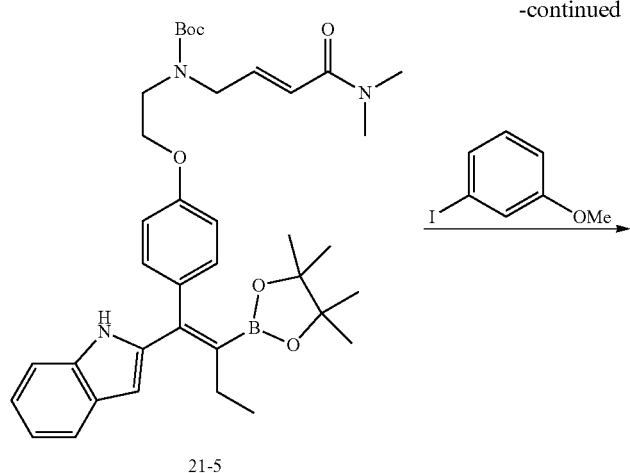

21-5

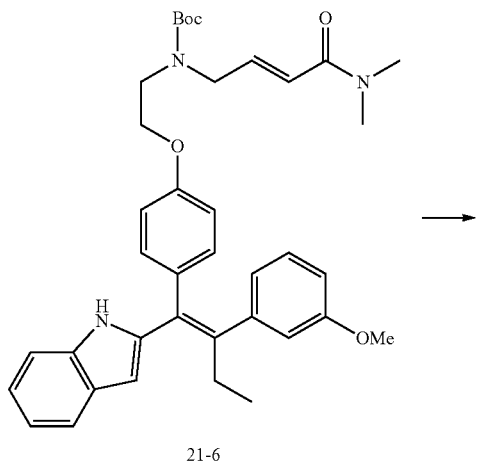

21-6

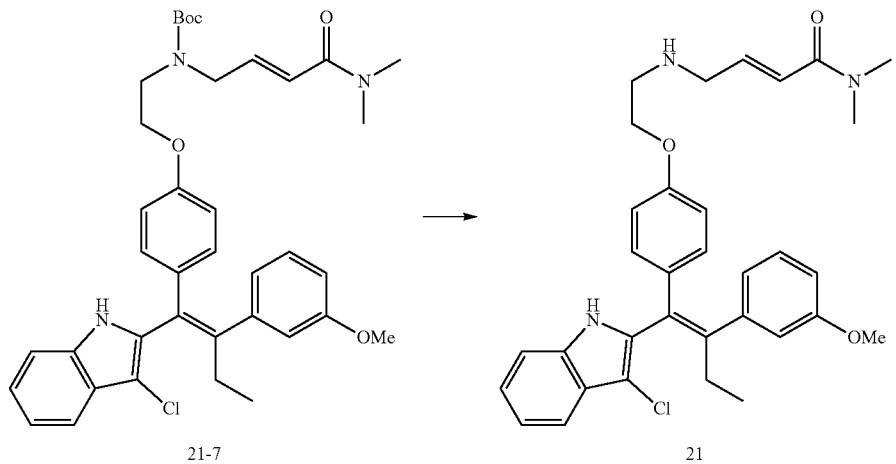

21-7

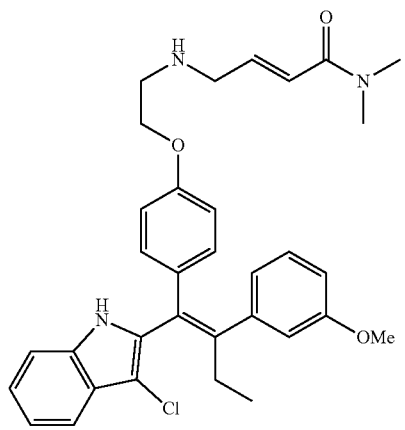

21

Step A: A solution of 4-iodophenol compound 21-1 (10 g, 45.45 mmol, 1 eq.), N-Boc-ethanolamine (8.79 g, 54.54 mmol, 8.45 mL, 1.2 eq.) and triphenylphosphine (17.88 g, 68.18 mmol, 1.5 eq.) in tetrahydrofuranthe (80 mL) was cooled to 0° C. and added dropwise with a solution of diethyl azodicarboxylate (11.87 g, 68.18 mmol, 12.39 mL, 1.5 eq.) in tetrahydrofuran (10 mL) while keeping the temperature below 0° C. After the addition, the reaction system was subjected to reaction at 25° C. for 12 hours. The reaction system was added with 50 mL of water and 50 mL of ethyl acetate for quenching, and extracted 3 times with 50 mL of ethyl acetate. The organic phases were combined, washed with 50 mL of saturated brine, dried over sodium sulfate, filtered and concentrated to give a crude product. The crude product was separated by silica gel column chromatography (petroleum ether:ethyl acetate=1:0-5:1, v/v) to give compound 21-2.

Step B: Methanolic hydrochloric acid (4 M, 20 mL, 2.08 eq.) was added to a solution of compound 21-2 (14 g, 38.55 mmol, 1 eq.) in methanol (100 mL). The reaction system was subjected to reaction at 45° C. for 1 hour, and concentrated under reduced pressure to give compound 21-3. MS [ESI, M+1]: 264.0

Step C: A solution of N,N-dimethyl bromocrotonamide (4.62 g, 24.04 mmol, 0.6 eq.) in N,N-dimethylformamide (10 mL) was added dropwise to a solution of compound 21-3 (12 g, 40.06 mmol, 1 eq., HCl) and N,N-diisopropylethylamine (15.53 g, 120.19 mmol, 20.93 mL, 3 eq.) in N,N-dimethylformamide (80 mL). The reaction system was subjected to reaction at 25° C. for 12 hours. The reaction system was added dropwise with a solution of (Boc)$_2$O (10.49 g, 48.07 mmol, 11.04 mL, 1.2 eq.) in N,N-dimethylformamide (10 mL) at 0° C., and subjected to reaction at 25° C. for 12 hours. After reaching room temperature, the reaction system was added with 100 mL of water for quenching and separated. The aqueous phase was extracted 3 times with 100 mL of ethyl acetate. The organic phases were combined, washed twice with 100 mL of saturated brine, dried over anhydrous sodium sulfate, filtered and concentrated to give a crude product. The crude product was separated by silica gel column chromatography (petroleum ether:ethyl acetate=1: 0-0:1, v/v) to give compound 21-4. MS [ESI, M+1]: 475.1

Step D: Compound 21-4 (2.52 g, 5.32 mmol, 0.6 eq.), Pd(PPh$_3$)$_2$Cl$_2$ (311.01 mg, 443.09 μmol, 0.05 eq.) and cesium carbonate (5.77 g, 17.72 mmol, 2 eq.) were added to a solution of compound 1-8 (3.75 g, 8.86 mmol, 1 eq.) in 2-methyltetrahydrofuran (10 mL). The reaction system was purged with nitrogen three times, added with 5 mL of water, and subjected to reaction at 30° C. for 12 hours to give compound 21-5 for direct use in the next reaction without purification.

Step E: 3-Iodoanisole (1.66 g, 8.86 mmol, 1.12 mL, 1 eq.), aqueous potassium hydroxide (4 M, 15.51 mL, 7 eq.) and Pd(dppf)Cl$_2$ (324.01 mg, 443.00 μmol, 0.05 eq.) were added to a solution of compound 21-5 (5.7 g, 8.86 mmol, 1 eq.) in 2-methyltetrahydrofuran (20 mL). The reaction system was purged with nitrogen three times, and subjected to reaction at 85° C. for 12 hours. After cooling to room temperature, the reaction system was diluted with 20 mL of water and 20 mL of ethyl acetate. The aqueous phase was extracted 3 times with 20 mL of ethyl acetate. The organic phases were combined, washed with 20 mL of saturated brine, dried over anhydrous sodium sulfate, filtered and concentrated to give a crude product. The crude product was separated by reversed-phase chromatography (0.1% trifluoroacetic acid) to give compound 21-6. MS [ESI, M+1]: 624.4

Step F: N-chlorosuccinimide (387.90 mg, 2.90 mmol, 1.2 eq.) was added to a solution of compound 21-6 (1.51 g, 2.42 mmol, 1 eq.) in dichloromethane (20 mL). The reaction system was subjected to reaction at 25° C. for 1 hour. The reaction was quenched with 10 mL of saturated aqueous sodium sulfite, and the aqueous phase was extracted 3 times with 20 mL of dichloromethane. The organic phases were combined, washed twice with 20 mL of saturated brine, dried over anhydrous sodium sulfate, filtered and concentrated to give compound 21-7. MS [ESI, M+1]: 658.3

Step G: Trifluoroacetic acid (7.70 g, 67.53 mmol, 5 mL, 29.63 eq.) was added to a solution of compound 21-7 (1.5 g, 2.28 mmol, 1 eq.) in dichloromethane (20 mL). The reaction mixture was subjected to reaction at 25° C. for 0.5 hours, and concentrated to give a crude product. The crude product was separated by prep-HPLC (water (0.05% aqueous ammonia, v/v)/acetonitrile system) to give compound 21. MS [ESI, M+1]: 558.1

$^1$H NMR (400 MHz, DMSO-d$_6$) δ=11.39 (s, 1H), 7.48 (d, J=7.6 Hz, 1H), 7.37 (d, J=8.0 Hz, 1H), 7.21-7.09 (m, 3H), 6.87-6.70 (m, 5H), 6.69-6.56 (m, 3H), 6.54-6.46 (m, 1H), 3.92-3.85 (m, 2H), 3.66 (s, 3H), 3.33-3.29 (m, 2H), 2.98 (s, 3H), 2.84 (s, 3H), 2.78 (br t, J=5.6 Hz, 2H), 2.45-2.37 (m, 2H), 0.92-0.85 (m, 3H).

Examples 22 and 23

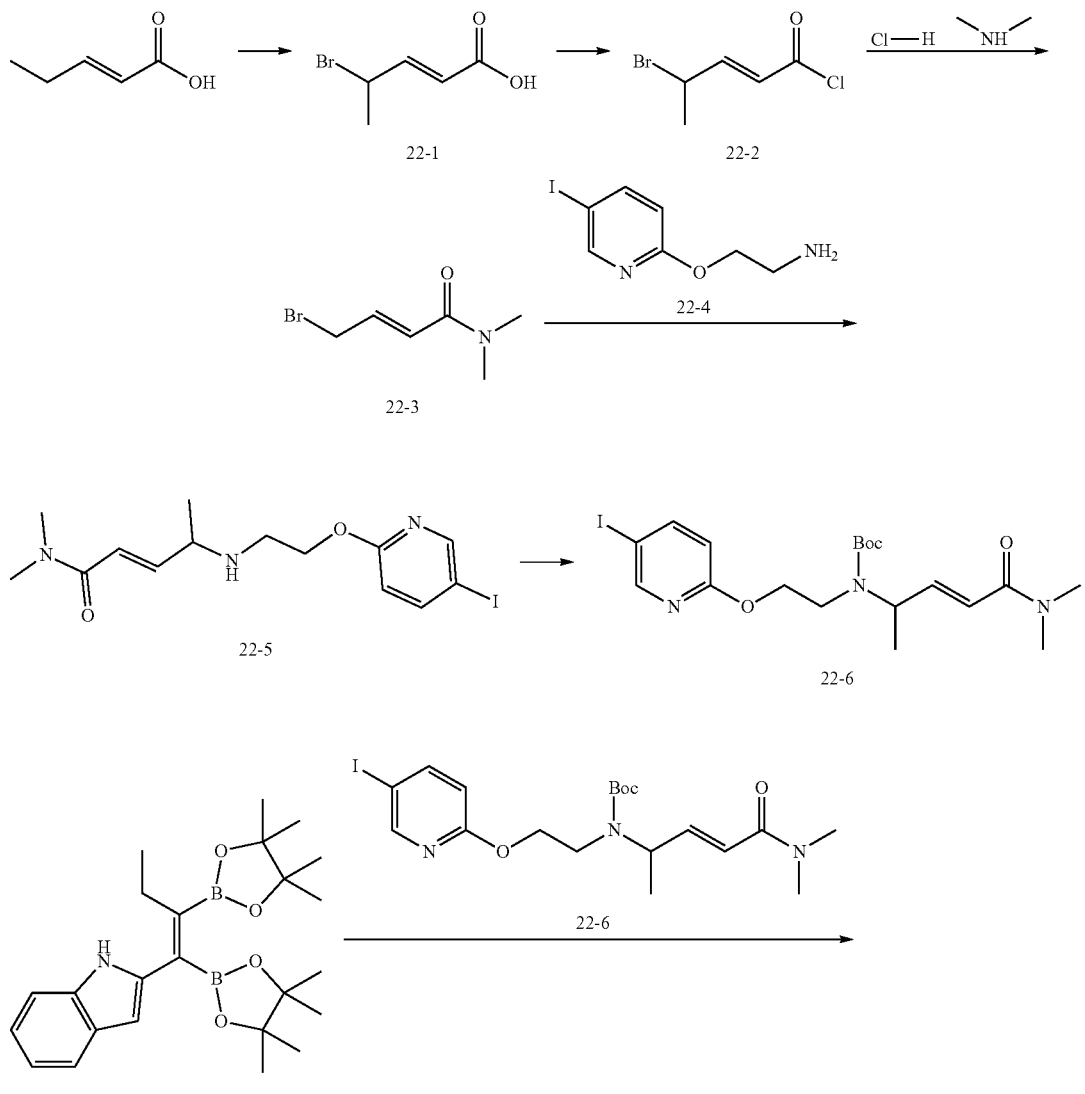

-continued

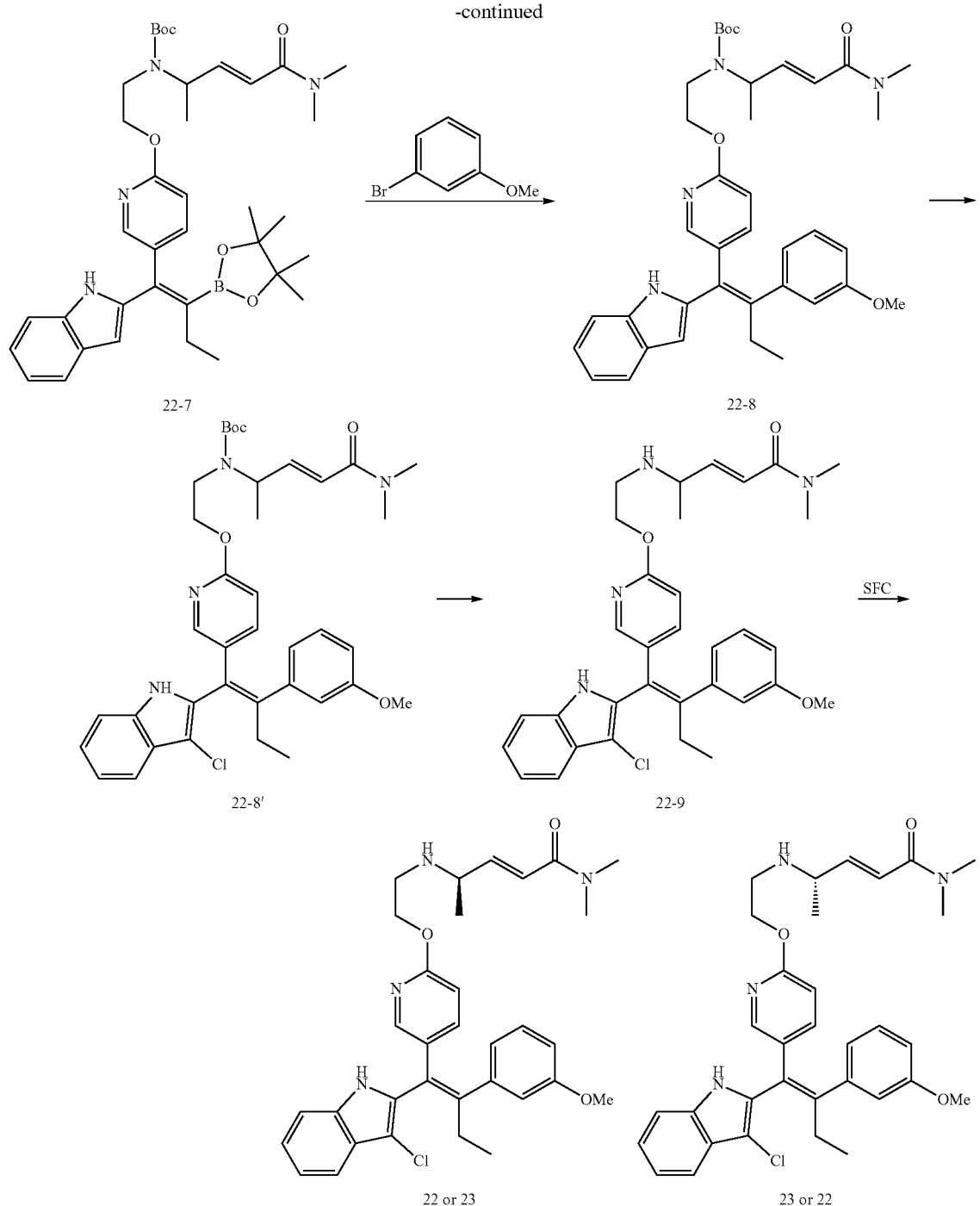

Step A: Trans-2-pentenoic acid (5 g, 49.94 mmol, 5.05 mL, 1 eq.) was dissolved in carbon tetrachloride (50 mL), and N-bromosuccinimide (11.56 g, 64.92 mmol, 1.3 eq.) was added. The reaction system was subjected to reaction at 80° C. for 12 hours in nitrogen atmosphere, filtered and concentrated under reduced pressure to give a crude product of compound 22-1. MS [ESI, M+1]: 179.1

Step B: 8 mL of thionyl chloride was added to compound 22-1 (3 g, 16.76 mmol, 1 eq.). The reaction system was subjected to reaction at 80° C. for 12 hours, and concentrated under reduced pressure to give compound 22-2.

Step C: Sodium carbonate (3.45 g, 32.51 mmol, 2 eq.) was added to a solution of dimethylamine (1.33 g, 16.26 mmol, 1.49 mL, 1 eq., hydrochloride) in dichloromethane (30 mL). The reaction system was added dropwise with a solution of compound 22-2 (3.21 g, 16.26 mmol, 1 eq.) in dichloromethane (12 mL) at 0° C., and subjected to reaction at 25° C. for 2 hours. The reaction system was diluted with 20 mL of water and 20 mL of dichloromethane, and was separated. The organic phase was washed twice with 30 mL of saturated brine, dried over anhydrous sodium sulfate, filtered and concentrated to give a crude product of compound 22-3. MS [ESI, M+1]: 206.1

Step D: Compound 22-4 (6.83 g, 25.88 mmol, 1 eq.) was dissolved in DMF (100 mL) and added with diisopropylethylamine (6.69 g, 51.76 mmol, 9.02 mL, 2 eq.). Compound 22-3 (3.2 g, 15.53 mmol, 0.6 eq.) was dissolved in DMF (50 mL), then added to the reaction system. The reaction mixture was subjected to reaction at 25° C. for 12 hours to give compound 22-5 for direct use in the next reaction without purification. MS [ESI, M+1]: 390.0

Step E: Compound 22-5 (10.07 g, 25.87 mmol, 1 eq.) was added with $(Boc)_2O$ (6.78 g, 31.05 mmol, 7.13 mL, 1.2 eq.). The reaction mixture was subjected to reaction at 25° C. for 2 hours in nitrogen atmosphere, added with 100 mL of water, and extracted three times with 200 mL of ethyl acetate. The organic phases were combined, washed twice with 200 mL of saturated brine, dried over anhydrous sodium sulfate, filtered and concentrated to give a crude product. The crude product was separated by column chromatography to give compound 22-6. MS [ESI, M+1]: 490.1

Step F: Compound 22-6 (399.06 mg, 815.49 µmol, 0.6 eq.), water (5 mL), cesium carbonate (885.68 mg, 2.72 mmol, 2 eq.) and bis(triphenylphosphine)palladium(II) dichloride (47.70 mg, 67.96 µmol, 0.05 eq.) were added to a solution of compound 1-8 (575.14 mg, 1.36 mmol, 1 eq.) in 2-methyltetrahydrofuran (20 mL). The reaction system was purged with nitrogen three times and subjected to reaction at 30° C. for 12 hours in nitrogen atmosphere to give compound 22-7.

Step G: m-Bromoanisole (305.05 mg, 1.63 mmol, 206.12 µL, 1.2 eq.), aqueous potassium hydroxide (4 M, 2.38 mL, 7 eq.) and bis(triphenylphosphine)palladium(II) dichloride (47.70 mg, 67.96 µmol, 0.05 eq.) were added to a solution of compound 22-7 (895.19 mg, 1.36 mmol, 1 eq.) in 2-methyltetrahydrofuran (20 mL). The reaction system was purged with nitrogen three times and subjected to reaction at 85° C. for 12 hours in nitrogen atmosphere. After cooling to room temperature, the reaction mixture was added with 20 mL of water. The aqueous phase was extracted three times with 30 mL of ethyl acetate, and the organic phases were combined and washed 3 times with 50 mL of saturated brine. The organic phase was dried over anhydrous sodium sulfate, filtered and concentrated to give a crude product. The crude product was separated by reversed-phase column chromatography (water (0.1% formic acid, v/v)/acetonitrile system) to give compound 22-8. MS [ESI, M+1]: 639.2

Step H: A solution of compound 22-8 (290 mg, 453.98 µmol, 1 eq.) and N-chlorosuccinimide (72.75 mg, 544.78 µmol, 1.2 eq.) in dichloromethane (5 mL) was subjected to reaction at 20° C. for 1 hour. The reaction was quenched with 10 mL of saturated aqueous sodium sulfite. The aqueous phase was separated and extracted three times with 20 mL of dichloromethane, and the organic phases were combined and washed twice with 20 mL of saturated brine. The organic phases were dried over anhydrous sodium sulfate, filtered and concentrated to give compound 22-8'. MS [ESI, M+1]: 673.3.

Step I: 1 mL of trifluoroacetic acid was added to a solution of compound 22-8' (203 mg, 301.53 µmol, 1 eq.) in dichloromethane (8 mL). The reaction mixture was subjected to reaction at 20° C. for 1 hour, and concentrated to give a crude product. The crude product was separated by prep-HPLC (water (0.05% hydrochloric acid, v/v)/acetonitrile system) to give compound 22-9. MS [ESI, M+1]: 573.2.

Step J: Compound 22-9 (150 mg, 256.78 µmol, 1 eq., HCl) was separated by SFC (chiral IG (water (0.1% ammonia, v/v)/methanol)) to give compound 22 or 23, Rt=2.290, MS [ESI, M+1]: 573.2; or to give compound 23 or 22, Rt=2.474, MS [ESI, M+1]: 573.2

$^1$H NMR (400 MHz, CHLOROFORM-d) δ=8.58 (s, 1H), 7.69-7.63 (m, 2H), 7.31-7.28 (m, 1H), 7.24-7.12 (m, 5H), 6.77-6.71 (m, 3H), 6.63-6.58 (m, 1H), 6.43 (d, J=8.4 Hz, 1H), 6.33 (d, J=15.2 Hz, 1H), 4.28-4.21 (m, 2H), 3.72 (s, 3H), 3.37 (t, J=6.8 Hz, 1H), 3.04 (s, 3H), 2.98 (s, 3H), 2.92-2.81 (m, 2H), 2.59-2.54 (m, 2H), 1.18 (d, J=6.4 Hz, 3H), 0.99 (t, J=8.0 Hz, 3H)

$^1$H NMR (400 MHz, CHLOROFORM-d) δ=9.42 (s, 1H), 7.67-7.57 (m, 2H), 7.32-7.28 (m, 1H), 7.24-7.11 (m, 5H), 6.76-6.71 (m, 3H), 6.57-6.36 (m, 3H), 4.35 (s, 2H), 3.89 (s, 1H), 3.71 (s, 3H), 3.23-3.06 (m, 2H), 2.94 (d, J=2. Hz, 6H), 2.59-2.53 (m, 2H), 1.34 (d, J=6.0 Hz, 3H), 0.98 (t, J=7.2 Hz, 3H)

Examples 24 and 25

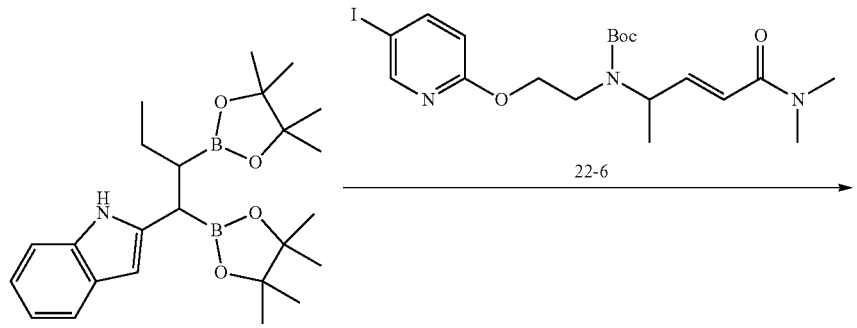

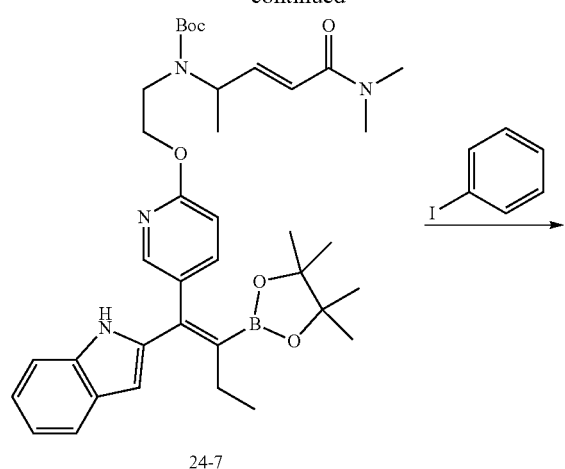
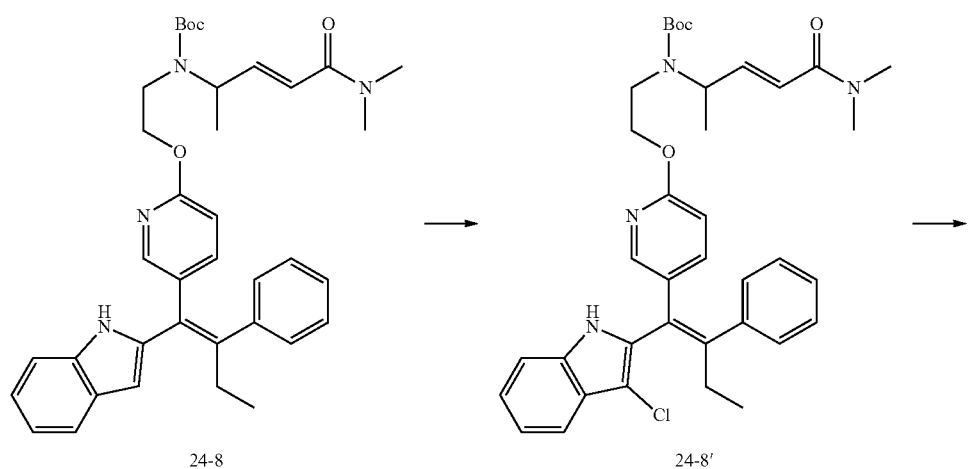
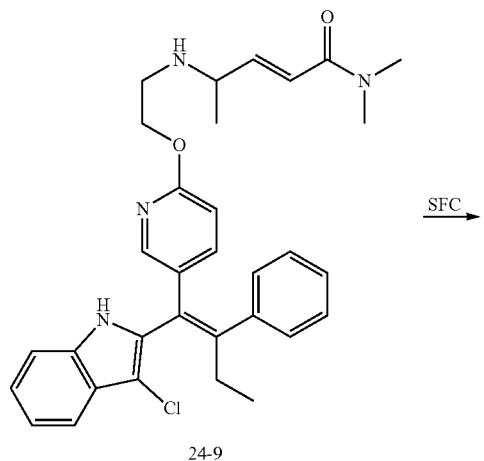

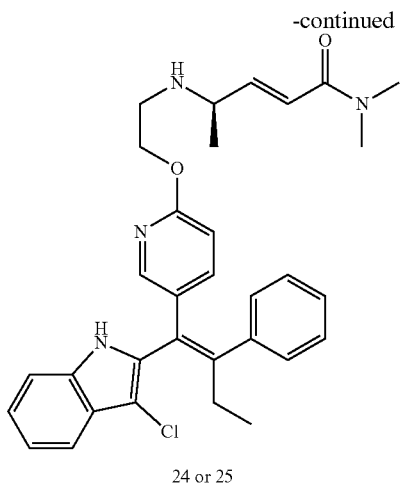

24 or 25

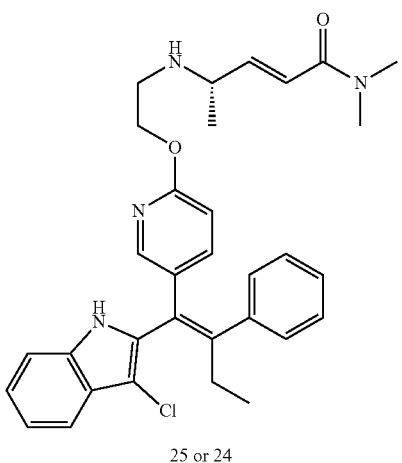

25 or 24

Step A: Compound 22-6 (3.48 g, 7.11 mmol, 0.9 eq.), Pd(PPh$_3$)$_2$Cl$_2$ (277.42 mg, 395.25 μmol, 0.05 eq.) and cesium carbonate (5.15 g, 15.81 mmol, 2 eq.) were added to a solution of compound 1-8 (4.75 g, 11.23 mmol, 1.42 eq.) in 2-methyltetrahydrofuran (30 mL). The reaction system was purged with nitrogen three times, added with 6 mL of water, and subjected to reaction at 30° C. for 12 hours to give compound 24-7 for direct use in the next reaction without purification.

Step B: Iodobenzene (1.94 g, 9.49 mmol, 1.06 mL, 1.2 eq.), aqueous potassium hydroxide (4 M, 13.84 mL, 7 eq.) and Pd(PPh$_3$)$_2$Cl$_2$ (277.61 mg, 395.52 μmol, 0.05 eq.) were added to a solution of compound 24-7 (5.21 g, 7.91 mmol, 1 eq.) in 2-methyltetrahydrofuran (20 mL). The reaction system was purged with nitrogen three times, and subjected to reaction at 85° C. for 12 hours. After cooling to room temperature, the reaction system was added with 30 mL of water and extracted 3 times with 50 mL of ethyl acetate. The organic phases were combined, washed twice with 50 mL of saturated brine, dried over anhydrous sodium sulfate, filtered and concentrated to give a crude product. The crude product was separated by reversed-phase chromatography (0.1% formic acid) to give compound 24-8. MS [ESI, M+1]: 609.3

Step C: N-chlorosuccinimide (552.76 mg, 4.14 mmol, 1.2 eq.) was added to a solution of compound 24-8 (2.1 g, 3.45 mmol, 1 eq.) in dichloromethane (25 mL). The reaction system was subjected to reaction at 25° C. for 12 hours. The reaction was quenched with 15 mL of saturated aqueous sodium sulfite. The reaction mixture was added with 30 mL of dichloromethane. The organic phase was washed twice with 20 mL of saturated brine, dried over anhydrous sodium sulfate, filtered and concentrated to give compound 24-8'. MS [ESI, M+1]: 643.3

Step D: 10 mL of trifluoroacetic acid was added to a solution of compound 24-8' (1.9 g, 2.95 mmol, 1 eq.) in dichloromethane (10 mL). The reaction mixture was subjected to reaction at 25° C. for 1 hour, and concentrated to give a crude product. The crude product was separated by prep-HPLC (water (0.05% hydrochloric acid, v/v)/acetonitrile system) to give compound 24-9. MS [ESI, M+1]: 543.3

Step E: Compound 24-9 (150 mg, 256.78 μmol, 1 eq., HCl) was separated by SFC (chiral IG (water (0.1% ammonia, v/v)/ethanol)) to give compound 24 or 25, Rt=2.148, MS [ESI, M+1]: 543.3; or to give compound 25 or 24, Rt=2.352, MS [ESI, M+1]: 543.3

$^1$H NMR (400 MHz, DMSO-d$_6$) δ=11.46 (s, 1H), 7.61 (d, J=2.4 Hz, 1H), 7.49 (d, J=7.6 Hz, 1H), 7.38 (d, J=8.0 Hz, 1H), 7.29 (d, J=7.6 Hz, 2H), 7.23 (d, J=7.2 Hz, 1H), 7.21-7.16 (m, 3H), 7.15-7.09 (m, 2H), 6.55 (d, J=8.8 Hz, 1H), 6.43-6.39 (m, 2H), 4.15-4.08 (m, 2H), 3.30-3.25 (m, 1H), 2.96 (s, 3H), 2.82 (s, 3H), 2.74-2.62 (m, 2H), 2.45 (br d, J=7.6 Hz, 2H), 1.06 (d, J=6.8 Hz, 3H), 0.89 (t, J=7.6 Hz, 3H).

$^1$H NMR (400 MHz, DMSO-d$_6$) δ=11.61 (s, 1H), 9.51-9.18 (m, 2H), 7.64 (d, J=2.8 Hz, 1H), 7.39 (br d, J=8.0 Hz, 4H), 7.29 (br s, 2H), 7.18-7.18 (m, 2H), 6.78 (d, J=15.2 Hz, 1H), 6.61 (d, J=8.8 Hz, 1H), 6.55-6.47 (m, 1H), 4.34 (br s, 2H), 4.06-3.98 (m, 1H), 3.16 (br s, 2H), 2.99 (s, 3H), 2.84 (s, 3H), 2.44 (br d, J=7.6 Hz, 2H), 1.35 (d, J=6.8 Hz, 3H), 0.88 (t, J=7.6 Hz, 3H).

Example 26

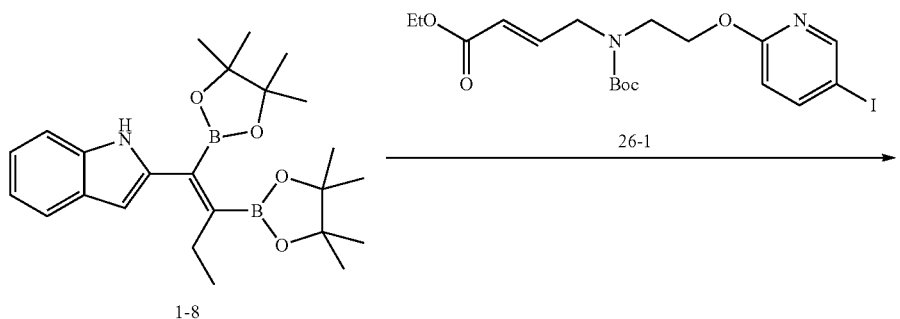

-continued

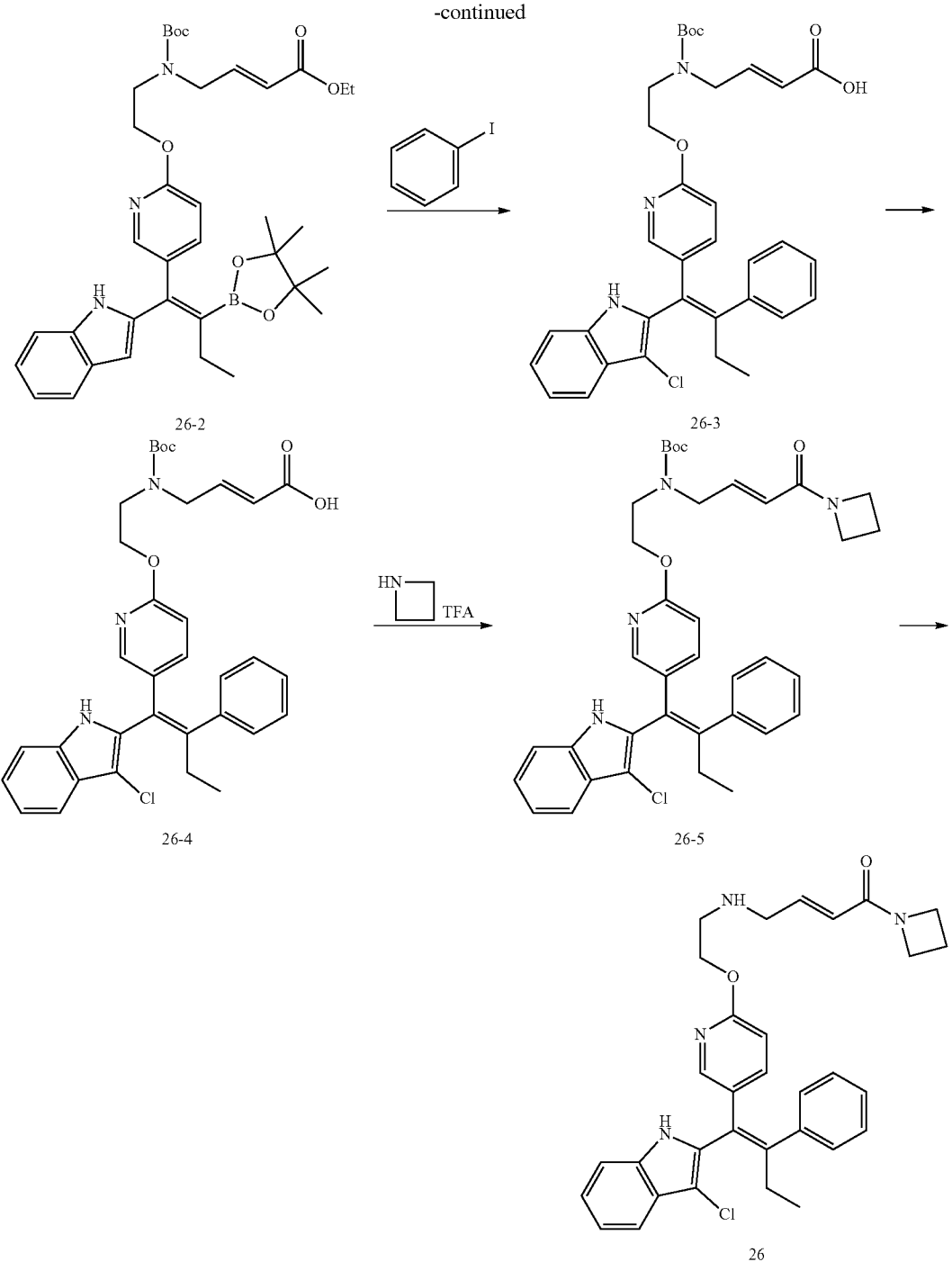

Step A: Bis(triphenylphosphine)palladium(II) dichloride (116.81 mg, 166.42 μmol, 0.05 eq.) and cesium carbonate (2.17 g, 6.66 mmol, 2 eq.) were sequentially added to a solution of compounds 1-8 (2 g, 4.73 mmol, 1.42 eq.) (in 2-methyltetrahydrofuran, theoretical value) and 26-1 (1.59 g, 3.33 mmol, 1 eq.) in 2-methyl tetrahydrofuran (15 mL). The reaction system was purged with nitrogen three times, added with 1 mL of water, subjected to reaction at 30° C. for 10 hours in nitrogen atmosphere and then cooled to room temperature to give compound 26-2 for direct use in the next reaction without purification. MS [ESI, M+1]: 646.4

Step B: Aqueous potassium hydroxide (4 M, 5.83 mL, 7 eq.) and bis(triphenylphosphine)palladium(II) dichloride (116.88 mg, 166.51 μmol, 0.05 eq.) were added to a solution of compound 26-2 (2.15 g, 3.33 mmol, 1 eq.) and iodobenzene (815.28 mg, 4.00 mmol, 445.51 μL, 1.2 eq.) in 2-methyltetrahydrofuran (10 mL). The reaction system was purged with nitrogen three times, and subjected to reaction at 85° C. for 12 hours in nitrogen atmosphere. After cooling to room temperature, the reaction mixture was added with 25 mL of water, and extracted three times with 30 mL of ethyl acetate. The organic phases were combined and washed twice with 30 mL of saturated brine. The organic phase was dried over anhydrous sodium sulfate, filtered and concentrated to give a crude product. The crude product was separated by reversed-phase column chromatography (trifluoroacetic acid system) to give compound 26-3. MS [ESI, M+1]: 568.2

Step C: N-chlorosuccinimide (342.67 mg, 2.57 mmol, 1.2 eq.) was added to a solution of compound 26-3 (1.21 g, 2.14 mmol, 1 eq.) in dichloromethane (15 mL). The reaction system was purged with nitrogen three times, and subjected to reaction at 25° C. for 2 hours. The reaction mixture was diluted with 10 mL of dichloromethane, and the organic phase was washed twice with 10 mL of saturated brine. The organic phase was dried over anhydrous sodium sulfate, filtered and concentrated to give a crude product. The crude product was separated by prep-HPLC (water (10 mM ammonium bicarbonate)-acetonitrile) to give compound 26-4. MS [ESI, M+1]: 602.2

Step D: N,N-diisopropylethylamine (85.86 mg, 664.32 µmol, 115.71 µL, 2 eq.) and 2-(7-azabenzotriazol-1-yl)-N,N,N,N-tetramethyluronium hexafluorophosphate (151.56 mg, 398.59 µmol, 1.2 eq.) were added to a solution of compound 26-4 (200 mg, 332.16 µmol, 1 eq.) and azetidine trifluoroacetate (31.08 mg, 332.16 µmol, 36.73 µL, 1 eq., hydrochloride) in N,N-dimethylformamide (10 mL). The reaction system was purged with nitrogen 3 times, and subjected to reaction at 25° C. for 2 hours. After cooling to room temperature, the reaction mixture was added with 10 mL of water, and extracted three times with 10 mL of ethyl acetate. The organic phases were combined and washed twice with 10 mL of saturated brine. The organic phase was dried over anhydrous sodium sulfate, filtered and concentrated to give a crude product of compound 26-5. MS [ESI, M+1]: 641.3

Step E: Trifluoroacetic acid (9.54 g, 83.66 mmol, 6.19 mL, 227.31 eq.) was added to a solution of compound 26-5 (236 mg, 368.06 µmol, 1 eq.) in dichloromethane (5 mL). The reaction mixture was subjected to reaction at 25° C. for 1 hour in nitrogen atmosphere, and concentrated to give a crude product. The crude product was separated twice by prep-HPLC (water (0.05% aqueous ammonia, v/v)-acetonitrile; water (10 mM ammonium bicarbonate)-acetonitrile) to give compound 26. MS [ESI, M+1]: 541.3

$^1$H NMR (400 MHz, METHANOL-$d_4$) δ=7.71 (d, J=1.9 Hz, 1H), 7.54 (d, J=7.8 Hz, 1H), 7.39-7.10 (m, 9H), 6.72 (td, J=6.4, 15.4 Hz, 1H), 6.64-6.59 (m, 1H), 6.35-6.26 (m, 1H), 4.42-4.38 (m, 2H), 4.30 (t, J=7.7 Hz, 2H), 4.07 (t, J=7.8 Hz, 2H), 3.72 (dd, J=1.3, 6.4 Hz, 2H), 3.25-3.22 (m, 2H), 2.56 (q, J=7.4 Hz, 2H), 2.33 (td, J=7.8, 15.6 Hz, 2H), 0.98 (t, J=7.5 Hz, 3H).

Example 27

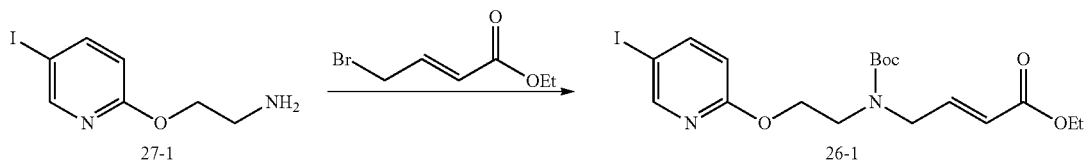

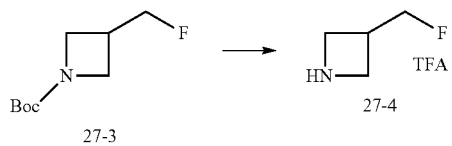

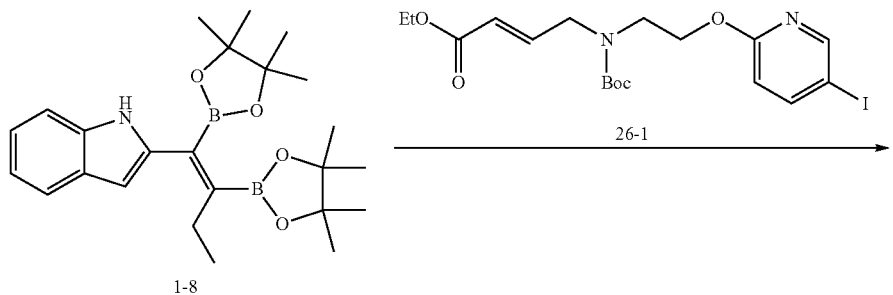

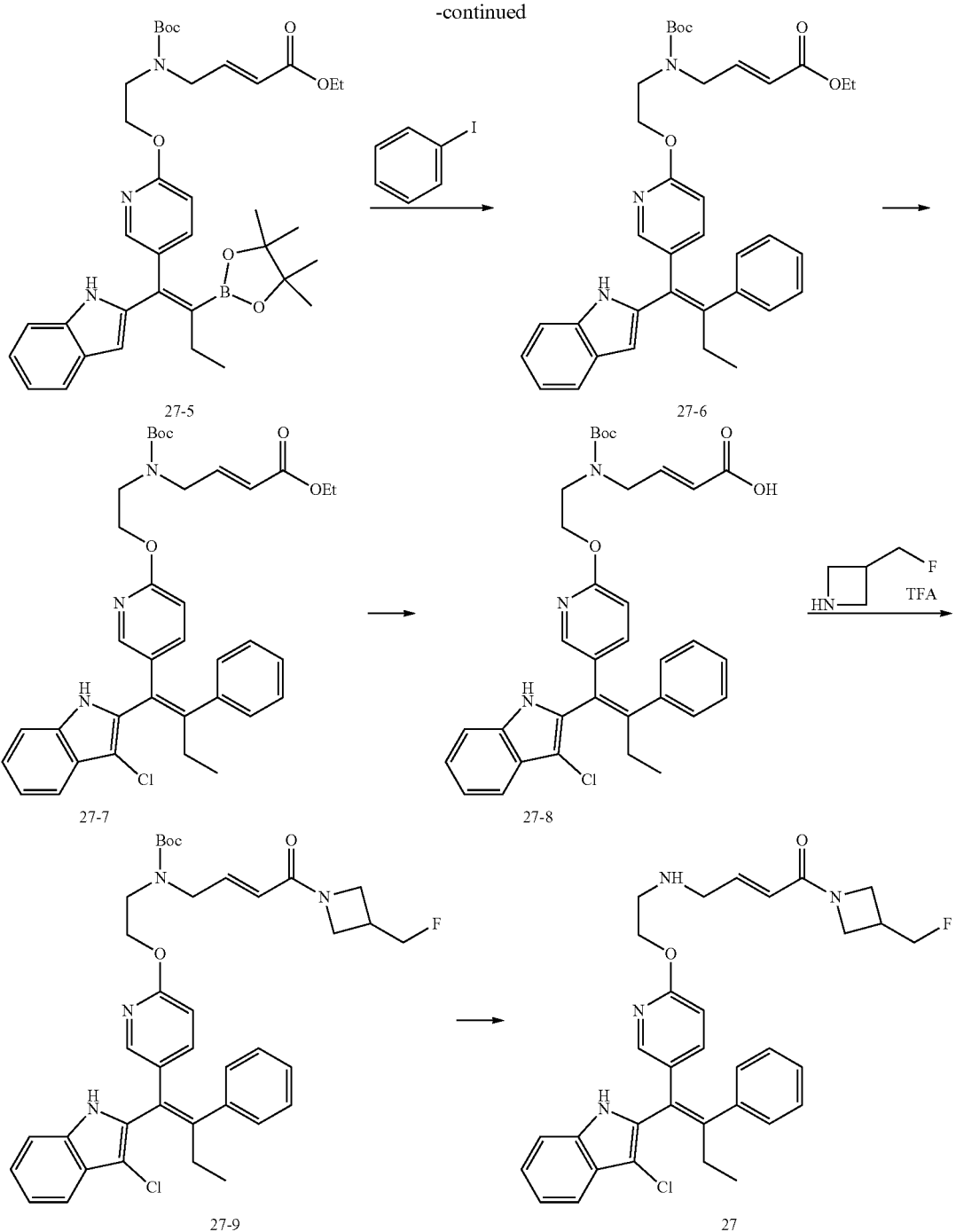

Step A: N,N-diisopropylethylamine (6.70 g, 51.80 mmol, 9.02 mL, 2 eq.) was added to a solution of compound 27-1 (6.84 g, 25.90 mmol, 1 eq.) in N,N-dimethylformamide (50 mL). A solution of ethyl bromocrotonate (3 g, 15.54 mmol, 2.14 mL, 0.6 eq.) in N,N-dimethylformamide (15 mL) was added dropwise and slowly to the reaction system. The reaction system was subjected to reaction at 25° C. for 22 hours and then cooled to 0° C. before (Boc)₂O (5.65 g, 25.90 mmol, 5.95 mL, 1 eq.) was added. The reaction system was subjected to reaction at 25° C. for 2 hours, added with 20 mL of water, and extracted three times with 25 mL of ethyl acetate. The organic phases were combined, washed twice with 50 mL of saturated brine, dried over anhydrous sodium sulfate, filtered and concentrated to give a crude product. The crude product was separated by reversed-phase column chromatography (water (0.1% trifluoroacetic acid, v/v)-acetonitrile) to give compound 26-1. MS [ESI, M+1]: 477.1

Step B: Trifluoroacetic acid (8.01 g, 70.23 mmol, 5.20 mL, 66.45 eq.) was added to a solution of compound 27-3 (200 mg, 1.06 mmol, 1 eq.) in dichloromethane (5.2 mL). The reaction mixture was subjected to reaction at 25° C. for 1 hour, and concentrated to give a crude product of compound 27-4.

¹H NMR (EW19918-27-P1, 400 MHz, DMSO-d₆) δ=11.32-10.91 (m, 1H), 9.24-8.78 (m, 1H), 4.61 (d, J=4.9 Hz, 1H), 4.49 (d, J=4.9 Hz, 1H), 4.09-3.99 (m, 1H), 3.87-3.78 (m, 1H), 3.23-3.05 (m, 1H).

Step C: Bis(triphenylphosphine)palladium(II) dichloride (73.01 mg, 104.01 µmol, 0.05 eq.) and cesium carbonate (1.36 g, 4.16 mmol, 2 eq.) were added to a solution of compounds 1-8 (1.25 g, 2.95 mmol, 1.42 eq.) (in 2-methyltetrahydrofuran, theoretical value) and 26-1 (990.84 mg, 2.08 mmol, 1 eq.) in 2-methyl tetrahydrofuran (15 mL). The reaction system was purged with nitrogen three times, and added with 1 mL of water. The reaction mixture was subjected to reaction at 30° C. for 8 hours in nitrogen atmosphere and then cooled to room temperature to give compound 27-5 for direct use in the next reaction without purification. MS [ESI, M+1]:646.4

Step D: Aqueous potassium hydroxide (4 M, 3.63 mL, 7 eq.) and bis(triphenylphosphine)palladium(II) dichloride (72.84 mg, 103.78 µmol, 0.05 eq.) were added to a solution of compound 27-5 (1.34 g, 2.08 mmol, 1 eq.) and iodobenzene (508.13 mg, 2.49 mmol, 277.67 µL, 1.2 eq.) in 2-methyltetrahydrofuran (8 mL). The reaction system was purged with nitrogen three times, and subjected to reaction at 85° C. for 12 hours in nitrogen atmosphere. After cooling to room temperature, the reaction mixture was added with 25 mL of water, and extracted three times with 30 mL of ethyl acetate. The organic phases were combined and washed twice with 30 mL of saturated brine. The organic phase was dried over anhydrous sodium sulfate, filtered and concentrated to give a crude product. TLC chromatography (PE:EA=5:1) showed that the desired compound was obtained. The crude product was separated by column chromatography to give compound 27-6. MS [ESI, M+1]: 596.3

Step E: N-chlorosuccinimide (154.39 mg, 1.16 mmol, 1.2 eq.) was added to a solution of compound 27-6 (574 mg, 963.53 µmol, 1 eq.) in dichloromethane (15 mL). The reaction system was purged with nitrogen three times, and subjected to reaction at 25° C. for 2 hours. The reaction mixture was extracted and diluted with 10 mL of dichloromethane, and the organic phases were combined and washed twice with 20 mL of saturated brine. The organic phase was dried over anhydrous sodium sulfate, filtered and concentrated to give a crude product of compound 27-7. MS [ESI, M+1]: 630.2

Step F: Water (10.00 g, 555.08 mmol, 10 mL, 874.49 eq.) was added to a solution of compound 27-7 (400 mg, 634.75 µmol, 1 eq.) and lithium hydroxide monohydrate (266.36 mg, 6.35 mmol, 10 eq.) in methanol (30 mL). The reaction mixture was subjected to reaction at 25° C. for 6 hours. The reaction mixture was adjusted to pH 7 with hydrochloric acid (3 M), then 5 mL of water was added. The aqueous phase was extracted three times with 10 mL of ethyl acetate, and the organic phases were combined and washed twice with 10 mL of saturated brine, dried over anhydrous sodium sulfate, filtered and concentrated to give a crude product of compound 27-8. MS [ESI, M+1]: 602.2

Step G: N,N-diisopropylethylamine (30.05 mg, 232.51 µmol, 40.50 µL, 2 eq.) and 2-(7-azabenzotriazol-1-yl)-N,N,N,N-tetramethyluronium hexafluorophosphate (53.04 mg, 139.51 µmol, 1.2 eq.) were added to a solution of compounds 27-8 (70 mg, 116.26 µmol, 1 eq.) and 27-4 (23.62 mg, 116.26 µmol, 1 eq., trifluoroacetate) in N,N-dimethylformamide (3 mL). The reaction system was purged with nitrogen 3 times, and subjected to reaction at 25° C. for 4 hours in nitrogen atmosphere. After cooling to room temperature, the reaction mixture was added with 10 mL of water, and extracted three times with 10 mL of ethyl acetate. The organic phases were combined and washed twice with 10 mL of saturated brine. The organic phase was dried over anhydrous sodium sulfate, filtered and concentrated to give a crude product of compound 27-9. MS [ESI, M+1]: 673.3

Step H: 3 mL of trifluoroacetic acid was added to a solution of compound 27-9 (120 mg, 178.25 µmol, 1 eq.) in dichloromethane (3 mL). The reaction mixture was subjected to reaction at 25° C. for 1 hour in nitrogen atmosphere, and concentrated to give a crude product. The crude product was separated twice by prep-HPLC (water (0.05% hydrochloric acid)-acetonitrile; water (0.225% formic acid v/v)-acetonitrile) to give compound 27. MS [ESI, M+1]: 573.1

¹H NMR (400 MHz, DMSO-d₆) δ=11.49 (s, 1H), 7.64 (d, J=2.4 Hz, 1H), 7.50 (d, J=7.6 Hz, 1H), 7.39 (d, J=8.0 Hz, 1H), 7.35-7.27 (m, 2H), 7.26-7.11 (m, 6H), 6.64-6.55 (m, 2H), 6.16 (d, J=15.6 Hz, 1H), 4.62 (d, J=5.6 Hz, 1H), 4.50 (d, J=5.6 Hz, 1H), 4.27-4.17 (m, 3H), 3.98-3.89 (m, 2H), 3.71-3.63 (m, 2H), 3.49-3.46 (m, 2H), 3.01-2.87 (m, 2H), 2.47-2.43 (m, 2H), 0.90 (t, J=7.2 Hz, 3H)

Experimental Example 1: MCF-7 Cell Proliferation Inhibition

Experimental Materials

EMEM medium was purchased from Wisent, and fetal bovine serum was purchased from Biosera. Promega CellTiter-Glo reagent. MCF-7 cells were purchased from the Cell Bank of Type Culture Collection Committee of the Chinese Academy of Sciences. Nivo5 multi-marker analyzer (PerkinElmer).

Method:

MCF-7 cells were seeded in a white 384-well plate at 600 cells/45 mL suspension/well. The plate was incubated in a $CO_2$ incubator overnight.

On the day of treatment, a day 0 plate coated under the same conditions the day before was taken, centrifuged to remove the medium, added with 25 microliters of Promega CellTiter-Glo reagent to each well, and incubated at room temperature for 10 minutes to stabilize the luminescence signal. Measures were read by PerkinElmer Nivo multi-marker analyzer as an initial value for 0% inhibition.

The test compounds were serially 5-fold diluted to the $10^{th}$ concentration with a multichannel pipette, i.e., from 2 millimoles to 0.1 nanomolar, and the experiments were set up in duplicate. 47.5 microliters of medium was added to the intermediate plate, 2.5 microliters of serially diluted compounds were transferred to corresponding wells of the intermediate plate, and after mixing, 5 microliters of the mixture per well was transferred to the cell plate. The plate was incubated in a $CO_2$ incubator for 6 days.

After 6 days of co-incubation with the compounds, the plate was centrifuged to remove the medium, added with 25 microliters of Promega CellTiter-Glo reagent to each well, and incubated at room temperature for 10 minutes to stabilize the luminescence signal. Measures were read by PerkinElmer Nivo multi-marker analyzer.

Data Analysis:

The original data was converted into inhibition rate by the formula: % inhibition=$((RFU_{Cmpd}-AVER(RFU_{Neg.Ctrl}))/((AVER(RFU_{Day0})-AVER(RFU_{Neg.Ctrl}))\times100\%$. Curve fitting was conducted and $IC_{50}$ was calculated.

The experimental results are shown in Table 1.

TABLE 1

Experimental results of in vitro MCF-7 cell proliferation inhibition

| Compound | $IC_{50}$ for MCF-7 cell proliferation inhibition (nM) |
| --- | --- |
| 1 | 1.41 |
| 2 | 0.64 |
| 3 | 0.87 |
| 4 | 0.61 |
| 5 | 4.74 |
| 6 | 1.95 |
| 7 | 4.25 |
| 8 | 2.72 |
| 9 | 2.36 |
| 10 | 2.11 |
| 11 | 4.13 |
| 12 | 2.73 |
| 13 | 1.12 |
| 14 | 1 |
| 15 | 1.6 |
| 16 | 1.11 |
| 17 | 2.67 |
| 18 | 2.35 |
| 19 | 2.75 |
| 20 | 1.46 |
| 21 | 2.21 |
| 22 | 2.69 |
| 23 | 1.65 |
| 24 | 6.19 |
| 25 | 1.01 |
| 26 | 3.82 |
| 27 | 0.49 |

Experimental Example 2: Evaluation of DMPK Properties (1) Assay of Metabolic Stability in Liver Microsome Objective: To determine the metabolic stability of test compounds in the liver microsomes of humans, CD-1 5 mice and SD rats (Corning Co., Ltd., Miaotong Biological Technology Co., Ltd., Miaotong Biological Technology Co., Ltd.).

Procedures: Firstly, eight 96-well plates were prepared, and named T0, T5, T10, T20, T30, T60, NCF60 and BLANK; except for BLANK (added with buffer at 10 μL/well), the plates were added with the solution of compounds at 10 μL/well. Prepared microsomes were added to the 7 plates (80 μL/well), except for the T0 10 plate. The NCF60 plate was added with the buffer at 10 μL/well, and incubated in a 37° C. water bath, and timing was started:

| Time point | Starting | End |
| --- | --- | --- |
| NCF60 | 1:00:00 | 0:00:00 |

Prepared NADPH cofactor working solution was aliquoted into a 96-well shallow-well plate serving as a loading slot. Each plates was added with the solution to at 10 μL/well by a 96-channel pipette and incubated in a 37° C. water bath to start the reaction:

| Time point | Starting | End |
| --- | --- | --- |
| Blank | 1:00:00 | 0:00:00 |
| T60 | 1:00:00 | 0:00:00 |
| T30 | 1:00:00 | 0:00:00 |
| T20 | 0:30:00 | 0:00:00 |
| T10 | 0:20:00 | 0:00:00 |
| T5 | 0:10:00 | 0:00:00 |
| T0 | Termination solution was added, followed by microsome working solution at 80 μL/well and NADPH cofactor working solution at 10 μL/well | |

At each time point, termination solution (cold acetonitrile containing 100 ng/mL Tolbutamide and 100 ng/mL Labetalol as internal standard) was added at 300 μL/well to stop the reaction, and the mixture was mixed well; the mixture was centrifuged at 4000 rpm for 20 minutes to precipitate the protein; the supernatant was transferred at 100 μL/well to a new 96-well plate containing 300 μL/well of HPLC water with a 96-channel pipette, and the mixture was mixed well. The mixture was subjected to LC/MS/MS analysis. The results are shown in Table 2.

2) Assay of Cytochrome P450 Isoenzyme Inhibition

Experimental objective: To determine the inhibitory effect of the test compound on the activity of human liver microsomal cytochrome P450 isoenzymes (CYP1A2, CYP2C9, CYP2C19, CYP2D6 and CYP3A4; Corning Co., Ltd.).

Experimental procedures: First, the test compound (10 mM) was diluted in gradient to prepare working solutions (100×final concentration) at concentrations of: 5, 1.5, 0.5, 0.15, 0.05, 0.015, and 0.005 mM, and working solutions of positive inhibitors for P450 isoenzymes (CYP1A2, CYP2C9, CYP2C19, CYP2D6, and CYP3A4) and the specific substrate mixtures thereof (5 in 1) were prepared simultaneously; human liver microsomes frozen in a −80° C. refrigerator were thawed on ice, and after all thawed, the human liver microsomes were diluted with PB to prepare a working solution at a specific concentration (0.253 mg/mL); 20 μL of the substrate mixture were added into the reaction plate (20 μL of PB was added into the blank well) and 158 μL of the working solution of human liver microsomes were also added into the reaction plate which was then placed on ice for use; then 2 μL of the test compound at each concentration (N=1) and a specific inhibitor (N=2) were added into the corresponding well, and the group without the inhibitor (test compound or the positive inhibitor) was added with a corresponding organic solvent as a control sample (the test compound control sample was 1:1 DMSO:MeOH; the positive control sample was 1:9 DMSO:MeOH); after pre-incubation in a 37° C. water bath for 10 min, 20 μL of a coenzyme factor (NADPH) solution was added into the reaction plate and incubated in a 37° C. water bath for 10 min, 400 μL of a cold acetonitrile solution (the internal standard was 200 ng/mL Tolbutamide and Labetalol) was added to terminate the reaction, and the reaction plate was placed on a shaker and shaken for 10 min; after centrifugation at 4,000 rpm for 20 min, 200 μL of the supernatant was collected and added to 100 μL of water to dilute the sample, and, finally, the plate was sealed, oscillated, shaken evenly, and subjected to LC/MS/MS detection. The results are shown in Table 2.

(3) MDR1-MDCK Two-Way Permeability Assay

In this study, the MDR1-MDCKII cell line authorized by the Piet Borst Laboratory of the Netherlands Cancer Institute was used as the in vitro model. It is a Madin-Darby canine kidney cell transfected with human multiple drug resistance gene (MDR1). The cells can stably express the efflux transporter P-gp, so it is suitable for screening P-gp substrates or inhibitors and predicting the permeability of the compounds through barriers with high efflux effects in the duodenum, blood-brain barrier, hepatocyte nucleus and kidney units, etc. This study was intended to use MDR1-MDCK II cells for investigating the two-way permeability of the test compounds through the MDR1-MDCK II cell model.

Procedures: The standard conditions are as follows:
Test concentration: 2 µM (DMSO≤1%);
Replicate: n=2;
Direction: Two-way transport, including two directions: A→B and B→A;
Incubation time: single time point, 2.5 hours;
Transport buffer: HBSS buffer containing 10 mM Hepes, pH 7.4; Incubation condition: 37° C., 5% $CO_2$.

After the incubation, sample solutions at the dosing end and the receiving end were collected and mixed with the cold acetonitrile solution containing the internal standard immediately. LC/MS/MS method was used to analyze the concentration of the test compounds in all samples (including the initial dosing solution, the dosing end samples and the receiving end samples). The apparent permeability coefficient, efflux ratio and other parameters were calculated. The results are shown in Table 2.

TABLE 2

Evaluation results of in vitro DMPK properties

| Item | Compound 3 monohydrochloride |
|---|---|
| Stability in liver microsomes (human, SD rat, CD-1 mouse) | 43, 35, 43 |
| CYP enzyme inhibition ($IC_{50}$, µM) 1A2/2C9/2C19/2D6/3A4 | 45.1/8.4/3.9/25.6/9.8 |
| Permeability Papp ($10^{-6}$ cm/s) (A-B, B-A, ratio) | 0.44, 1.93, 4.39 |

(4) Pharmacokinetics Study in Mice

Objective: To determine the drug concentration in the plasma of the mice at different times after intravenous and oral administration of the test compounds by LC/MS/MS using female Balb/c mice as the test animals. To investigate the pharmacokinetic performance of the test compounds in mice and to evaluate the pharmacokinetic characteristics.

Experimental Procedure:

Test animals: 4 healthy female Balb/c mice were divided into 2 groups according to the principle of similar weight, 2 in the IV group and 2 in the PO group. The animals were purchased from Shanghai Lingchang Biotechnology Co., Ltd.

Drug Preparation:

IV group: Appropriate amounts of compounds were weighed respectively, prepared into 2 mg/mL solutions, then mixed to give a 0.5 mg/mL solution, which was stirred and ultrasonicated until a clear state. The vehicle was 15% HP-b-CD.

PO group: An appropriate amount of the IV group solution was taken and diluted to 0.4 mg/mL with 15% HP-b-CD.

Administration: After fasting overnight, the IV group was administered intravenously, and the dose of the test compound was 1 mg/kg; the PO group was administered intragastrically, and the dose of the test compound was 2 mg/kg.

Procedures: For IV group, 30 µL of blood was collected from the saphenous vein of the female Balb/c mice at 0.0833, 0.25, 0.5, 1, 2, 4, 8, and 24 hours post-dose, and placed in a commercial anticoagulant tube with EDTA-K2 added in advance. For PO group, 30 µL of blood was collected from the saphenous vein of the female Balb/c mice at 0.25, 0.5, 1, 2, 4, 8, 12 and 24 hours post-dose, and placed in a commercial anticoagulant tube with EDTA-K2 added in advance. The blood samples were centrifuged (3,200 g, 4° C., 10 minutes) to give plasma samples, which was transferred to a pre-cooled centrifuge tube, frozen in dry ice, and stored in an ultra-low temperature freezer at −60° C. or lower until the LC-MS/MS analysis. The animals were given free access to food 4 hours after the administration. LC/MS/MS method was used to determine the content of the test compounds in the plasma of mice after intravenous and oral administration. The linear range of the method is 2.00-2000 nM. The results are shown in Table 3.

(5) Pharmacokinetics Study in Rats

Experimental objective: To determine the drug concentration in the plasma of the rats at different times after intravenous and oral administration of the test compounds by LC/MS/MS using female SD rats as the test animals. To investigate the pharmacokinetic performance of the test compounds in rats and to evaluate the pharmacokinetic characteristics.

Experimental Procedure

Test animals: 4 healthy female SD rats were divided into 2 groups according to according to the principle of similar weight, 2 in the IV group and 2 in the PO group. Animal used in this study were purchased from Beijing Vital River Laboratory Animal Technology Co., Ltd.

Drug Preparation:

IV group: Appropriate amounts of compounds were weighed respectively, prepared into 2 mg/mL solutions, then mixed to give a 0.5 mg/mL solution, which was stirred and ultrasonicated until a clear state. The vehicle was 15% HP-b-CD.

PO group: An appropriate amount of the IV group solution was taken and diluted to 0.4 mg/mL with 15% HP-b-CD.

Administration: After fasting overnight, the IV group was administered intravenously, and the dose of the test compound was 1 mg/kg; the PO group was administered intragastrically, and the dose of the test compound was 2 mg/kg.

Procedures: For IV group, 200 µL of blood was collected from the jugular vein of the female SD rats at 0.0833, 0.25, 0.5, 1, 2, 4, 8, and 24 hours post-dose, and placed in a commercial anticoagulant tube with EDTA-K2 added in advance. For PO group, 200 µL of blood was collected from the jugular vein of the female SD rats at 0.25, 0.5, 1, 2, 4, 8, 12 and 24 hours post-dose, and placed in a commercial anticoagulant tube with EDTA-K2 added in advance. The blood samples were centrifuged (3,200 g, 4° C., 10 minutes) to give plasma samples, which was transferred to a pre-cooled centrifuge tube, frozen in dry ice, and stored in an ultra-low temperature freezer at −60° C. or lower until the LC-MS/MS analysis. The animals were given free access to food 4 hours after the administration. LC/MS/MS method was used to determine the content of the test compounds inthe plasma of mice after intravenous and oral administration. The linear range of the method is 2.00-2000 nM. The results are shown in Table 3.

The results of in vivo PK properties are shown in Table 3:

TABLE 3

Evaluation results of in vivo PK properties

| | | Mouse Cassette PK | | Rat Cassette PK | |
|---|---|---|---|---|---|
| | Parameters | Compound 3 Monohydrochloride | Compound 4 Monohydrochloride | Compound 3 Monohydrochloride | Compound 4 Monohydrochloride |
| i.v. (1 mg/kg) | $T_{1/2}$ (h) | 3.37 | 1.85 | 6.65 | 3.98 |
| | $Vd_{ss}$ (L/kg) | 3.46 | 3.45 | 4.46 | 4.86 |
| | Cl (mL/min/kg) | 12.9 | 26.0 | 8.14 | 15.8 |
| | $AUC_{0-last}$ (nM · h) | 2427 | 1096 | 3550 | 1896 |
| p.o. (2 mg/kg) | $C_{max}$ (nM) | 224 | 159 | 464 | 233 |
| | $T_{max}$ (h) | 0.250 | 0.250 | 2.00 | 2.00 |
| | $T_{1/2}$ (h) | 8.12 | 3.25 | ND | 3.26 |
| | $AUC_{0-last}$ (nM · h) | 1268 | 503 | 5206 | 1836 |
| | F % | 26.1 | 22.9 | 73.3 | 48.4 |

Experimental Example 3: In Vivo Efficacy Evaluation

This study was intended to evaluate the anti-tumor efficacy of compounds of the present application in MCF-7 breast cancer cell xenograft BALB/c nude mice (provided by Beijing Vital River Laboratory Animal Technology Co., Ltd., with the number of test animals in each experimental group being 7).

Three days before the xenograft, the mice were inoculated with 0.36 mg of 60-day sustained-release estrogen tablets subcutaneously on the left shoulder. In the logarithmic growth phase, the cells were collected and counted. The cell density was adjusted to $10 \times 10^7$ cells/mL, added with an equal volume of Matrigel and mixed for inoculation. Each mouse was xenografted subcutaneously with 0.2 mL of MCF-7 tumor cell suspension ($10 \times 10^6$) on the right shoulder. On the 14th day after tumor cell xenograft, the mice were grouped and administered the drugs once a day, with an average tumor volume of 200 mm³ and a body weight of 22.0-23.0 g. Tumor volume and body weight were measured twice a week after grouping. The tumor growth rate (T/C) and tumor growth inhibition rate (TGI) were calculated for the last tumor measurement data on the 27th day after grouping, and the anti-tumor efficacy of the compound was evaluated by TGI (%) or relative tumor proliferation rate T/C (%). TGI (%), reflects the tumor growth inhibition rate. TGI (%)=[(1-(average tumor volume at the end of treatment in a treatment group—average tumor volume at the start of treatment in the treatment group))/(average tumor volume at the end of treatment in the solvent control group—average tumor volume at the start of treatment in the solvent control group)]×100%, relative tumor proliferation rate T/C (%)=$T_{RTV}/C_{RTV}$×100% ($T_RTV$: average RTV in the treatment group; $C_{RTV}$: average RTV in the negative control group). Relative tumor volume (RTV) was calculated based on the results of tumor measurement. The formula is RTV=$V_t/V_0$, wherein $V_0$ is the tumor volume measured when grouping and administering (i.e., $D_0$), and $V_t$ is the tumor volume at a certain measurement, the data of $T_{RTV}$ and $C_{RTV}$ should be measured on the same day. The results are as follows:

TABLE 4

Analysis of anti-tumor efficacy

| Test compound | Tumor volume (mm³)[a] 27 days after grouping | T/C (%) | TGI (%) | p |
|---|---|---|---|---|
| Compound 4 monohydrochloride (3 mg/kg) | 396 ± 58 | 28.74 | 83 | 0.001 |
| Compound 4 monohydrochloride (10 mg/kg) | 124 ± 5 | 9.32 | 106 | <0.001 |

[a]Mean ± SEM.

Experimental Example 4: Uterine Wet Weight Inhibition in Immature Rats

This study was intended to evaluate the uterine growth inhibition of compounds of the present application in female immature rats aged 18-21 days (provided by Beijing Vital River Laboratory Animal Technology Co., Ltd., with the number of test animals in each experimental group being 5). In this study, 18-day-old female immature rats were given oral doses of 10 mg/kg of the compound of the present application and 0.1 mg/kg of estradiol for three consecutive days, the control group was given oral doses of 0.1 mg/kg of estradiol for three consecutive days, and the blank group was given no drugs except the corresponding vehicle. Three days after the administration, the rats were sacrificed, and the uteruses of the rats were weighed to observe the effect of the test compound on the uterine growth inhibition in rats. Inhibition rate=100*[(Vehicle$_{EE}$-Cpd)/(Vehicle$_{EE}$-Vehicle)], wherein Vehicle$_{EE}$ is uterine wet weight in the control group (oral doses of 0.1 mg/kg estradiol); Cpd is the uterine wet weight of the treatment group; Vehicle is the uterine wet weight of rats in the blank group. The results are as follows:

| Test compound | Uterine wet weight (g) | Inhibition rate (%) |
|---|---|---|
| Blank | 0.0500 | — |
| Estradiol (0.1 mg) | 0.1200 | — |
| Compound 1 (10 mg/kg) + estradiol (0.1 mg/kg) | 0.0672 | 75 |

What is claimed is:

1. A compound of formula (II), an stereoisomer thereof or a pharmaceutically acceptable salt thereof,

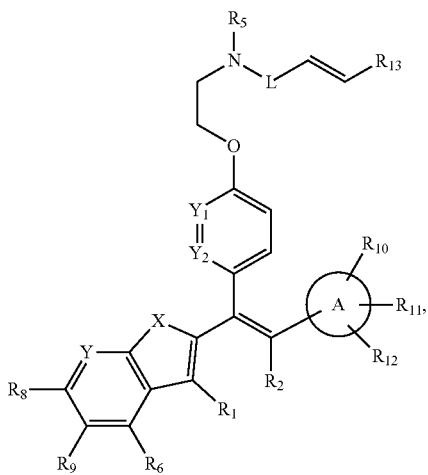

wherein,
X is NH;
Y is selected from the group consisting of N and $CR_7$;
$Y_1$ is CH, and $Y_2$ is N;
or, $Y_1$ is N, and $Y_2$ is CH or CF;
or, $Y_1$ is CH, and $Y_2$ is CH;
L is

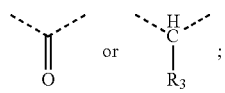

ring A is selected from the group consisting of $C_{6-10}$ aryl and 5-10 membered heteroaryl;
$R_1$ is selected from the group consisting of H, halogen, CN, COOH, $NH_2$, $C_{1-6}$ alkyl, $C_{1-6}$ heteroalkyl, $C_{3-6}$ cycloalkyl and 3-6 membered heterocycloalkyl, the $C_{1-6}$ alkyl, $C_{1-6}$ heteroalkyl, $C_{3-6}$ cycloalkyl and 3-6 membered heterocycloalkyl being optionally substituted with 1, 2 or 3 $R_a$;
$R_2$ is selected from the group consisting of $C_{1-6}$ alkyl, $C_{1-6}$ heteroalkyl, $C_{3-6}$ cycloalkyl and 3-6 membered heterocycloalkyl, the $C_{1-6}$ alkyl, $C_{1-6}$ heteroalkyl, $C_{3-6}$ cycloalkyl and 3-6 membered heterocycloalkyl being optionally substituted with 1, 2 or 3 $R_b$;
$R_3$ is selected from the group consisting of H, halogen, CN, $NO_2$, OH, COOH, $NH_2$, $C_{1-6}$ alkyl, $C_{1-6}$ heteroalkyl, $C_{3-6}$ cycloalkyl and 3-6 membered heterocycloalkyl, the $C_{1-6}$ alkyl, $C_{1-6}$ heteroalkyl, $C_{3-6}$ cycloalkyl and 3-6 membered heterocycloalkyl being optionally substituted with 1, 2 or 3 $R_c$;
$R_{13}$ is H or

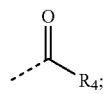

$R_4$ is selected from the group consisting of COOH, $NH_2$, $C_{1-6}$ alkyl, $-NH-C_{1-6}$ alkyl, $-N(C_{1-6}$ alkyl$)_2$, $-C(=O)-O-C_{1-6}$ alkyl, $-C(=O)-S-C_{1-6}$ alkyl, $C_{3-6}$ cycloalkyl, 3-6 membered heterocycloalkyl, phenyl and 5-6 membered heteroaryl, the $C_{1-6}$ alkyl, $-NH-C_{1-6}$ alkyl, $-N(C_{1-6}$ alkyl$)_2$, $-C(=O)-O-C_{1-6}$ alkyl, $-C(=O)-S-C_{1-6}$ alkyl, $C_{3-6}$ cycloalkyl, 3-6 membered heterocycloalkyl, phenyl and 5-6 membered heteroaryl being optionally substituted with 1, 2 or 3 $R_d$;
$R_5$ is selected from the group consisting of H, $C_{1-6}$ alkyl, $C_{1-6}$ heteroalkyl, $C_{3-6}$ cycloalkyl and 3-6 membered heterocycloalkyl, the $C_{1-6}$ alkyl, $C_{1-6}$ heteroalkyl, $C_{3-6}$ cycloalkyl and 3-6 membered heterocycloalkyl being optionally substituted with 1, 2 or 3 $R_e$;
$R_6$, $R_7$, $R_8$ and $R_9$ are each independently selected from the group consisting of H, halogen, CN, $NO_2$, OH, COOH, $NH_2$, $C_{1-6}$ alkyl, $C_{1-6}$ heteroalkyl, $C_{3-6}$ cycloalkyl and 3-6 membered heterocycloalkyl, the $C_{1-6}$ alkyl, $C_{1-6}$ heteroalkyl, $C_{3-6}$ cycloalkyl and 3-6 membered heterocycloalkyl being optionally substituted with 1, 2 or 3 $R_f$;
$R_{10}$, $R_{11}$ and $R_{12}$ are each independently selected from the group consisting of H, halogen, CN, $NO_2$, OH, COOH, $NH_2$, $C_{1-6}$ alkyl, $C_{1-6}$ heteroalkyl, $C_{3-6}$ cycloalkyl and 3-6 membered heterocycloalkyl, the $C_{1-6}$ alkyl, $C_{1-6}$ heteroalkyl, $C_{3-6}$ cycloalkyl and 3-6 membered heterocycloalkyl being optionally substituted with 1, 2 or 3 $R_g$;
$R_a$, $R_b$, $R_c$, $R_d$, $R_e$, $R_f$ and $R_g$ are each independently selected from the group consisting of H, F, Cl, Br, I, OH, CN, $NH_2$, COOH, $C(=O)NH_2$, $C_{1-8}$ alkyl, $C_{1-8}$ heteroalkyl, $C_{3-6}$ cycloalkyl, 3-6 membered heterocycloalkyl and $C_{3-6}$ cycloalkyl-$C_{1-3}$ alkyl-, the $C_{1-8}$ alkyl, $C_{1-8}$ heteroalkyl, $C_{3-6}$ cycloalkyl, 3-6 membered heterocycloalkyl and $C_{3-6}$ cycloalkyl-$C_{1-3}$ alkyl-being optionally substituted with 1, 2 or 3 R;
R is independently selected from the group consisting of F, Cl, Br, I, OH, CN, $NH_2$, COOH, Me, Et, $CF_3$, $CHF_2$, $CH_2F$, $NHCH_3$, and $N(CH_3)_2$;
the $C_{1-6}$ heteroalkyl, 3-6 membered heterocycloalkyl and 5-6 membered heteroaryl each comprise 1, 2, 3 or 4 heteroatoms or heteroatom groups each independently selected from the group consisting of $-NH-$, $-O-$, $-S-$, $-O-N=$, $-C(=O)-O-$, $-C(=O)-S-$, $-C(=O)-$, $-C(=S)-$, $-S(=O)-$, $-S(=O)_2-$ and N.

2. The compound, the stereoisomer thereof, or the pharmaceutically acceptable salt thereof according to claim 1, wherein Y is $CR_7$; $Y_1$ is CH and $Y_2$ is N, or, $Y_1$ is N and $Y_2$ is CH;
L is

$R_{13}$ is

3. The compound, the stereoisomer thereof, or the pharmaceutically acceptable salt thereof according to claim 1, wherein $R_a$, $R_b$, $R_c$, $R_d$, $R_e$, $R_f$ and $R_g$ are each independently selected from the group consisting of H, F, Cl, Br, I, OH, CN, $NH_2$, COOH, C(=O)$NH_2$, $C_{1-6}$ alkyl, $C_{1-6}$ heteroalkyl and cyclopropyl, the $C_{1-6}$ alkyl, $C_{1-6}$ heteroalkyl and cyclopropyl being optionally substituted with 1, 2 or 3 R.

4. The compound, the stereoisomer thereof, or the pharmaceutically acceptable salt thereof according to claim 1, wherein ring A is selected from the group consisting of phenyl and 5-6 membered heteroaryl.

5. The compound, the stereoisomer thereof, or the pharmaceutically acceptable salt thereof according to claim 1, wherein $R_1$ is selected from the group consisting of H, F, Cl, Br, I, CN, COOH, $NH_2$, $C_{1-3}$ alkyl and $C_{1-3}$ heteroalkyl, the $C_{1-3}$ alkyl and $C_{1-3}$ heteroalkyl being optionally substituted with 1, 2 or 3 $R_a$.

6. The compound, the stereoisomer thereof, or the pharmaceutically acceptable salt thereof according to claim 1, wherein $R_2$ is selected from the group consisting of $C_{1-3}$ alkyl and $C_{1-3}$ heteroalkyl, the $C_{1-3}$ alkyl and $C_{1-3}$ heteroalkyl being optionally substituted with 1, 2 or 3 $R_b$.

7. The compound, the stereoisomer thereof, or the pharmaceutically acceptable salt thereof according to claim 1, wherein $R_3$ is selected from the group consisting of H and $C_{1-6}$ alkyl.

8. The compound, the stereoisomer thereof, or the pharmaceutically acceptable salt thereof according to claim 1, wherein $R_4$ is selected from the group consisting of COOH, $NH_2$, $C_{1-6}$ alkyl, —NH—$C_{1-6}$ alkyl, —N($C_{1-6}$ alkyl)$_2$, —C(=O)—O—$C_{1-6}$ alkyl, —C(=O)—S—$C_{1-6}$ alkyl, $C_{3-6}$ cycloalkyl, 3-6 membered heterocycloalkyl and phenyl, the $C_{1-6}$ alkyl, —NH—$C_{1-6}$ alkyl, —N($C_{1-6}$ alkyl)$_2$, —C(=O)—O—$C_{1-6}$ alkyl, —C(=O)—S—$C_{1-6}$ alkyl, $C_{3-6}$ cycloalkyl, 3-6 membered heterocycloalkyl and phenyl being optionally substituted with 1, 2 or 3 $R_d$.

9. The compound, the stereoisomer thereof, or the pharmaceutically acceptable salt thereof according to claim 1, wherein $R_5$ is selected from the group consisting of H, $C_{1-3}$ alkyl and $C_{1-3}$ heteroalkyl, the $C_{1-3}$ alkyl and $C_{1-3}$ heteroalkyl being optionally substituted with 1, 2 or 3 $R_e$.

10. The compound, the stereoisomer thereof, or the pharmaceutically acceptable salt thereof according to claim 1, wherein $R_6$, $R_7$, $R_8$ and $R_9$ are H.

11. The compound, the stereoisomer thereof, or the pharmaceutically acceptable salt thereof according to claim 1, wherein $R_{10}$, $R_{11}$ and $R_{12}$ are each independently selected from H, F, Cl, Br, I, CN, $NO_2$, OH, COOH, $NH_2$, $C_{1-3}$ alkyl and $C_{1-3}$ heteroalkyl, the $C_{1-3}$ alkyl and $C_{1-3}$ heteroalkyl being optionally substituted with 1, 2 or 3 $R_g$.

12. The compound, the stereoisomer thereof, or the pharmaceutically acceptable salt thereof according to claim 1, wherein the structural unit

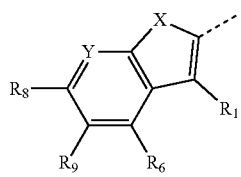

is selected from

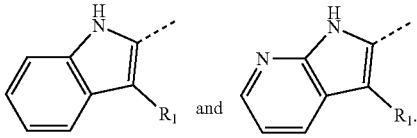

13. The compound, the stereoisomer thereof, or the pharmaceutically acceptable salt thereof according to claim 1, wherein the structural unit

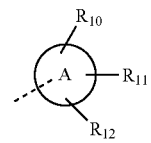

is selected from the group consisting of

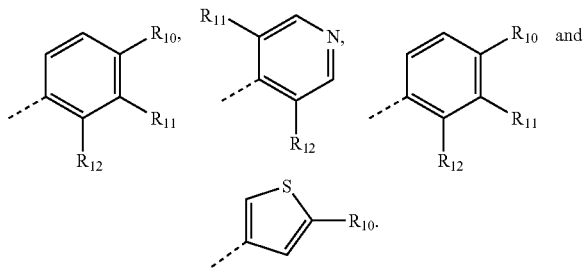

14. The compound, the stereoisomer thereof, or the pharmaceutically acceptable salt thereof according to claim 1, wherein $R_{13}$ is H, or

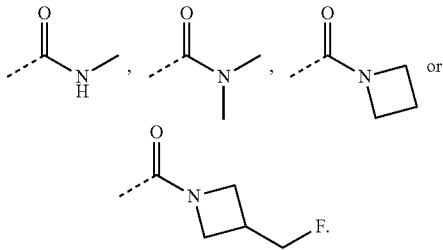

15. The compound, the stereoisomer thereof, or the pharmaceutically acceptable salt thereof according to claim 1, wherein the structural unit

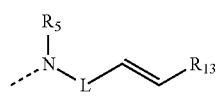

is selected from the group consisting of

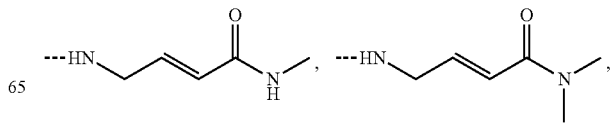

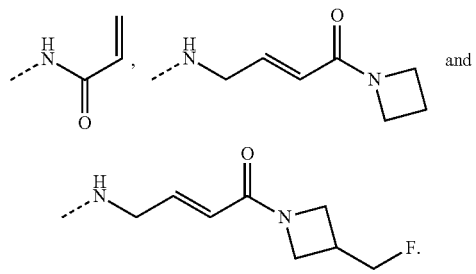

16. The compound, the stereoisomer thereof, or the pharmaceutically acceptable salt thereof according to claim 1, wherein the compound, the stereoisomer thereof, or the pharmaceutically acceptable salt thereof is selected from

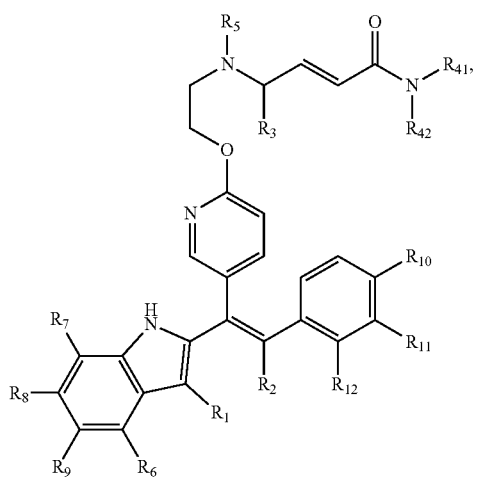

(I-3)

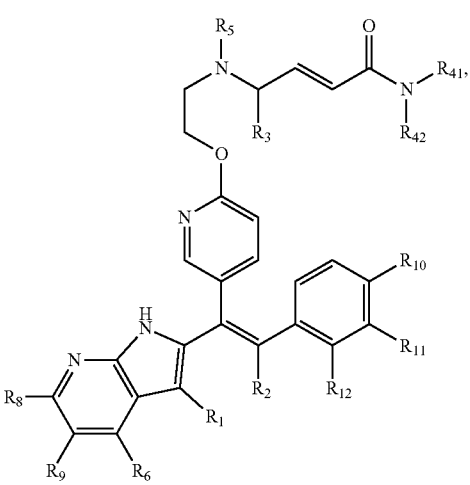

(I-6)

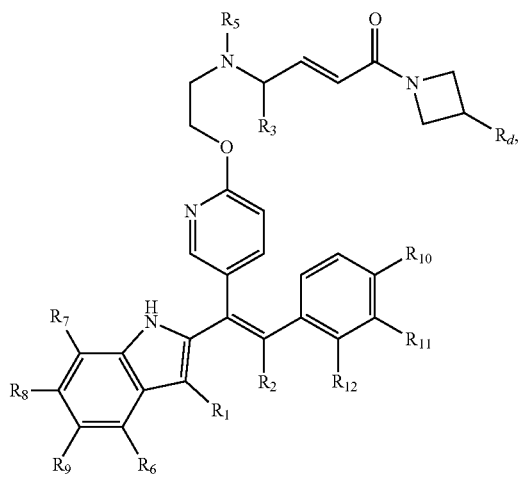

(II-1)

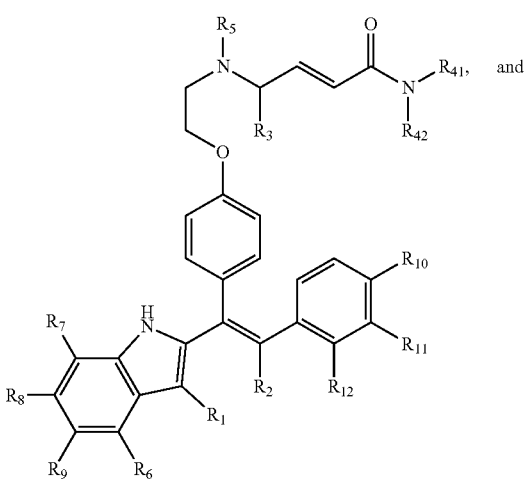

(II-2)

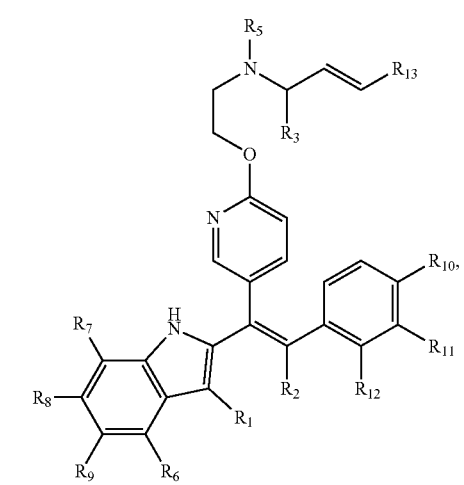

(II-3)

wherein,
$R_1$, $R_2$, $R_3$, $R_5$, $R_6$, $R_7$, $R_8$, $R_9$, $R_{10}$, $R_{11}$, $R_{12}$ and $R_{13}$ are as defined in claim 1,
$R_{41}$ and $R_{42}$ are each independently selected from H and $C_{1-6}$ alkyl, the $C_{1-6}$ alkyl being optionally substituted with 1, 2 or 3 $R_d$,
$R_d$ being as defined in claim 1.

17. The compound, the stereoisomer thereof, or the pharmaceutically acceptable salt thereof according to claim 1, wherein the compound is selected from:
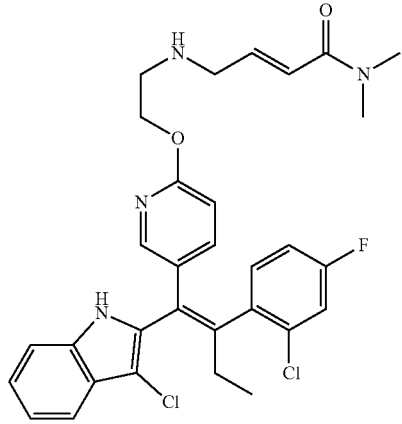
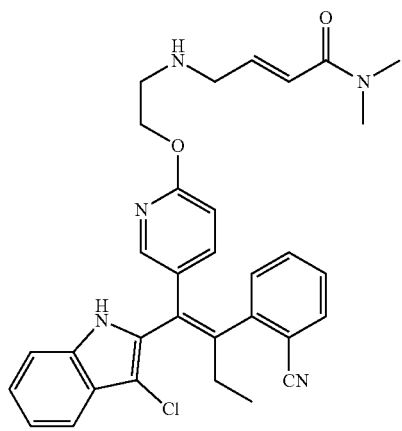
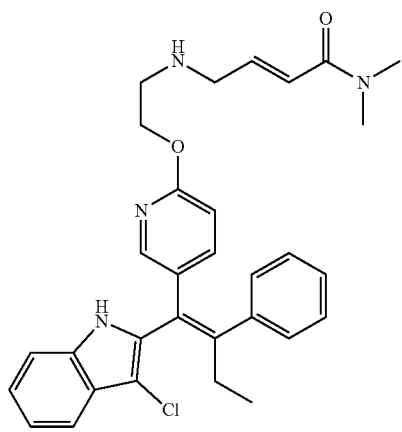
-continued
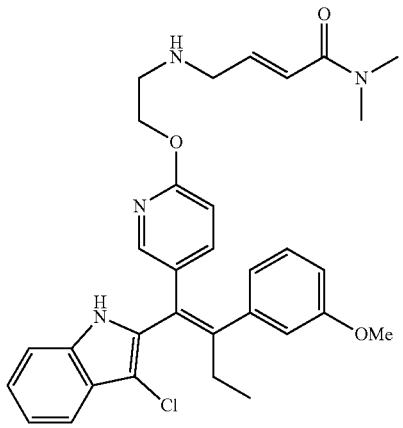
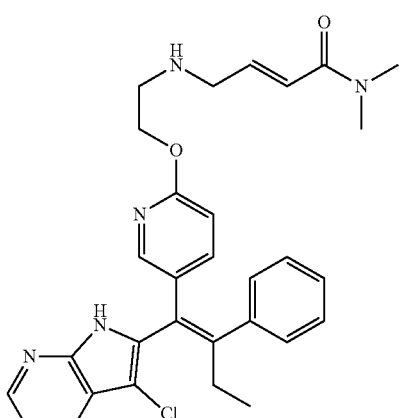
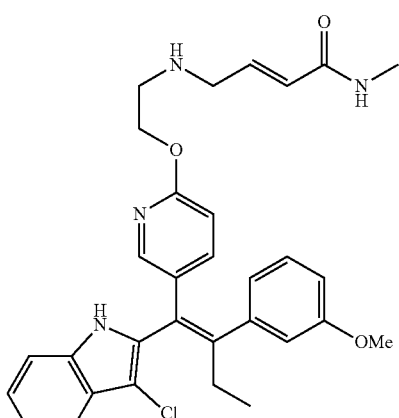
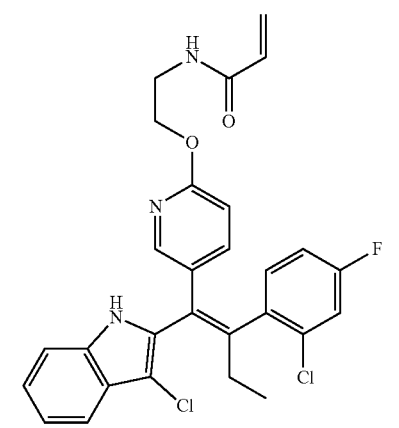

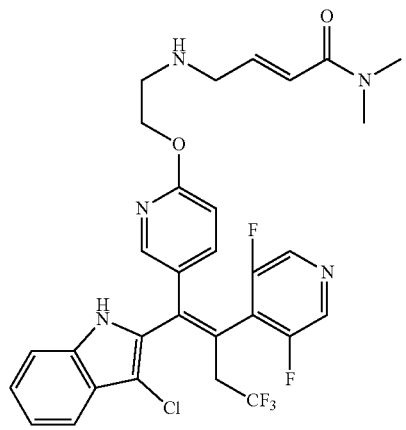
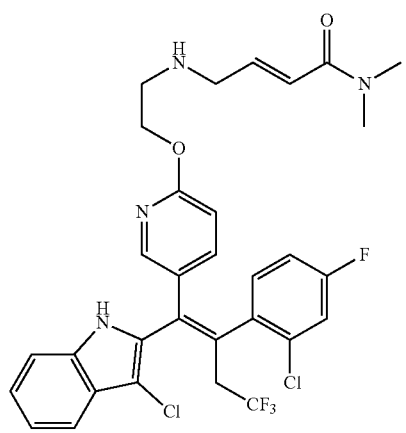
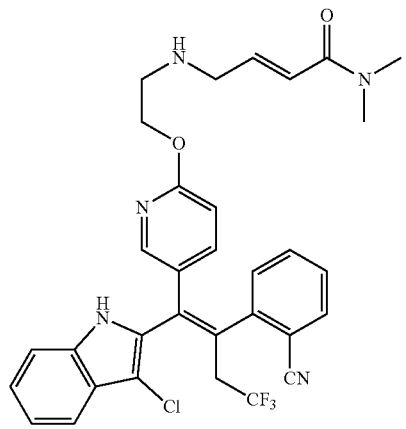
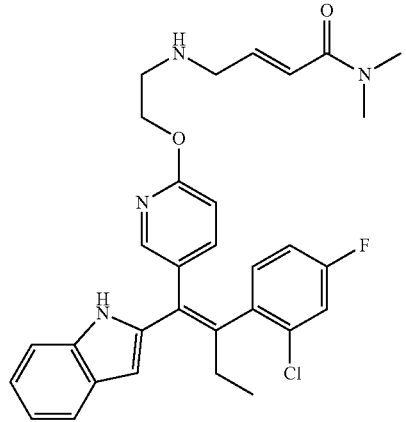
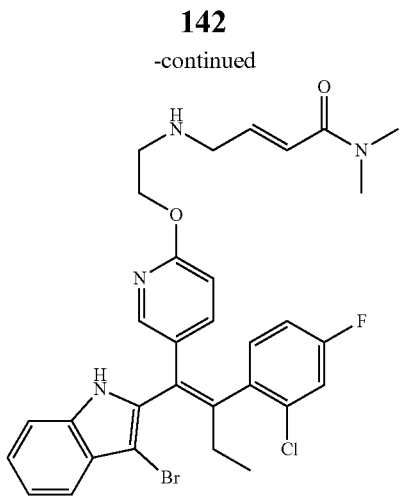
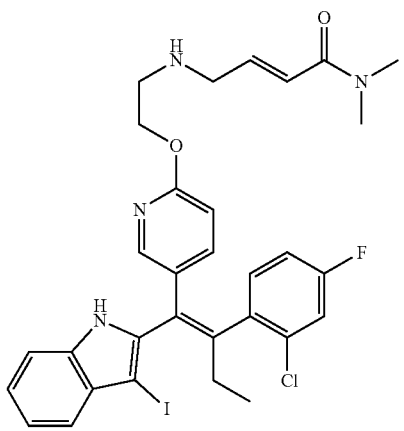
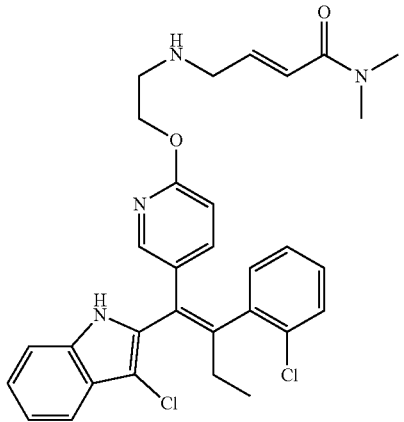
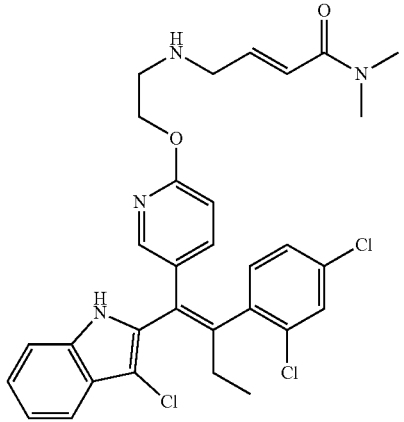

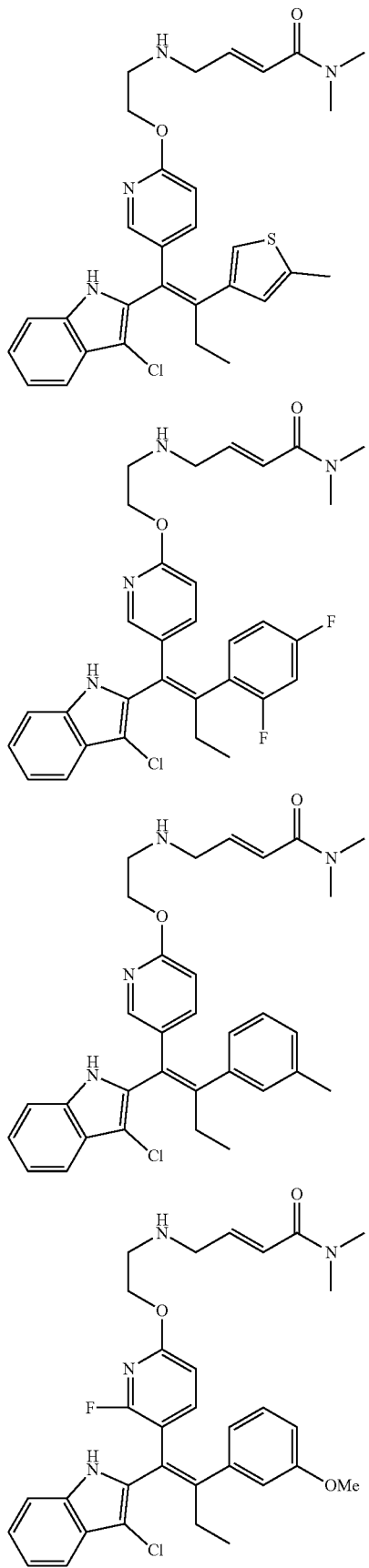
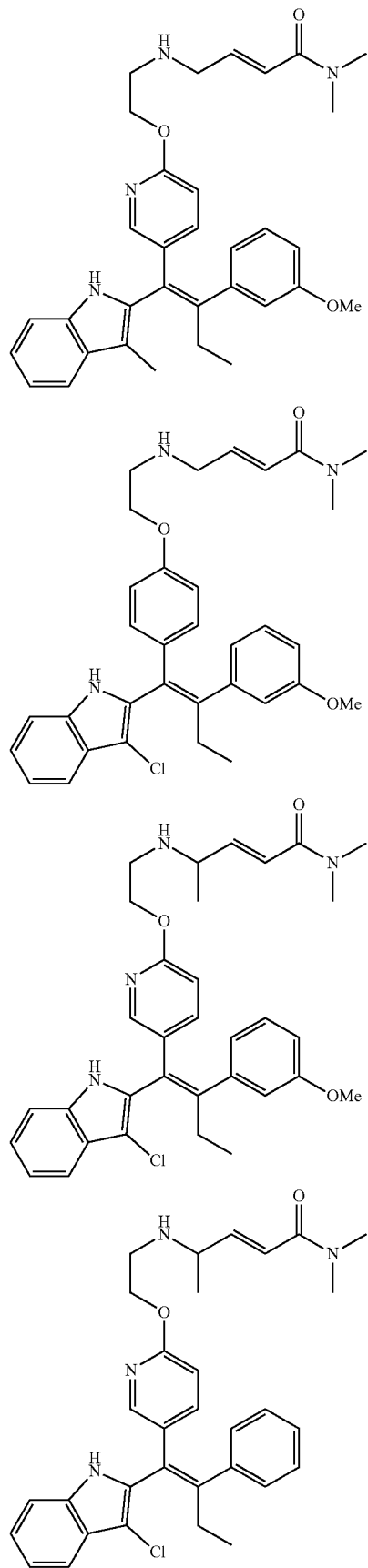

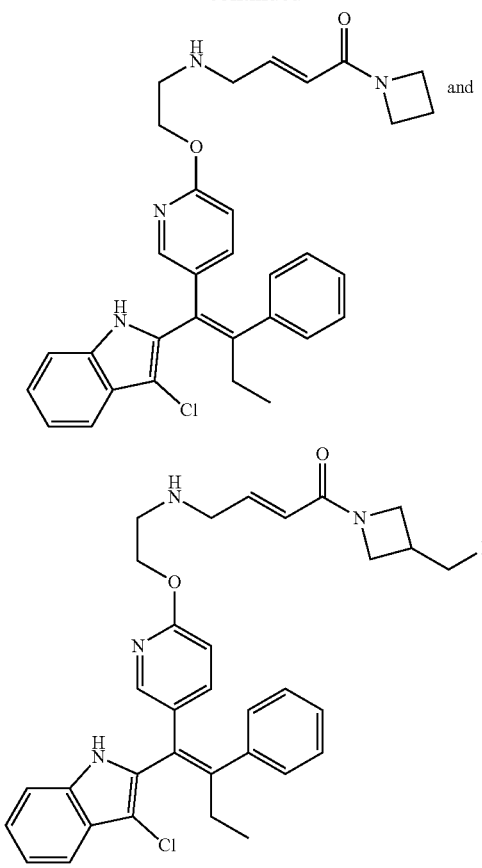

18. The compound, the stereoisomer thereof, or the pharmaceutically acceptable salt thereof according to claim 17, wherein the compound is selected from:

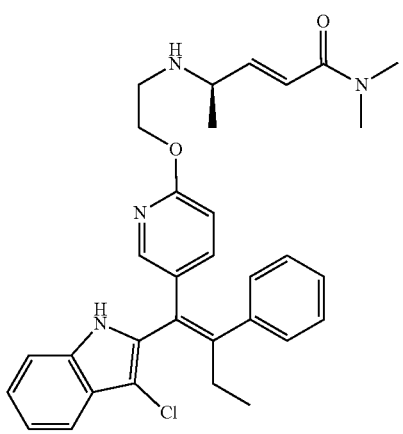

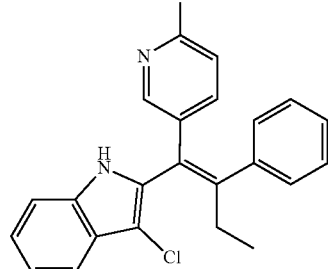

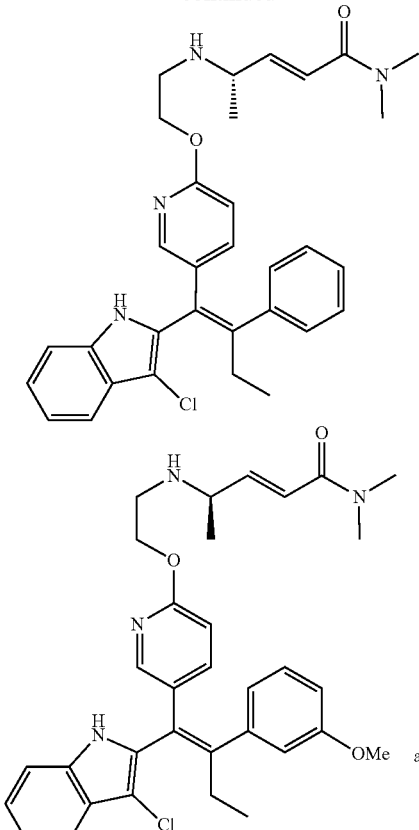

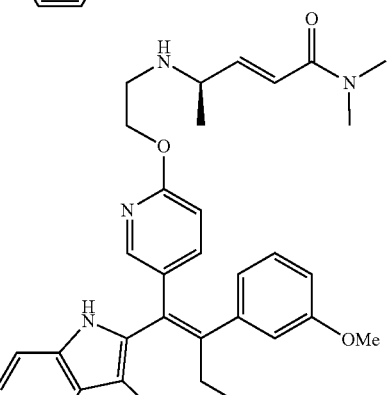

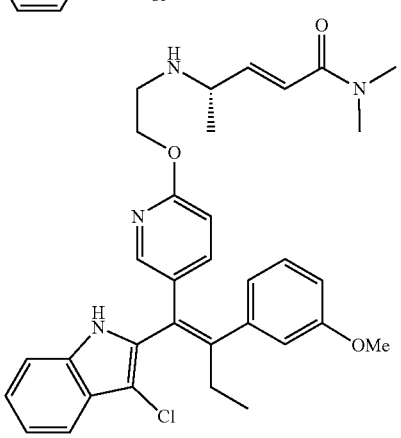

19. A pharmaceutical composition comprising a therapeutically effective amount of the compound, the stereoisomer thereof, or the pharmaceutically acceptable salt thereof according to claim 1 as an active ingredient, and a pharmaceutically acceptable carrier.

20. A method for treating estrogen receptor positive breast cancer, comprising administering a therapeutically effective amount of the compound, the stereoisomer thereof, or the pharmaceutically acceptable salt thereof according to claim 1, or the pharmaceutical composition thereof.

* * * * *